US011155563B2

(12) United States Patent
Cui et al.

(10) Patent No.: US 11,155,563 B2
(45) Date of Patent: Oct. 26, 2021

(54) MACROCYCLIC COMPOUNDS AND USES THEREOF

(71) Applicant: TURNING POINT THERAPEUTICS, INC., San Diego, CA (US)

(72) Inventors: Jingrong Jean Cui, San Diego, CA (US); Evan W. Rogers, San Diego, CA (US); Jane Ung, San Diego, CA (US); Jeffrey Whitten, San Diego, CA (US); Dayong Zhai, San Diego, CA (US); Wei Deng, San Diego, CA (US); Xin Zhang, San Diego, CA (US); Zhongdong Huang, San Diego, CA (US); Jing Liu, San Diego, CA (US); Han Zhang, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 10 days.

(21) Appl. No.: 17/213,093

(22) Filed: Mar. 25, 2021

(65) Prior Publication Data
US 2021/0214373 A1 Jul. 15, 2021

Related U.S. Application Data

(63) Continuation of application No. 16/634,289, filed as application No. PCT/US2018/043817 on Jul. 26, 2018.

(60) Provisional application No. 62/700,990, filed on Jul. 20, 2018, provisional application No. 62/538,193, filed on Jul. 28, 2017.

(51) Int. Cl.
*C07D 498/16* (2006.01)
*A61P 35/00* (2006.01)
*C07K 16/28* (2006.01)
*A61K 45/06* (2006.01)

(52) U.S. Cl.
CPC ............ *C07D 498/16* (2013.01); *A61P 35/00* (2018.01); *C07K 16/2863* (2013.01); *A61K 45/06* (2013.01)

(58) Field of Classification Search
CPC ........ C07D 498/16; C07K 16/28; A61P 35/00
See application file for complete search history.

(56) References Cited

U.S. PATENT DOCUMENTS

| | | | |
|---|---|---|---|
| 5,639,778 A | 6/1997 | Andersson et al. |
| 5,698,578 A | 12/1997 | Heath et al. |
| 8,497,270 B2 | 7/2013 | Thuring et al. |
| 8,680,111 B2 | 3/2014 | Bailey et al. |
| 8,815,872 B2 | 8/2014 | Yu et al. |
| 8,933,084 B2 | 1/2015 | Andrews et al. |
| 9,714,258 B2 | 7/2017 | Cui et al. |
| 10,246,466 B2 | 4/2019 | Cui et al. |
| 10,294,242 B2 | 5/2019 | Cui et al. |
| 10,316,044 B2 | 6/2019 | Cui et al. |
| 2011/0294801 A1 | 12/2011 | Yu et al. |
| 2013/0143895 A1 | 6/2013 | Mc et al. |
| 2013/0203776 A1 | 8/2013 | Andrews et al. |
| 2013/0245021 A1 | 9/2013 | Bi et al. |
| 2013/0252961 A1 | 9/2013 | Bailey et al. |
| 2014/0107099 A1 | 4/2014 | Blaney et al. |
| 2014/0206805 A1 | 7/2014 | Beutner et al. |
| 2016/0339027 A1 | 11/2016 | Carter et al. |
| 2017/0002023 A1 | 1/2017 | Cui et al. |
| 2017/0334929 A1 | 11/2017 | Cui et al. |
| 2018/0186813 A1 | 7/2018 | Cui et al. |
| 2018/0194777 A1 | 7/2018 | Cui et al. |
| 2018/0325901 A1 | 11/2018 | Cui et al. |
| 2020/0157119 A1* | 5/2020 | Cui .................... A61P 35/00 |

FOREIGN PATENT DOCUMENTS

| | | |
|---|---|---|
| CL | 2012003227 A1 | 2/2013 |
| EP | 3658148 A1 | 6/2020 |
| JP | 2012502043 A | 1/2012 |
| WO | 02/46197 A1 | 6/2002 |
| WO | 2010/028116 A1 | 3/2010 |
| WO | 2010/033941 A1 | 3/2010 |
| WO | 2010/048314 A1 | 4/2010 |
| WO | 2010/051549 A1 | 5/2010 |
| WO | 2011/146336 A1 | 11/2011 |
| WO | 2012/034091 A1 | 3/2012 |
| WO | 2012/136859 A1 | 10/2012 |
| WO | 2013/001310 A1 | 1/2013 |
| WO | 2013/028465 A1 | 2/2013 |
| WO | 2013/045653 A1 | 4/2013 |
| WO | 2013/132376 A1 | 9/2013 |
| WO | 2013/134219 A1 | 9/2013 |
| WO | 2013/134228 A1 | 9/2013 |
| WO | 2013/147711 A1 | 10/2013 |
| WO | 2015/112806 A2 | 7/2015 |
| WO | 2017/004342 A1 | 1/2017 |
| WO | 2017/007759 A1 | 1/2017 |

(Continued)

OTHER PUBLICATIONS (Aug. 10, 2015) Pubchem SID 252159180, 4 pages.
(Dec. 11, 2015) "1-(5-Methyl-1,6,7,8-tetrahydropyrrolo[2,3-g]quinolin-3-yl)ethanone", PubChem CID 98009788, , 10 pages.
International Preliminary Report on Patentability received for PCT Application No. PCT/US2018/043817, dated Feb. 6, 2020, 9 pages.
International Search Report and Written Opinion received for Application No. PCT/US2015/012597, dated Aug. 28, 2015, 11 Pages.
International Search Report and Written Opinion received for Application No. PCT/US2016/043132, dated Sep. 28, 2016, 15 Pages.

(Continued)

Primary Examiner — Erich A Leeser
(74) Attorney, Agent, or Firm — Mintz Levin Cohn Ferris Glovsky and Popeo P.C.

(57) ABSTRACT

The present disclosure relates to certain macrocyclic compounds that inhibit SRC and MET, and/or CSF1R, pharmaceutical compositions containing such compounds, and methods of using such compounds to treat cancer.

3 Claims, 20 Drawing Sheets

(56) References Cited

FOREIGN PATENT DOCUMENTS

| WO | 2017/015367 A1 | 1/2017 |
|---|---|---|
| WO | 2018/022911 A1 | 2/2018 |
| WO | 2018/140554 A1 | 8/2018 |
| WO | 2019/023417 A1 | 1/2019 |
| WO | 2019/120267 A1 | 6/2019 |
| WO | 2019/201282 A1 | 10/2019 |

OTHER PUBLICATIONS

International Search Report and Written Opinion received for Application No. PCT/US2017/044214, dated Dec. 1, 2017, 11 Pages.
International Search Report and Written Opinion received for PCT Application No. PCT/US2016/40329, dated Sep. 7, 2016, 18 Pages.
International Search Report and Written Opinion received for PCT Application No. PCT/US2018/043817, dated Oct. 16, 2018, 16 pages.
International Search Report and Written Opinion received for PCT/US2016/040972, dated Sep. 13, 2016, 8 Pages.
Advani et al. (Aug. 2002) "Bcr-Abl Variants: Biological and Clinical Aspects", Leukemia Research, 26(8):713-720.
Ambrogio et al. (Mar. 2016) "Combined Inhibition of DDR1 and Notch Signaling is a Therapeutic Strategy for KRAS-driven Lung Adenocarcinoma", Nature Medicine, 22(3):270-277.
Anastassiadis et al. (2011) "Comprehensive Assay of Kinase Catalytic Activity Reveals Features of Kinase Inhibitor Selectivity", Nature Biotechnology, 29(11):1039-1045 (19 pages).
Apicella et al. (2017) "Dual MET/EGFR Therapy Leads to Complete Response and Resistance Prevention in a MET-Amplified Gastroesophageal Xenopatient Cohort", Oncogene, 36:1200-1210.
Awad et al. (2013) "Acquired Resistance to Crizotinib from a Mutation in CD74-ROS1", The New England Journal of Medicine, 368(25):2395-2401.
Baldanzi et al. (Mar. 2015) "Physiological Signaling and Structure of the HGF Receptor MET", Biomedicines, 3(1):1-31.
Balko et al. (Apr. 13, 2016) "Triple Negative Breast Cancers with Amplification of JAK2 at the 9p24 Loci Demonstrate JAK2-Specific Dependence", Science Translational Medicine, 8(334): 25 pages.
Bardelli et al. (2013) "Amplification of the MET Receptor Drives Resistance to Anti-EGFR Therapies in Colorectal Cancer", Cancer Discovery, 3(6):658-673.
Baxter et al. (2005) "Acquired Mutation of the Tyrosine Kinase JAK2 in Human Myeloproliferative Disorders", Lancet, 365(9464):1054-1061.
Bender et al. (Mar. 2016) "Btk Inhibition Treats TLR7/IFN Driven Murine Lupus", Clinical Immunology, 184:65-77.
Bender et al. (Nov. 2016) "Recurrent MET Fusion Genes Represent a Drug Target in Pediatric Glioblastoma", Nature Medicine, 22:1314-1320.
Berndt et al. (Aug. 2017) "Advances of Small Molecule Targeting of Kinases", Current Opinion in Chemical Biology, 39:126-132.
Bertotti et al. (Aug. 2010) "Inhibition of Src Impairs the Growth of Met-Addicted Gastric Tumors", Clinical Cancer Research, 16(15):3933-3943.
Bischof et al. (Apr. 1997) "Role of the Nudeophosmin (NPM) Portion of the Non-Hodgkin's Lymphoma-Associated NPM-Anaplastic Lymphoma Kinase Fusion Protein in Oncogenesis", Molecular and Cellular Biology, 17(4):2312-2325.
Boccaccio et al. (Aug. 2006) "Invasive Growth: A MET-driven Genetic Programme for Cancer and Stem Cells", Nature Reviews Cancer, 6(8):637-645.
Bottaro et al. (Feb. 15, 1991) "Identification of the Hepatocyte Growth Factor Receptor as the c-met ProtoOncogene Product", Science, 251(4995):802-804.
Bradley et al. (2017) "Targeting c-MET in Gastrointestinal Tumours: Rationale, Opportunities and Challenges", Nature Reviews Clinical Oncology, 14(9):562-576.

Bromann et al. (2004) "The Interplay between Src Family Kinases and Receptor Tyrosine Kinases", Oncogene, 23 (48):7957-7968.
Buchert et al. (2016) "Targeting JAK Kinase in Solid Tumors: Emerging Opportunities and Challenges", Oncogene, 35:939-951.
Charest et al. (May 2003) "Fusion of FIG to the Receptor Tyrosine Kinase ROS in a Glioblastoma wth an Interstitial Del(6)(Q21q21)", Genes Chromosomes Cancer, 37(1):58-71.
Chiron et al. (2014) "Cell-Cycle Reprogramming for PI3K Inhibition Overrides a Relapse-Specific C4815 BTK Mutation Revealed by Longitudinal Functional Genomics in Mantle Cell Lymphoma", Cancer Discovery, 4(9):1022-1035.
Cooper et al. (1984) "Molecular Cloning of a New Transforming Gene from a Chemically Transformed Human Cell Line", Nature, 311:29-33.
Couronne et al. (Nov. 15) "Activating Mutations in fyn Kinase in Peripheral T-Cell Lymphomas", Blood, 2013, 122(21):4 pages.
Crystal et al. (2014) "Patient-derived Models of Acquired Resistance Can Identify Effective Drug Combinations for Cancer", Science, 346(6216):1480-1486.
Cui et al. (Aug. 3, 2011) "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)", Journal of Medicinal Chemistry, 54(18):6342-6363.
Davies et al. (Aug. 1, 2013) "Molecular Pathways: ROS1 Fusion Proteins in Cancer", Clinical Cancer Research, 19(15):4040-4045.
Di Paolo et al. (Jan. 2011) "Specific Btk Inhibition Suppresses B Cell- and Myeloid Cell-mediated Arthritis", Nature Chemical Biology, 7:41-50.
Dulak et al. (2011) "HGF-independent Potentiation of EGFR Action by c-Met", Oncogene, 30(33):3825-3635.
Elias et al. (2015) "Fyn is an Important Molecule in Cancer Pathogenesis and Drug Resistance", Pharmacological Research, 100:250-254.
Engelman et al. (May 18, 2007) "MET Amplification Leads to Gefitinib Resistance in Lung Cancer by Activating ERBB3 Signaling", Science, 316(5827):1039-1043.
Fujita-Sato et al. (2015) "Enhanced MET Translation and Signaling Sustains K-Ras-Driven Proliferation under Anchorage-Independent Growth Conditions", Cancer Research, 75(14):2851-2862.
Furman et al. (2014) "Ibrutinib Resistance in Chronic Lymphocytic Leukemia", The New England Journal of Medicine, 370(24):2352-2354.
Gainor et al. (2013) "Novel Targets in Non-small Cell Lung Cancer: ROS1 and RET Fusions", Oncologist, 18(7):865-875.
Gao et al. (Mar. 29, 2016) "JAK2 Inhibition Sensitizes Resistant EGFR-mutant Lung Adenocarcinoma to Tyrosine Kinase Inhibitors", Science Signaling, 9(421): ra33(11 pages).
Gargalionis et al. (Jun. 21, 2013) "The Molecular Rationale of Src Inhibition in Colorectal Carcinomas", International Journal of Cancer, 134(9):2019-2029.
Gherardi et al. (2012) "Targeting MET in Cancer: Rationale and Progress", Nature Reviews Cancer, 12(2):89-103.
Ghiso et al. (Aug. 2013) "Targeting MET: why, where and how?", Current Opinion in Pharmacology, 13(4):511-518.
Golubovskaya et al. (2014) "Targeting FAK in Human Cancer: From Finding to First Clinical Trials", Frontiers in Bioscience (Landmark Ed), 19:687-706 (30 pages).
Gottesman Michael M. (2002) "Mechanisms of Cancer Drug Resistance", Annual Review of Medicine, 53:615-627.
Grande et al. (2011) "Targeting Oncogenic ALK: A Promising Strategy for Cancer Treatment", Molecular Cancer Therapeutics, 10:569-579.
Gridelli et al. (Mar. 2014) "ALK inhibitors in the treatment of advanced NSCLC", Cancer Treatment Reviews, 40(2):300-306.
Pennacchietti et al. (Nov. 2014) "Microenvironment-Derived HGF Overcomes Genetically Determined Sensitivity to Anti-MET Drugs", Cancer Research, 74(22): 6598-6609.
Pesu et al. (Jul. 2008) "Therapeutic Targeting of Janus Kinases", Immunological Reviews, 223(1):132-142.
Peterson et al. (2006) "Expanding the Scope of Crystal Form Evaluation in Pharmaceutical Science", Journal of Pharmacy and Pharmaceutical Sciences, 9(3):317-326.

(56) References Cited

OTHER PUBLICATIONS

Pierotti et al. (Jan. 2006) "Oncogenic Rearrangements of the NTRK1/NGF Receptor", Cancer Letters, 232(1):90-98.
Pilotto et al. (Jan. 2017) "MET Exon 14 Juxtamembrane Splicing Mutations: Clinical and Therapeutical Perspectives for Cancer Therapy", Annals of Translational Medicine, 5(1):11 pages.
Politi et al. (2014) "Perfect ALKemy: Optimizing the Use of ALK-Directed Therapies in Lung Cancer", Clinical Cancer Research, 20(22):5576-5578.
Pulford et al. (2004) "Oncogenic Protein Tyrosine Kinases", Cellular and Molecular Life Sciences CMLS, 61:2939-2953.
Quintás-Cardama et al. (Feb. 2011) "Janus Kinase Inhibitors for the Treatment of Myeloproliferative Neoplasias and Beyond", Nature Reviews Drug Discovery, 10(2):127-140.
Quintás-Cardama et al. (2010) "Preclinical Characterization of the Selective JAK1/2 Inhibitor INCB018424: Therapeutic Implications for the Treatment of Myeloproliferative Neoplasms", Blood, 115(15):3109-3117.
Rahal (Apr. 18, 2016) "The Development of Potent and Selective RET Inhibitors", Presentation at Annual AACR Meeting, 76(Suppl 14):14 pages.
Ravi et al. (2011) "Treatment of Tenosynovial Giant Cell Tumor and Pigmented Villonodular Synovitis", Current Opinion in Oncology, 23(4):361-366.
Reiter et al. (Apr. 1, 2005) "The t(8;9)(p22;p24) Is a Recurrent Abnormality in Chronic and Acute Leukemia that Fuses PCM1 to JAK2", Cancer Research, 65(7):2662-2667.
Ries et al. (2014) "Targeting Tumor-Associated Macrophages with Anti-CSF-1R Antibody Reveals a Strategy for Cancer Therapy", Cancer Cell, 25(6):846-859.
Rudd et al. (2014) "Mutational Analysis of the Tyrosine Kinome in Serous and Clear Cell Endometrial Cancer Uncovers Rare Somatic Mutations in TNK2 and DDR1", BMC Cancer, 884(14):9 pages.
Sancier et al. (2011) "Specific Oncogenic Activity of the Src-Family Tyrosine Kinase c-Yes in Colon Carcinoma Cells", PLoS One, 6(2):e17237:10 Pages.
Sawyers Charles (Nov. 18, 2004) "Targeted Cancer Therapy", Nature, 432(7015):294-297.
Schiller et al. (Jan. 10, 2002) "Comparison of Four Chemotherapy Regimens for Advanced Non-Small-Cell Lung Cancer", The New England Journal of Medicine, 346(2):92-98.
Schuchardt et al. (1994) "Defects in the Kidney and Enteric Nervous System of Mice Lacking the Tyrosine Kinase Receptor Ret", Nature, 367:380-383.
Schwarz et al. (2014) "LYN-activating Mutations Mediate Antiestrogen Resistance in Estrogen Receptor-positive Breast Cancer", The Journal of Clinical Investigation, 124(12):5490-5502.
Sen et al. (2010) "Distinct Interactions between SRC and MET in Mediating Resistance to SRC Inhibition in Head and Neck Cancer", Clinical Cancer Research, 17:1-11.
Serrels et al. (Sep. 24, 2015) "Nuclear FAK Controls Chemokine Transcription, Tregs, and Evasion of Anti-tumor Immunity", Cell, 163(1):160-173.
Shaw et al. (Nov. 20, 2014) "Crizotinib in ROS1-Rearranged Non-Small-Cell Lung Cancer", The New England Journal of Medicine, 371(21):1963-1971.
Shi et al. (2014) "MiR-204 Inhibits Human NSCLC Metastasis Through Suppression of NUAK1", British Journal of Cancer, 111(12):2316-2327.
Smolen et al. (2006) "Amplification of MET may Identify a Subset of Cancers with Extreme Sensitivity to the Selective Tyrosine Kinase Inhibitor PHA-665752", Proceedings of the National Academy of Sciences, 103(7):2316-2321.
Soda et al. (Aug. 2, 2007) "Identification of the Transforming EML4-ALK Fusion Gene in Non-small-cell Lung Cancer", Nature, 448(7153):561-566.
Sonbol et al. (2013) "Comprehensive Review of JAK Inhibitors in Myeloproliferative Neoplasms", Therapeutic Advances in Hematology, 4(1):15-35.
Song et al. (2014) "Cetuximab-Induced MET Activation Acts as a Novel Resistance Mechanism in Colon Cancer Cells", International Journal of Molecular Sciences, 15(4):5838-5851.
Song et al. (Aug. 2017)"Dual Inhibition of MET and SRC Kinase Activity as a Combined Targeting Strategy for Colon Cancer", Experimental and Therapeutic Medicine, 14(2):1357-1366.
Stabile et al. (2012) "C-Src Activation Mediates Erlotinib Resistance in Head and Neck Cancer by Stimulating Met", Clinical Cancer Research, 19:1-13.
Stanley et al. (Jun. 21, 2017) "Synergistic Effects of Various Her Inhibitors in Combination with IGF-1R, C-MET and Src Targeting Agents in Breast Cancer Cell Lines", Scientific Reports, 7(1):1-15.
Stransky et al. (2014) "The Landscape of Kinase Fusions in Cancer", Nature Communications, 4846(5):10 pages.
Straussman et al. (2012) "Tumour Micro-environment Elicits Innate Resistance to RAF Inhibitors through HGF Secretion" , Nature, 487(7408):500-504.
Summy et al. (2003) "Src Family Kinases in Tumor Progression and Metastasis", Cancer and Metastasis Reviews, 22(4):337-358.
Takahashi et al. (Sep. 1, 1985) "Activation of a Novel Human Transforming Gene, ret, by DNA Rearrangement", Cell, 42(2):581-588.
Takeuchi et al. (Nov. 2012) "RET, ROS1 and ALK Fusions in Lung Cancer", Nature Medicine, 18(3):378-381.
Thiele et al. (Oct. 2009) "On Trk—The TrkB Signal Transduction Pathway is an Increasingly Important Target in Cancer Biology", Clinical Cancer Research, 15(19):5962-5967.
Tomasson et al. (2008) "Somatic Mutations and Germline Sequence Variants in the Expressed Tyrosine Kinase Genes of Patients with De Novo Acute Myeloid Leukemia", Blood, 111(9):4797-4808.
Toso et al. (Oct. 9, 2014) "Enhancing Chemotherapy Efficacy in Pten-deficient Prostate Tumors by Activating the Senescence-associated Antitumor Immunity", Cell Reports, 9(1):75-89.
Trusolino et al. (Dec. 2010) "MET Signalling: Principles and Functions in Development, Organ Regeneration and Cancer", Nature Reviews Molecular Cell Biology, 11(12):834-848.
Uguen et al. (2016) "ROS1 Fusions in Cancer: A Review", Future Oncology, 12(16):1911-1928.
Vainchenker et al. (Aug. 2008) "JAKs in Pathology: Role of Janus Kinases in Hematopoietic Malignancies and Immunodeficiencies", Seminars in Cell & Developmental Biology, 19(4):385-393.
Vaishnavi et al. (2013) "Oncogenic and Drug-Sensitive NTRK1 Rearrangements in Lung Cancer", Nature Medicine, 19(11):1469-1472.
Vaishnavi et al. (2015) "TRKing Down an Old Oncogene in a New era of Targeted Therapy", Cancer Discovery, 5(1):25-34(19 pages).
Vergani et al. (Dec. 2011) "Identification of MET and SRC Activation in Melanoma Cell Lines Showing Primary Resistance to PLX4032", Neoplasia, 13(12):1132-1142.
Verma et al. (Oct. 2011) "Targeting Axl and Mer Kinases in Cancer", Molecular Cancer Therapeutics, 10(10):1763-1773.
Verstovsek et al. (2012) "A Double-Blind, Placebo-Controlled Trial of Ruxolitinib for Myelofibrosis", The New England Journal of Medicine, 366(9):799-807.
Vetrie et al. (1993) "The Gene Involved in X-Linked Agammaglobulinaemia is a Member of the Src Family of Protein-Tyrosine Kinases", Nature, 361:226-233.
Voena et al. (Apr. 23, 2016) "Oncogenic ALK Regulates EMT in Non-Small Cell Lung Carcinoma through Repression of the Epithelial Splicing Regulatory Protein 1", Oncotarget, 7(22):33316-33330.
Wiesner et al. (Oct. 15, 2015) "Alternative Transcription Initiation Leads to Expression of a Novel ALK Isoform in Cancer", Nature, 526(7573):453-457.
Wilson et al. (Dec. 1, 2012) "Widespread Potential for Growth-Factor-Driven Resistance to Anticancer Kinase Inhibitors", Nature, 487(7408):505-509.
Grieco et al. (1990) "PTC is a Novel Rearranged form of the ret Proto-Oncogene and is Frequently Detected In Vivo in Human Thyroid Papillary Carcinomas", Cell, 60(4):557-563.
Gu et al. (Jan. 2011) "Survey of Tyrosine Kinase Signaling Reveals ROS Kinase Fusions in Human Cholangiocarcinoma", PLoS ONE, 6(1):9 pages.

(56) References Cited

OTHER PUBLICATIONS

Gunderson et al. (Mar. 2016) "Bruton Tyrosine Kinase-Dependent Immune Cell Cross-talk Drives Pancreas Cancer", Cancer Discovery, 6(3):270-285.
Hackam et al. (Oct. 11, 2006) "Translation of Research Evidence From Animals to Humans", JAMA, 296(14):1731-1732.
Halland et al. (Feb. 13, 2014) "Small Macrocydes as Highly Active Integrin α2β1 Antagonists", ACS Medicinal Chemistry Letters, 5(2):193-198.
Hammerman et al. (2011) "Mutations in the DDR2 Kinase Gene Identify a Novel Therapeutic Target in Squamous Cell Lung Cancer", Cancer Discovery, 1(1):78-89 (12 pages).
Harbinski et al. (2012) "Rescue Screens with Secreted Proteins Reveal Compensatory Potential of Receptor Tyrosine Kinases in Driving Cancer Growth", Cancer Discovery, 2(10):948-959.
Heynen et al. (Dec. 15, 2014) "Resistance to Targeted Cancer Drugs through Hepatocyte Growth Factor Signaling", Cell Cycle, 13(24):3808-3817.
James et al. (2005) "A Unique Clonal JAK2 Mutation Leading to Constitutive Signalling Causes Polycythaemia Vera", Nature, 434(7037):1144-1148.
Jiang et al. (Aug. 2016) "Targeting Focal Adhesion Kinase Renders Pancreatic Cancers Responsive to Checkpoint Immunotherapy", Nature Medicine, 22(8):851-860.
Johnson et al. (Jun. 12, 2014) "Discovery of (10R)-7-Amino-12-fluoro-2,10, 16-Irimethyl-15-0xo-10, 15, 16, 17-tetrahydro-2H-8,4-6 methane )pyrazolo[4,3-h][2,5, 11 ]-benzoxadiazacycloletradecine-3-carbonilrile (PF-06463922), a Macrocydic Inhibitor Jf Anaplastic Lymphoma Kinase (ALK) an", Journal of Medicinal Chemistry, 57(11):4720-4744.
Jordan Craig V. (Mar. 2003) "Tamoxifen: A Most Unlikely Pioneering Medicine", Nature Reviews Drug Discovery, 2(3):205-213.
Katayama et al. (Feb. 2012) "Mechanisms of Acquired Crizotinib Resistance in ALK-rearranged Lung Cancers", Science Translational Medicine, 4(120):25 Pages.
Katayama Ryohei (Sep. 2017) "Therapeutic Strategies and Mechanisms of Drug Resistance in Anaplastic Lymphoma Kinase (ALK)-Rearranged Lung Cancer", Pharmacology & Therapeutics, 177:37 pages.
Kato et al. (Apr. 15, 2017) "RET Aberrations in Diverse Cancers: Next-Generation Sequencing of 4,871 Patients", Clinical Cancer Research, 23(8):1988-1997.
Kentsis et al. (2012) "Autocrine Activation of the MET Receptor Tyrosine Kinase in Acute Myeloid Leukemia", Nature Medicine, 18(7):1118-1122.
Kiselyov Alexander S. (Apr. 2005) "Solid Support Synthesis of 15-Membered Macrocydes Containing a Serotonin Unit", Tetrahedron Letters, 46(17):3007-3010.
Ko et al. (Jan. 2017) "MET/HGF Pathway Activation as a Paradigm of Resistance to Targeted Therapies", Annals of Translational Medicine, 5(1):4.
Kralovics et al. (Apr. 2005) "A Gain-of-function Mutation of JAK2 in Myeloproliferative Disorders", The New England Journal of Medicine, 352(17):1779-1790.
Lacronique et al. (1997) "A TEL-JAK2 Fusion Protein with Constitutive Kinase Activity in Human Leukemia", Science, 278(5341):1309-1312.
Lafave et al. (2012) "JAK2 The Future: Therapeutic Strategies for JAK-Dependent Malignancies", Trends in Pharmacological Sciences, 33(11):574-582.
Levine et al. (Apr. 2005) "Activating Mutation in the Tyrosine Kinase JAK2 in Polycythemia Vera, Essential Thrombocythemia, and Myeloid Metaplasia with Myelofibrosis", Cancer Cell, 7(4):387-397.
Lin et al. (Feb. 2017) 'Targeting ALK: Precision Medicine Takes on Drug Resistance, Cancer Discovery, 7(2):137-155.
Liu et al. (Jul. 2004) "Antiproliferative Effects of Src Inhibition on Medullary Thyroid Cancer", The Journal of Clinical Endocrinology & Metabolism, 89(7):3503-3509.
Liu et al. (2012) "Deregulated MYC Expression Induces Dependence Upon AMPK-Related Kinase 5", Nature, 483:608-612.
Liu et al. (Sep. 27, 2015) "The Molecular Effect of Metastasis Suppressors on Src Signaling and Tumorigenesis: New Therapeutic Targets", Oncotarget, 6(34):35522-35541.
Ma et al. (2008) "Expression and Mutational Analysis of MET in Human Solid Cancers", Genes Chromosomes Cancer, 47(12):1025-1037 (23 pages).
Manning et al. (Dec. 6, 2002) "The Protein Kinase Complement of the Human Genome", Science, 298(5600):1912-1934.
Maulik et al. (2002) "Role of the Hepatocyte Growth Factor Receptor, c-Met, in Oncogenesis and Potential for Therapeutic Inhibition", Cytokine & Growth Factor Reviews, 13(1):41-59.
McCarthy et al. {Jul. 2014, e-Pub (May 8, 2014)} "Tropomyosin Receptor Kinase Inhibitors: A Patent Update 2009-2013", Expert Opinion on Therapeutic Patents, 24(7):731-744.
Miller et al. (2007) "Solvent Systems for Crystallization and Polymorph Selection", Solvent Systems and Their Selection in Pharmaceutics and Biopharmaceutics, 53-109.
Mohamed et al. (2009) "Bruton's Tyrosine Kinase (Btk): Function, Regulation, and Transformation with Special Emphasis on the PH Domain", Immunological Reviews, 228(1):58-73.
Monti Elena (2007) "Molecular Determinants of Intrinsic Multidrug Resistance in Cancer Cells and Tumors", Cancer Drug Resistance, 241-260.
Morgillo et al. (2016) "Mechanisms of Resistance to EGFR-Targeted Drugs: Lung Cancer", ESMO Open, 1(3):e000060:9 Pages.
Morris et al. (1994) "Fusion of a Kinase Gene, ALK, to a Nucleolar Protein Gene, NPM, in Non-Hodgkin's Lymphoma", Science, 263(5151):1281-1284.
Mossé et al. (Oct. 16, 2008) "Identification of ALK as a Major Familial Neuroblastoma Predisposition Gene", Nature, 455(7215):930-935 (20 pages).
Müller et al. (Nov. 11, 1993) "The Protein Tyrosine Kinase JAK1 Complements Defects in Interferon-alpha/beta and -gamma Signal Transduction", Nature, 366(6451):129-135.
Mulligan Lois M. (2014) "RET Revisited: Expanding the Oncogenic Portfolio", Nature Reviews Cancer, 14(3):173-186.
Murray Peter J. (2007) "The JAK-STAT Signaling Pathway: Input and Output Integration", Journal of Immunology, 178(5):2623-2629.
Nefedova et al. (Oct. 15, 2005) "Regulation of Dendrite Cell Differentiation and Antitumor Immune Response in Cancer by Pharmacologic-Selective Inhibition of the Janus-Activated Kinase 2/signal Transducers and Activators of Transcription 3 Pathway", Cancer Research, 65(20):9525-9535.
Neubauer et al. (May 1998) "Jak2 Deficiency Defines an Essential Developmental Checkpoint in Definitive Hematopoiesis", Cell, 93(3):397-409.
Nosaka et al. (Jan. 1, 1995) "Defective Lymphoid Development in Mice Lacking Jak3", Biochemistry, Molecular Biology, and Biophysics (CBS), 270(5237):800-802.
Okamoto et al. (May 2010) "Identification of c-Src as a Potential Therapeutic Target for Gastric Cancer and of Met Activation as a Cause of Resistance to c-Src Inhibition", Molecular Cancer Therapeutics, 9(5):1188-1197.
Ongusaha et al. (2003) "P53 Induction and Activation of DDR1 Kinase Counteract P53-Mediated Apoptosis and Influence P53 Regulation through a Positive Feedback Loop", The EMBO Journal, 22(6):1289-1301.
Otsuka et al. (Nov. 15, 1998) "c-Met Autocrine Activation Induces Development of Malignant Melanoma and Acquisition of the Metastatic Phenotype1", Cancer Research, 58:5157-5167.
Pachnis et al. (1993) "Expression of the c-ret Proto-oncogene during Mouse Embryogenesis", Development, 119:1005-1017.
Pachter et al. (Feb. 1, 1961) "The Chemistry of Hortiamine and 6-Methoxyrhetsinine1", Journal of the American Chemical Society, 83(3):635-642.
Park et al. (2014) "CRIPTO1 Expression in EGFR-mutant NSCLC Elicits Intrinsic EGFR-inhibitor Resistance", The Journal of Clinical Investigation, 124(7):3003-3015.
Park et al. (Jun. 20, 1986) "Mechanism of Met Oncogene Activation", Cell, 45(8):895-904.

(56) References Cited

OTHER PUBLICATIONS

Parsons et al. (2004) "Src Family Kinases, Key Regulators of Signal Transduction", Oncogene, 23:7906-7909.

Wojcik et al. (2006) "A Novel Activating Function of c-Src and Stat3 on HGF Transcription in Mammary Carcinoma Cells", Oncogene, 25(19):2773-2784.

Woyach et al. (2014) "Resistance Mechanisms for the Bruton's Tyrosine Kinase Inhibitor Ibrutinib", The New England Journal of Medicine, 370(24):2286-2294.

Wrobel et al. (2004) "Autocrine CSF-1R Activation Promotes Src-dependent Disruption of Mammary Epithelial Architecture", Journal of Cell Biology, 165(2):263-273.

Xie et al. (Jan. 10, 2012) "Hepatocyte Growth Factor (HGF) Autocrine Activation Predicts Sensitivity to MET Inhibition in Glioblastoma", Proceedings of the National Academy of Sciences, 109(2):570-575.

Xu et al. (2016) "ARK5 Promotes Doxorubicin Resistance in Hepatocellular Carcinoma via Epithelial-mesenchymal Transition", Cancer Letters, 377(2):140-148.

Yang et al. (Feb. 28, 2017) "Tumor-Associated Macrophages: From Basic Research to Clinical Application", Journal of Hematology & Oncology, 10(58):12 Pages.

Yano et al. (2008) "Hepatocyte Growth Factor Induces Gefitinib Resistance of Lung Adenocarcinoma with Epidermal Growth Factor Receptor-activating Mutations", Cancer Research, 68(22):9479-9487.

Yu et al. (2010) "An Integrated Network of Androgen Receptor, Polycomb, and TMPRSS2-ERG Gene Fusions in Prostate Cancer Progression", Cancer Cell, 17(5):443-454.

Yu et al. (Apr. 2013) "Analysis of Tumor Specimens at the Time of Acquired Resistance to EGFR-TKI Therapy in 155 Patients with EGFR-Mutant Lung Cancers", Clinical Cancer Research, 19(8):2240-2247.

Yurovskaya et al. (Apr. 2011) "Some Aspects of the Relationship Between Chirality and Biological Activity", Advances in Synthesis and Complexation. Materials of the All-Russian Scientific Conference, 19-20.

Zardan et al. (2014) "Lyn Tyrosine Kinase Regulates Androgen Receptor Expression and Activity in Castrate-resistant Prostate Cancer", Oncogenesis e115, 3:10 pages.

Zhang et al. (Jul. 1, 2012) "Activation of the AXL Kinase Causes Resistance to EGFR-Targeted Therapy in Lung Cancer", Nature Genetics, 44(8):852-860.

Zhang et al. (2012) "Targeting Src Family Kinases in Anti-Cancer Therapies: Turning Promise into Triumph", Trends in Pharmacological Sciences, 33(3):122-128 (14 pages).

Zou et al. (2007) "An Orally Available Small-Molecule Inhibitor of C-Met, PF-2341066, Exhibits Cytoreductive Antitumor Efficacy through Anti Proliferative and Antiangiogenic Mechanisms", Cancer Research, 67(9):4408-4417.

Zou et al. (Mar. 17, 2015) "PF-06463922 is a Potent and Selective Next-Generation Ros1/Alk Inhibitor Capable of Blocking Crizolinibesislanl Ros1 Mutations", Proceedings of the National Academy of Sciences, 112(11):3493-3498.

\* cited by examiner

MACROCYCLIC COMPOUNDS AND USES THEREOF

CROSS-REFERENCE TO RELATED APPLICATIONS

This application is a continuation application of U.S. application Ser. No. 16/634,289 filed Jan. 27, 2020, which is a national stage entry, filed under 35 USC § 371, of International Application Number PCT/US2018/043817 filed Jul. 26, 2018, which claims priority under 35 U.S.C. § 119(e) to U.S. Provisional Application Ser. No. 62/538,193 filed on Jul. 28, 2017, and U.S. Provisional Application Ser. No. 62/700,990 filed on Jul. 20, 2018, the entire disclosures of which are incorporated herein by reference.

TECHNICAL FIELD

The present disclosure relates to certain macrocyclic compounds that inhibit SRC and MET, and/or CSF1R, pharmaceutical compositions containing such compounds, and methods of using such compounds to treat cancer.

BACKGROUND

Protein kinases are key regulators for cell growth, proliferation and survival. Genetic and epigenetic alterations accumulate in cancer cells leading to abnormal activation of signal transduction pathways which drive malignant processes. (Manning, G. et al, The protein kinase complement of the human genome. *Science* 2002, 298, 1912-1934). Pharmacological inhibition of these signaling pathways presents promising intervention opportunities for targeted cancer therapies. (Sawyers, C. Targeted cancer therapy. *Nature* 2004, 432, 294-297).

MET, also called hepatocyte growth factor receptor (HGFR), was discovered in 1984 (Cooper, C. S., et al Molecular cloning of a new transforming gene from a chemically transformed human cell line. *Nature* 1984, 311, 29-33). Hepatocyte growth factor (HGF), also known as scatter factor (SF), is the high-affinity natural ligand of MET (Bottaro D P et al. Identification of the hepatocyte growth factor receptor as the c-met proto-oncogene product. *Science*. 1991. 251 (4995), 802-804). The HGF/MET signaling pathway is implicated in invasive growth during embryo development, postnatal organ regeneration, wound healing and tissue regeneration processes. However, the HGF/MET axis is frequently hijacked by cancer cells for tumorigenesis, invasive growth, and metastasis (Boccaccio, C.; Comoglio, P. M. Invasive growth: a MET-driven generic programme for cancer and stem cells. *Nat. Rev. Cancer* 2006, 6, 637-645). Deregulations of MET and/or HGF via activating mutations, gene amplifications, overexpression, and both autocrine or paracrine loop regulation influence cell growth, proliferation, angiogenesis, invasion, survival, and metastasis, leading to tumorigenesis and tumor progression (Ma, P C et al. Expression and mutational analysis of MET in human solid cancers. *Genes Chromosomes Cancer* 2008, 47, 1025-1037). Over-expression of MET and/or HGF has been detected in a large variety of solid tumors such as liver, breast, pancreas, lung, kidney, bladder, ovary, brain, prostate, and many others, and is often associated with a metastatic phenotype and poor prognosis (Maulik, G., et al. Role of the hepatocyte growth factor receptor, MET, in oncogenesis and potential for therapeutic inhibition. *Cytokine Growth Factor Rev.* 2002, 13, 41-59). MET amplification has been reported in different human cancers including gastroesophageal carcinomas, colorectal cancers, NSCLC, medulloblastomas, and glioblastomas (Smolen, G. A., et al. Amplification of MET may identify a subset of cancers with extreme sensitivity to the selective tyrosine kinase inhibitor PHA-665752. *Proc. Natl. Acad. Sci. U.S.A* 2006, 103, 2316-2321). A diverse set of MET mutations in the tyrosine kinase domain, juxtamembrane, and extracellular domain of both germline and somatic mutations have been described in many solid tumors, including hereditary and sporadic human papillary renal carcinomas, lung cancer, ovarian cancer, childhood hepatocellular carcinomas, squamous cell carcinoma of the head and neck, and gastric cancer (Ghiso, E.; Giordano, S. Targeting MET: why, where and how? *Curr. Opin. Pharmacol.* 2013, 13, 511-518). MET exon 14 deletion represents a novel class of actionable oncogenic event with potential clinical impact and therapeutic applications in patients affected by different cancer types (Pilotto S, MET exon 14 juxtamembrane splicing mutations: clinical and therapeutical perspectives for cancer therapy. *Ann Transl Med.* 2017 5(1):2). Autocrine or paracrine stimulation is one mechanism for aberrant MET activation. The MET autocrine activation plays a causal role in the development of malignant melanoma and acquisition of the metastatic phenotype (Otsuka, T., et al. MET autocrine activation induces development of malignant melanoma and acquisition of the metastatic phenotype. *Cancer Res.* 1998, 58, 5157-5167). For glioblastoma (GBM), HGF autocrine expression correlated with MET phosphorylation levels in HGF autocrine cell lines, and showed high sensitivity to MET inhibition in vivo, while an HGF paracrine environment could enhance glioblastoma growth in vivo but did not demonstrated sensitivity to MET inhibition (Xie, Q., et al. Hepatocyte growth factor (HGF) autocrine activation predicts sensitivity to MET inhibition in glioblastoma. *Proc. Natl. Acad. Sci. U.S.A* 2012, 109, 570-575). The aberrant expression of HGF is a crucial element in AML pathogenesis that leads to autocrine activation of MET in nearly half of the AML cell lines and clinical samples (Kentsis, A., et al. Autocrine activation of the MET receptor tyrosine kinase in acute myeloid leukemia. *Nat. Med.* 2012, 18, 1118-1122).

Upregulation of HGF/MET signaling has been frequently reported as compensatory signaling to confer resistance for kinase targeted therapies. MET amplification has been detected in 4%-20% of NSCLC patients with the EGFR mutations who acquired resistance to gefitinib or erlotinib treatment (Sequist, L. V., et al. Analysis of tumor specimens at the time of acquired resistance to EGFR-TKI therapy in 155 patients with EGFR-mutant lung cancers. *Clin. Cancer Res.* 2013, 19, 2240-2247). Upregulation of ligand HGF represents another mechanism of EGFR-TKI resistance. High HGF expression was discovered among clinical specimens with acquired resistance that did not have a T790M mutation or MET amplification as well as among cases that exhibited primary resistance despite having EGFR-TKI sensitive activating EGFR gene mutations (Yano, S., et al. Hepatocyte growth factor induces gefitinib resistance of lung adenocarcinoma with epidermal growth factor receptor-activating mutations. *Cancer Res.* 2008, 68, 9479-9487). Amplification of MET is associated with acquired resistance to cetuximab or panitumumab in metastatic colorectal cancer patients that do not develop KRAS mutations during anti-EGFR therapy (Bardelli, A., et al. Amplification of the MET Receptor Drives Resistance to Anti-EGFR Therapies in Colorectal Cancer. *Cancer Discov.* 2013, 3, 658-673). Growth factor-driven resistance from tumor microenvironment represents a potential common mechanism for anti-cancer kinase inhibitors. The upregulation of stromal HGF confers resistance to the BRAF inhibitor ramurafenib in BRAF-mutant melanoma cells (Straussman, R., et al. Tumour micro-environment elicits innate resistance to RAF inhibitors through HGF secretion. *Nature* 2012, 487, 500-504). It was reported that ligand-mediated activation of alternative receptor tyrosine kinases was observed in cancer cells originally dependent on either MET, FGFR2, or FGFR3, and RTKs from the HER and EGFR families as well as MET compensated for loss of each other (Harbinski, F., et al. Rescue screens with secreted proteins reveal compensatory potential of receptor tyrosine kinases in driving cancer growth. *Cancer Discov.* 2012, 2, 948-959). Therefore, blocking adaptive cellular responses that drive compensatory ligand expression is necessary for achieving optimal and sustained antitumor effects.

Oncogenic K-Ras mutation occurs frequently in cancers, including pancreatic, gastric, and lung cancers. K-Ras mutant cancers are more dependent on K-Ras in anchorage-independent culture conditions than in monolayer culture conditions. Enhanced Met expression and signaling is essential for anchorage-independent growth of K-Ras mutant cancer cells and suggests that pharmacological inhibitors of MET could be effective for K-Ras mutant tumor patients (Fujita-Sato, S., et al. Enhanced MET Translation and Signaling Sustains K-Ras-Driven Proliferation under Anchorage-Independent Growth Conditions. *Cancer Res.* 2015, 75, 2851-2862).

Cytoplasmic tyrosine kinases of the SRC family (SFKs) play important roles in signal transduction induced by a large number of extracellular stimuli including growth factors and integrins (Parsons, S. J., et al. Src family kinases, key regulators of signal transduction. *Oncogene,* 2004, 23, 7906-7909). Elevated expression of the non-receptor tyrosine kinase SRC and/or increased SRC kinase activity has been reported in a wide variety of human cancers, including breast, colon, lung, and head and neck cancers. Increased activation of SRC and STAT3 was reported to be associated with many epithelial cancers and linked to the expression of a number of growth factors such as vascular endothelial growth factor and HGF. SRC and STAT3 can act cooperatively as upstream regulators of HGF expression, resulting in establishment of an HGF autocrine loop, signal amplification, and an invasive phenotype (Wojcik, E. J., et al. A novel activating function of SRC and STAT3 on HGF transcription in mammary carcinoma cells. *Oncogene.* 2006, 25, 2773-84). Therefore, targeting SRC/STAT3-signalling pathway may be an effective for disruption of autocrine HGF loops in cancers. EGFR inhibitors have good response only in EGFR-mutant NSCLC patients. The wildtype EGFR activation of invasive phenotypes rely largely on EGFR-SRC-MET signaling through HGF-independent pathway (Dulak A M, et al. HGF-independent potentiation of EGFR action by MET. *Oncogene.* 2011, 30, 3625-3635). EGFR ligands induce accumulation of activated MET, which begins at 8 h and continues for 48 h, leading to an increase in MET expression and phosphorylation of critical MET tyrosine residues without activation of mitogen-activated protein kinase (MAPK) or AKT. This gene transcription related lateral signaling is associated with prolonged SRC phosphorylation, and the SRC pathway is involved with EGFR to MET communication. Although EGFR is overexpressed in about 90% of head and neck squamous cell carcinoma (HNSCC), EGFR inhibitors developed to-date have been provided limited clinical efficacy. For example, ligand-independent activation of MET contributes specifically to erlotinib resistance in HNSCC with activated SRC, where MET activation is more dependent on SRC than on EGFR, providing an alternate survival pathway (Stabile, L. P., et al. c-SRC activation mediates erlotinib resistance in head and neck cancer by stimulating MET. *Clin Cancer Res.* 2012, 19, 1-13). Aberrant activation of SRC has been demonstrated in numerous epithelial tumors, including HNSCC. SRC inhibition resulted in a universal and profound reduction of invasion and migration of HNSCC cell lines, but produced cytotoxicity in some of HNSCC cell lines. Sustained MET activation mediates resistance to SRC inhibition. The synergistic cytotoxic effects of SRC and MET inhibition were observed in HNCC cell lines (Sen, B., et al. Distinct interactions between SRC and MET in mediating resistance to SRC inhibition in head and neck cancer. *Clin Cancer Res.* 2010, 17, 1-11).

It was reported that cetuximab-induced MET activation led to cetuximab resistance in Caco-2 colon cancer cells, and SRC activation promoted cetuximab resistance by interacting with MET via MET/SRC/EGFR complex formation (Song N, et al. Cetuximab-induced MET activation acts as a novel resistance mechanism in colon cancer cells. *Int J Mol Sci.* 2014, 15, 5838-5851). SRC is a key downstream transducer of MET-driven tumor growth. Inhibition of SRC in Met-addicted gastric carcinoma cell lines enhanced the cell sensitivity to inhibition of MET that supports the therapeutic potential of combinatorial treatment with MET and SRC inhibitors (Bertotti, A., et al. Inhibition of SRC impairs the growth of MET-addicted gastric tumors. *Clin Cancer Res.* 2010, 16, 3933-3943). Although HGF/MET signaling is implicated in the development of colorectal cancer (CRC), inhibition of MET alone has been demonstrated to have limited efficacy. SRC activation was essential for ligand-dependent and independent activation of MET. The combined inhibition of MET and SRC enhanced the inhibition of cell proliferation and apoptosis in mutant and wild type RAS colon cancer cells (Song, N., et al. Dual inhibition of MET and SRC kinase activity as a combined targeting strategy for colon cancer. *Exp Ther Med* etm.2017.4692).

CSF1R, also known as FMS, is a receptor for colony stimulating factor 1, a cytokine that controls the production, differentiation, and function of macrophages. Non-resolving inflammation in the tumor microenvironment is a hallmark of cancer and associated with M2-polarized macrophages. Tumor associated macrophages (TAMs) more closely resemble M2-polarized macrophages, and play important roles in promoting proliferation, invasion, and metastasis of cancer (Yang L, et al. Tumor-associated macrophages: from basic research to clinical application. *J Hematol Oncol.* 2017, 10, 58). The tumor-promoting function of TAMs is based on their capacity to secrete proangiogenic and growth factors, as well as to potently suppress T cell effector function by releasing immunosuppressive cytokines and affecting their metabolism (Ries C H, et al. Targeting tumor-associated macrophages with anti-CSFR antibody reveals a strategy for cancer therapy. *Cancer Cell.* 2014, 25, 846-859). Although anti-PD-1 monoclonal antibodies (mAbs) targeting the immune checkpoint have demonstrated benefits for the treatment of certain cancers, these drugs are not always effective. Recent studies indicated that the efficacy of anti-PD-1 mAbs was impacted by the uptake of anti-PD-1 mAbs-bound PD-1+ tumor-infiltrating CD8+ T cells by PD-1-tumor-associated macrophages. Combination therapies designed to target tumor macrophages and anti-PD-1, may provide additional benefit by increasing immune checkpoint blockade drug delivery to CD8+ T cells, thereby enhancing activity of immunotherapy (Arlauckas S P, et al. In vivo imaging reveals a tumor-associated macrophage-mediated resistance pathway in anti-PD-1 therapy. *Sci Transl Med.* 2017, 9(389). pii: eaal3604). Survival of TAMs is mediated by signaling through colony-stimulating factor 1 receptor (CSF1R), and inhibition of CSF1R signaling reduces TAMs and increases CD8/CD4 T-cell ratio in patients with advanced solid tumors. Therefore, targeting CSF1R signaling leading to the modulation of TAMs is a promising therapeutic strategy in various solid tumors, as a single agent or in combination with standard of care chemotherapeutic agents and immunotherapies. Coexpression of CSF1R and CSF1 is most often detected in invasive tumors. Autocrine CSF-1R activation induced hyperproliferation and disruption of junctional integrity in acinar structures formed by human mammary epithelial cells in three-dimensional culture through a SRC-dependent mechanism (Wrobel C N, et al. Autocrine CSF1R activation promotes SRC-dependent disruption of mammary epithelial architecture. *J Cell Biol.* 2004, 165, 263-273). Inhibition of CSF-1R and SRC may prove to be a valuable strategy in the treatment of invasive tumors. Tenosynovial giant cell tumor (TGCT) or pigmented villonodular synovitis (PVNS) is a clonal neoplastic proliferation arising from cells overexpressing CSF1 that recruit CSF1R-bearing polyclony macrophages and make up the bulk of the tumor. Inhibition of CSF1R using small molecule inhibitors can lead to improvement in the affected joint (Ravi V, et al. Treatment of tenosynovial giant cell tumor and pigmented villonodular synovitis. *Curr Opin Oncol.* 2011, 23, 361-366).

In a summary, aberrant activation of HGF/MET pathway has frequently been found in human cancers via protein over-expression, mutation, gene amplification, and also paracrine or autocrine upregulation. In addition, the activation of HGF/MET signaling confers resistance to cancer therapies. SRC activation is implicated for ligand-dependent and independent activation of MET. CSF1R plays an import role in regulation of tumor associated macrophage. Therefore, the polypharmacologic inhibition of MET/SRC/CSF1R has great potential for therapeutic interventions in cancers. To-date, compounds that inhibit MET/SRC and/or CSF1R have been elusive. As such, there exists a significant unmet need.

SUMMARY

In one aspect, the disclosure relates to a compound of the Formula I

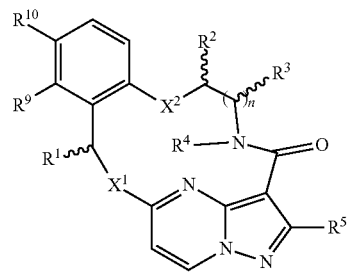

I or a pharmaceutically acceptable salt thereof, wherein
$X^1$ and $X^2$ are independently —$CR^6R^7$—, S, S(O), S(O)$_2$, O or N($R^8$);
$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_3$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O$XC_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^4$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^5$ is H or —$NR^6R^7$;

each $R^6$, $R^7$ and $R^8$ are each independently selected from the group consisting of H, $C_1$-$C_6$ alkyl, $C_2$-$C_6$ alkenyl, $C_2$-$C_6$ alkynyl, and $C_3$-$C_6$ cycloalkyl; wherein each hydrogen atom in $C_1$-$C_6$ alkyl, $C_2$-$C_6$ alkenyl, $C_2$-$C_6$ alkynyl, and $C_3$-$C_6$ cycloalkyl is independently optionally substituted by deuterium, fluoro, chloro, bromo, —OH, —CN, —$OC_1$-$C_6$ alkyl, —$NH_2$, —$NH(C_1$-$C_6$ alkyl), —$N(C_1$-$C_6$ alkyl$)_2$, $C_3$-$C_7$ cycloalkyl, 3- to 7-membered heterocycloalkyl, $C_6$-$C_{10}$ aryl, 5- to 7-membered heteroaryl, —$CO_2H$, —C(O) $OC_1$-$C_6$ alkyl, —$C(O)NH_2$, —$C(O)NH(C_1$-$C_6$ alkyl), or —$C(O)N(C_1$-$C_6$ alkyl$)_2$;

$R^9$ is H, fluoro, chloro, bromo, —CN, —$CF_3$, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$;

$R^{10}$ is H, fluoro, chloro or bromo; and n is 1 or 2;

with the proviso that when $R^5$ is H, $R^9$ is selected from the group consisting of —CN, —$CF_3$, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$.

In another aspect, the disclosure relates to a pharmaceutical composition comprising a compound of the Formula I, or a pharmaceutically acceptable salt thereof, and optionally at least one or more of a pharmaceutically acceptable diluent, carrier or excipient.

In another aspect, the disclosure is directed to a method of treating cancer in a patient comprising, a. administering a therapeutically effective amount of a compound that inhibits SRC and MET, and/or CSF1R. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer.

In another aspect, the disclosure is directed to a method of treating cancer in a patient comprising, a. administering a therapeutically effective amount of a compound that inhibits SRC and MET, and/or CSF1R; and b. administering a therapeutically effective amount of at least one additional anti-cancer agent. In some embodiments of this aspect, the at least one additional anti-cancer agent is an EGFR inhibitor, or a pharmaceutically acceptable salt thereof. In some embodiments of this aspect, the additional anti-cancer agent is an antibody of EGFR. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer.

In another aspect, the disclosure is directed to a compound that inhibits SRC and MET, and/or CSF1R, or a pharmaceutically acceptable salt thereof, for use in the treatment of cancer in a patient. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer.

In another aspect, the disclosure is directed to a compound that inhibits SRC and MET, and/or CSF1R, or a pharmaceutically acceptable salt thereof, in combination with a therapeutically effective amount of at least one additional anti-cancer agent, or a pharmaceutically acceptable salt thereof, for use in the treatment of cancer in a patient. In some embodiments of this aspect, the at least one additional anti-cancer agent is an EGFR inhibitor, or a pharmaceutically acceptable salt thereof. In some embodiments of this aspect, the additional anti-cancer agent is an antibody of EGFR. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer.

In another aspect, the disclosure is directed to use of a compound that inhibits SRC and MET, and/or CSF1R, or a pharmaceutically acceptable salt thereof, for use in the treatment of cancer in a patient. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer. In some embodiments of this aspect, the compound is administered in combination with a therapeutically effective amount of at least one additional anti-cancer agent. In some embodiments of this aspect, the at least one additional anti-cancer agent is an EGFR inhibitor, or a pharmaceutically acceptable salt thereof. In some embodiments of this aspect, the additional anti-cancer agent is an antibody of EGFR.

In another aspect, the disclosure is directed to a composition comprising a compound that inhibits SRC and MET, and/or CSF1R, or a pharmaceutically acceptable salt thereof, in a therapeutically effective amount, for use in the treatment of cancer in a patient. In some embodiments of this aspect, the compound that inhibits SRC and MET, and/or CSF1R is of the Formula I. In some embodiments of this aspect, the cancer is gastric cancer, colon cancer, renal cancer, liver cancer, lung cancer, glioblastoma, or head & neck cancer. In some embodiments of this aspect, the compound is administered in combination with a therapeutically effective amount of at least one additional anti-cancer agent. In some embodiments of this aspect, the at least one additional anti-cancer agent is an EGFR inhibitor, or a pharmaceutically acceptable salt thereof. In some embodiments of this aspect, the additional anti-cancer agent is an antibody of EGFR.

In yet another aspect, the disclosure relates to a synergistic composition of a compound that inhibits SRC and MET, and/or CSF1R, and an EGFR inhibitor, where the two components come into contact with each other at a locus. In some embodiments of this aspect, the compound that inhibits SRC and MET, and/or CSF1R is of the Formula I.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound to of the Formula I

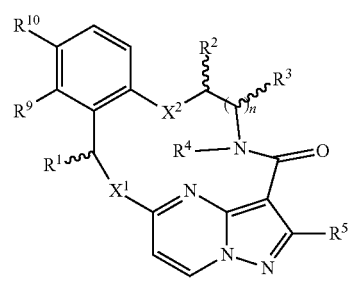

I or a pharmaceutically acceptable salt thereof, wherein $X^1$ and $X^2$ are independently —$CR^6R^7$—, S, S(O), S(O)$_2$, O or N($R^8$);

$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_3$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(OX$C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^4$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^5$ is H or —N$R^6R^7$;

each $R^6$, $R^7$ and $R^8$ are each independently selected from the group consisting of H, $C_1$-$C_6$ alkyl, $C_2$-$C_6$ alkenyl, $C_2$-$C_6$ alkynyl, and $C_3$-$C_6$ cycloalkyl; wherein each hydrogen atom in $C_1$-$C_6$ alkyl, $C_2$-$C_6$ alkenyl, $C_2$-$C_6$ alkynyl, and $C_3$-$C_6$ cycloalkyl is independently optionally substituted by deuterium, fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl), or —C(O)N($C_1$-$C_6$ alkyl)$_2$;

$R^9$ is H, fluoro, chloro, bromo, —CN, —CF$_3$, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$;

$R^{10}$ is H, fluoro, chloro or bromo; and n is 1 or 2;

with the proviso that when $R^5$ is H, $R^9$ is selected from the group consisting of —CN, —CF$_3$, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$.

2. The compound of clause 1, or a pharmaceutically acceptable salt thereof, wherein $R^5$ is H.

3. The compound of clause 2, or a pharmaceutically acceptable salt thereof, wherein $R^9$ is —CN.

4. The compound of any of the preceding clauses, or a pharmaceutically acceptable salt thereof, wherein $R^{10}$ is F.

5. The compound of clause 1, or a pharmaceutically acceptable salt thereof, wherein $R^5$ is —N$R^6R^7$.

6. The compound of clause 5, or a pharmaceutically acceptable salt thereof, wherein $R^6$ and $R^7$ are H.

7. The compound of clause 5, or a pharmaceutically acceptable salt thereof, wherein $R^9$ is —CN.

8. The compound of clause 6, or a pharmaceutically acceptable salt thereof, wherein $R^9$ is —CN.

9. The compound of any one of clauses 5 to 8, or a pharmaceutically acceptable salt thereof, wherein $R^{10}$ is fluoro.

10. The compound of any one of the preceding clauses, or a pharmaceutically acceptable salt thereof, wherein $X^1$ is N($R^8$).

11. The compound of any one of the preceding clauses, or a pharmaceutically acceptable salt thereof, wherein $R^8$ is $C_1$-$C_6$ alkyl, wherein each hydrogen atom is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl), or —C(O)N($C_1$-$C_6$ alkyl)$_2$.

12. The compound of any one of the preceding clauses, or a pharmaceutically acceptable salt thereof, wherein $R^8$ is ethyl, propyl, iso-propyl, or methylcyclopropyl.

13. The compound of any one of the preceding clauses, or a pharmaceutically acceptable salt thereof, wherein $X^2$ is O.

14. The compound of any one of the preceding clauses, or a pharmaceutically acceptable salt thereof, wherein $R^2$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl, and R$^3$ is H.

15. The compound of any one of the preceding clauses, or a pharmaceutically acceptable salt thereof, wherein R$^2$ is C$_1$-C$_6$ alkyl.

16. The compound of any one of the preceding clauses, or a pharmaceutically acceptable salt thereof, wherein R$^2$ is methyl.

17. The compound of any one of clauses 1 to 14, or a pharmaceutically acceptable salt thereof, wherein R$^2$ is H, and R$^3$ is H, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl.

18. The compound of any one of clauses 1 to 14, or a pharmaceutically acceptable salt thereof, wherein R$^2$ and R$^3$ are H.

19. The compound of clause 1, selected from the group consisting of

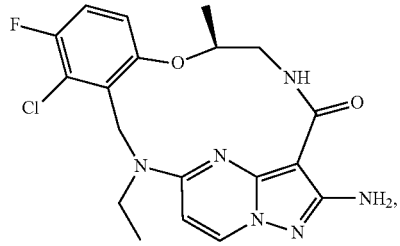

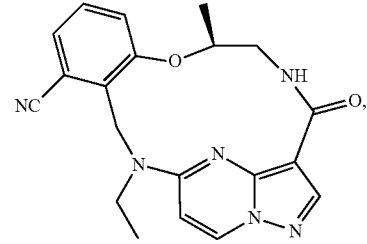

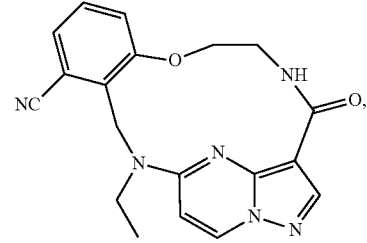

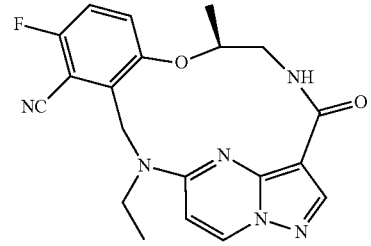

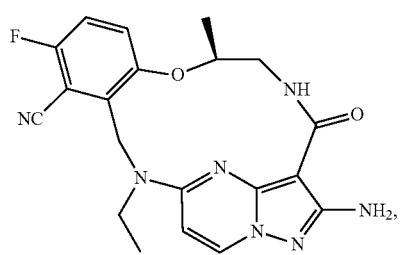

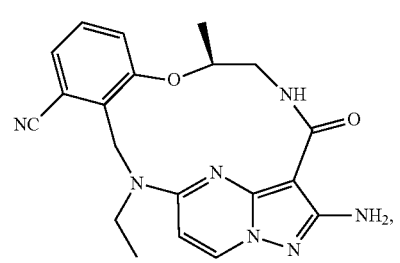

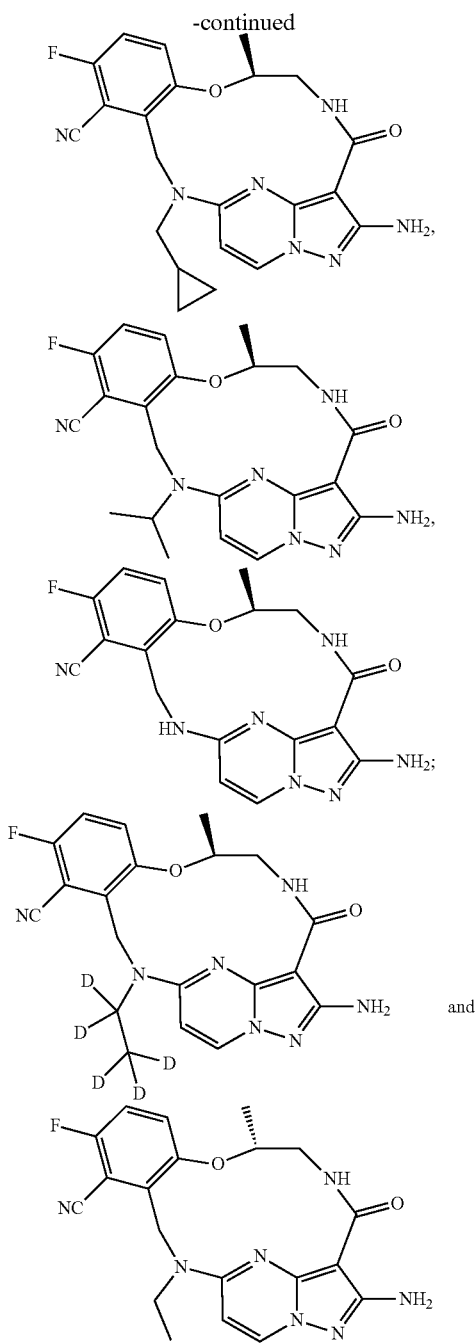

or a pharmaceutically acceptable salt thereof.

20. A pharmaceutical composition comprising a compound of any one of clauses 1 to 19, or a pharmaceutically acceptable salt thereof, and at least one or more of a pharmaceutically acceptable diluent, carrier or excipient.

21. A method of treating cancer in a patient comprising, a. administering a therapeutically effective amount of a compound that inhibits SRC and MET, and/or CSF1R.

22. The method of clause 22, wherein the compound that inhibits SRC and MET, and/or CSF1R is of the formula of any one of clauses 1 to 19.

23. The method of clause 21 or 22, wherein the cancer is gastric cancer, colon cancer, renal cancer, liver cancer, lung cancer, glioblastoma, or head & neck cancer.

24. The method of any one of clauses 21 to 23, further comprising b. administering a therapeutically effective amount of at least one additional anti-cancer agent.

25. The method of clause 24, wherein the at least one additional anti-cancer agent is an EGFR inhibitor, or a pharmaceutically acceptable salt thereof.

26. The method of clause 24, wherein the additional anti-cancer agent is an antibody of EGFR.

27. The method of clause 26, wherein the antibody of EGFR is cetuximab, necitumumab or panitumumab.

28. The method of clause 24, wherein the additional anti-cancer agent is a small molecule inhibitor of EGFR.

29. The method of clause 28, wherein the small molecule inhibitor of EGFR is afatinib, brigatinib, canertinib, dacomitinib, erlotinib, gefitinib, HKI 357, lapatinib, osimertinib, naquotinib, nazartinib, neratinib, olmutinib, pelitinib, PF-06747775, rociletinib, vandetanib, or a pharmaceutically acceptable salt thereof.

30. The method of any one of clauses 24, 28 or 29, wherein the additional anti-cancer agent is gefitinib, or a pharmaceutically acceptable salt thereof.

31. The method of any one of clauses 24, 28 or 29, wherein the additional anti-cancer agent is osimertinib, or a pharmaceutically acceptable salt thereof.

32. The method of any one of clauses 24, 28 or 29, wherein the additional anti-cancer agent is erlotinib, or a pharmaceutically acceptable salt thereof.

33. A compound that inhibits SRC and MET, and/or CSF1R, or a pharmaceutically acceptable salt thereof, for use in the treatment of cancer in a patient.

34. The compound of clause 33, wherein the compound that inhibits SRC and MET, and/or CSF1R is of the formula of any one of clauses 1 to 19.

35. The compound of clause 33 or 34, wherein the cancer is gastric cancer, colon cancer, renal cancer, liver cancer, lung cancer, glioblastoma, or head & neck cancer.

36. The compound of any one of clauses 33 to 35, in combination with a therapeutically effective amount of at least one additional anti-cancer agent.

37. The compound of clause 36, wherein the at least one additional anti-cancer agent is an EGFR inhibitor, or a pharmaceutically acceptable salt thereof.

38. The compound of clause 36, wherein the additional anti-cancer agent is an antibody of EGFR.

39. The compound of clause 38, wherein the antibody of EGFR is cetuximab, necitumumab or panitumumab.

40. The compound of clause 36, wherein the additional anti-cancer agent is a small molecule inhibitor of EGFR.

41. The compound of clause 40, wherein the small molecule inhibitor of EGFR is afatinib, brigatinib, canertinib, dacomitinib, erlotinib, gefitinib, HKI 357, lapatinib, osimertinib, naquotinib, nazartinib, neratinib, olmutinib, pelitinib, PF-06747775, rociletinib, vandetanib, or a pharmaceutically acceptable salt thereof.

42. The compound of anyone of clauses 36, 40 or 41, wherein the additional anti-cancer agent is gefitinib, or a pharmaceutically acceptable salt thereof.

43. The compound of anyone of clauses 36, 40 or 41, wherein the additional anti-cancer agent is osimertinib, or a pharmaceutically acceptable salt thereof.

44. The compound of anyone of clauses 36, 40 or 41, wherein the additional anti-cancer agent is erlotinib, or a pharmaceutically acceptable salt thereof.

45. Use of a compound that inhibits SRC and MET, and/or CSF1R, or a pharmaceutically acceptable salt thereof, in the preparation of a medicament for use in the treatment of cancer.

46. The use of clause 45, wherein the compound that inhibits SRC and MET, and/or CSF1R is of the formula of any one of clauses 1 to 19.

47. The use of clause 45 or 46, wherein the cancer is gastric cancer, colon cancer, renal cancer, liver cancer, lung cancer, glioblastoma, or head & neck cancer.

48. The use of any one of clauses 45 to 47, in combination with a therapeutically effective amount of at least one additional anti-cancer agent.

49. The use of clause 48, wherein the at least one additional anti-cancer agent is an EGFR inhibitor, or a pharmaceutically acceptable salt thereof.

50. The use of clause 48, wherein the additional anti-cancer agent is an antibody of EGFR.

51. The use of clause 50, wherein the antibody of EGFR cetuximab, necitumumab or panitumumab.

52. The use of clause 48, wherein the additional anti-cancer agent is a small molecule inhibitor of EGFR.

53. The use of clause 52, wherein the small molecule inhibitor of EGFR is afatinib, brigatinib, canertinib, dacomitinib, erlotinib, gefitinib, HKI 357, lapatinib, osimertinib, naquotinib, nazartinib, neratinib, olmutinib, pelitinib. PF-06747775, rociletinib, vandetanib, or a pharmaceutically acceptable salt thereof.

54. The use of any one of clauses 48, 52 or 53, wherein the additional anti-cancer agent is gefitinib, or a pharmaceutically acceptable salt thereof.

55. The use of any one of clauses 48, 52 or 53, wherein the additional anti-cancer agent is osimertinib, or a pharmaceutically acceptable salt thereof.

56. The use of any one of clauses 48, 52 or 53, wherein the additional anti-cancer agent is erlotinib, or a pharmaceutically acceptable salt thereof.

57. A composition comprising a compound that inhibits SRC and MET, and/or CSFR, or a pharmaceutically acceptable salt thereof, in a therapeutically effective amount, for use in the treatment of cancer in a patient.

58. The composition of clause 57, wherein the compound that inhibits SRC and MET, and/or CSF1R is of the formula of any one of clauses 1 to 20.

59. The composition of clause 56 or 57, wherein the cancer is gastric cancer, colon cancer, renal cancer, liver cancer, lung cancer, glioblastoma, or head & neck cancer.

60. The composition of any one of clauses 57 to 59, in combination with a therapeutically effective amount of at least one additional anti-cancer agent.

61. The composition of clause 60, wherein the at least one additional anti-cancer agent is an EGFR inhibitor, or a pharmaceutically acceptable salt thereof.

62. The composition of clause 60, wherein the additional anti-cancer agent is an antibody of EGFR.

63. The composition of clause 62, wherein the antibody of EGFR cetuximab, necitumumab or panitumumab.

64. The composition of clause 60, wherein the additional anti-cancer agent is a small molecule inhibitor of EGFR.

65. The composition of clause 64, wherein the small molecule inhibitor of EGFR is afatinib, brigatinib, canertinib, dacomitinib, erlotinib, gefitinib, HKI 357, lapatinib, osimertinib, naquotinib, nazartinib, neratinib, olmutinib, pelitinib, PF-06747775, rociletinib, vandetanib, or a pharmaceutically acceptable salt thereof.

66. The composition of any one of clauses 60, 64 or 65, wherein the additional anti-cancer agent is gefitinib, or a pharmaceutically acceptable salt thereof.

67. The composition of any one of clauses 60, 64 or 65, wherein the additional anti-cancer agent is osimertinib, or a pharmaceutically acceptable salt thereof.

68. The composition of any one of clauses 60, 64 or 65, wherein the additional anti-cancer agent is erlotinib, or a pharmaceutically acceptable salt thereof.

69. A synergistic composition of a compound that inhibits SRC and MET, and/or CSF1R, and an EGFR inhibitor, where the two components come into contact with each other at a locus.

70. The synergistic composition of clause 69, wherein the compound that inhibits SRC and MET, and/or CSF1R is of the formula of any one of clauses 1 to 19.

71. The synergistic composition of clause 69 or 70, wherein the locus is a patient.

72. The synergistic composition of clause 69 or 70, wherein the locus is a cancer.

73. The synergistic composition of clause 72, wherein the cancer is gastric cancer, colon cancer, renal cancer, liver cancer, lung cancer, glioblastoma, or head & neck cancer.

74. The synergistic composition of any one of clauses 69 to 73, wherein the EGFR inhibitor is an antibody of EGFR.

75. The synergistic composition of clause 74, wherein the antibody of EGFR cetuximab, necitumumab or panitumumab.

76. The synergistic composition of any one of clauses 69 to 73, wherein the EGFR inhibitor is a small molecule inhibitor of EGFR.

77. The synergistic composition of clause 76, wherein the small molecule inhibitor of EGFR is afatinib, brigatinib, canertinib, dacomitinib, erlotinib, gefitinib, HKI 357, lapatinib, osimertinib, naquotinib, nazartinib, neratinib, olmutinib, pelitinib, PF-06747775, rociletinib, vandetanib, or pharmaceutically acceptable salts thereof.

78. The synergistic composition of any one of clauses 69-73, 76 or 77, wherein the EGFR inhibitor is gefitinib, or a pharmaceutically acceptable salt thereof.

79. The synergistic composition of any one of clauses 69-73, 76 or 77, wherein the EGFR inhibitor is osimertinib, or a pharmaceutically acceptable salt thereof.

80. The synergistic composition of any one of clauses 69-73, 76 or 77, wherein the EGFR inhibitor is erlotinib, or a pharmaceutically acceptable salt thereof.

(IC$_{50}$: 5 nM (partial), Emax %: 47), (●) Compound 5 (1 μM)+AZD9291 (IC$_{50}$: 2 nM, Emax %: 71).

Figure 4:
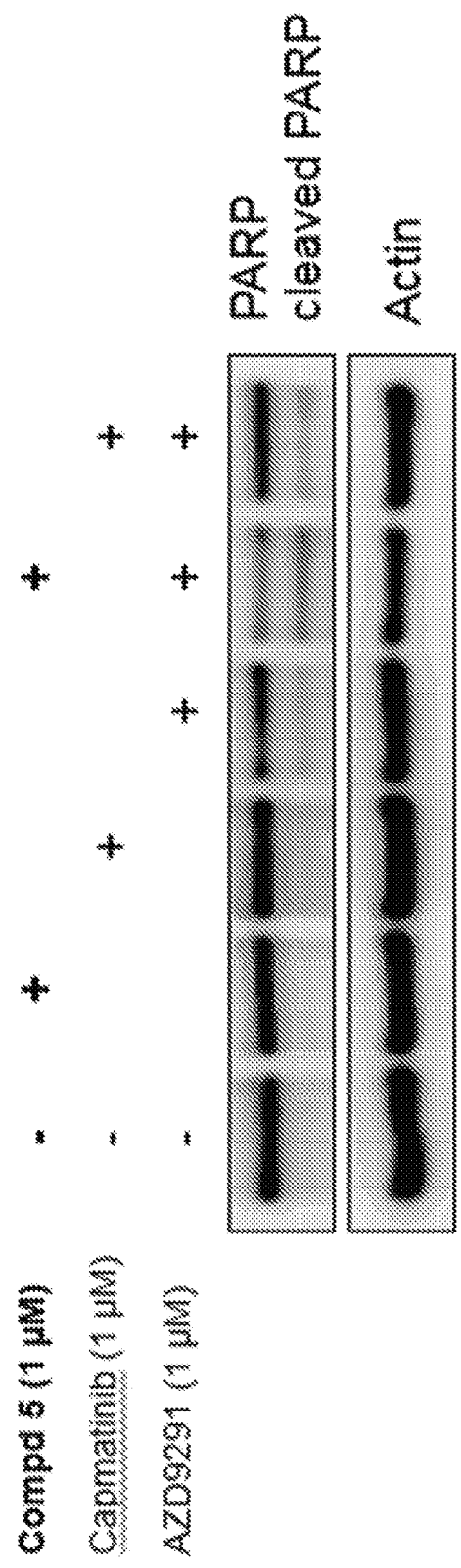

FIG. 4 shows the effects of Compound 5, capmatinib, AZD9291 and combinations on the apoptosis of HCC827 cells after 48 hour incubation. Compound 5 synergized with AZD9291 for apoptosis in HCC827 cell line.

Figure 5:
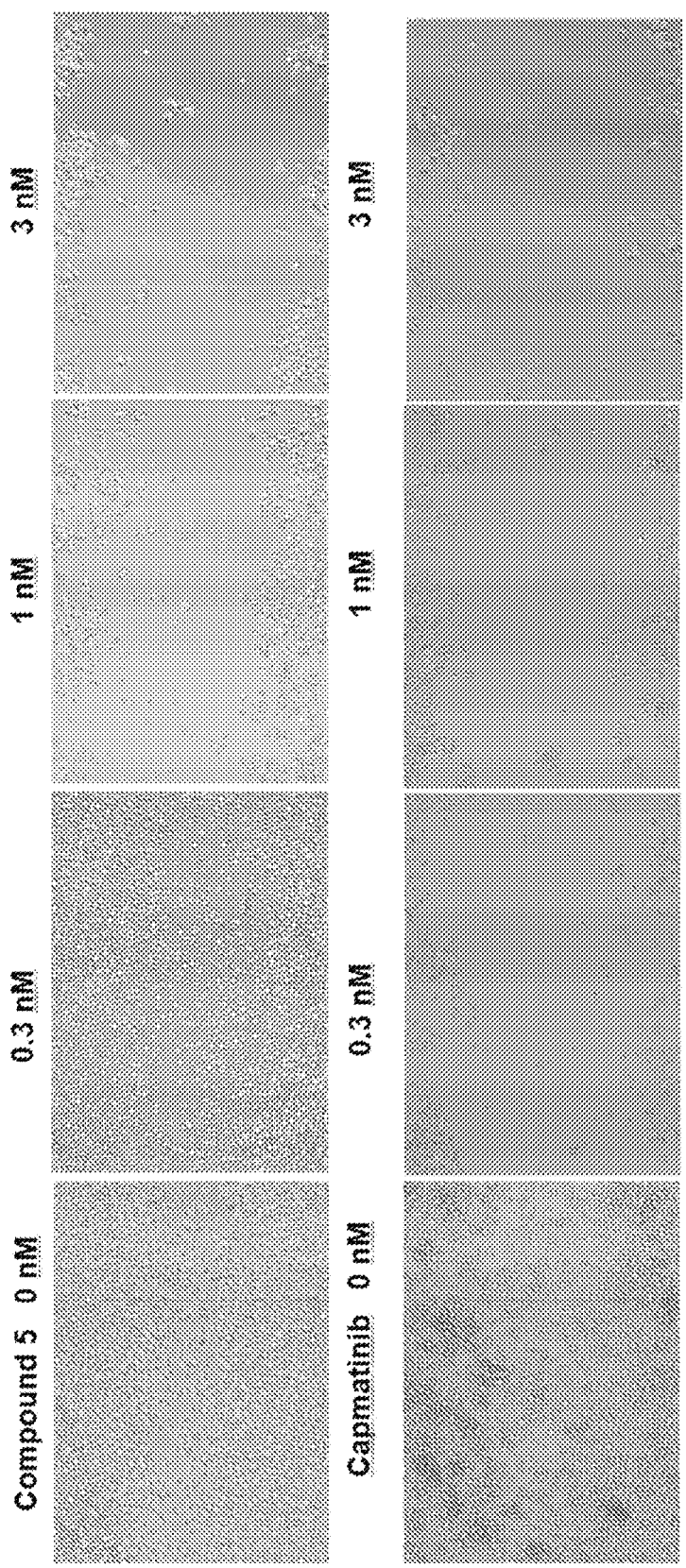

FIG. 5 shows a wound healing assay in which Compound 5 and capmatinib inhibited cell migration of MKN-45 cells.

Figure 6:
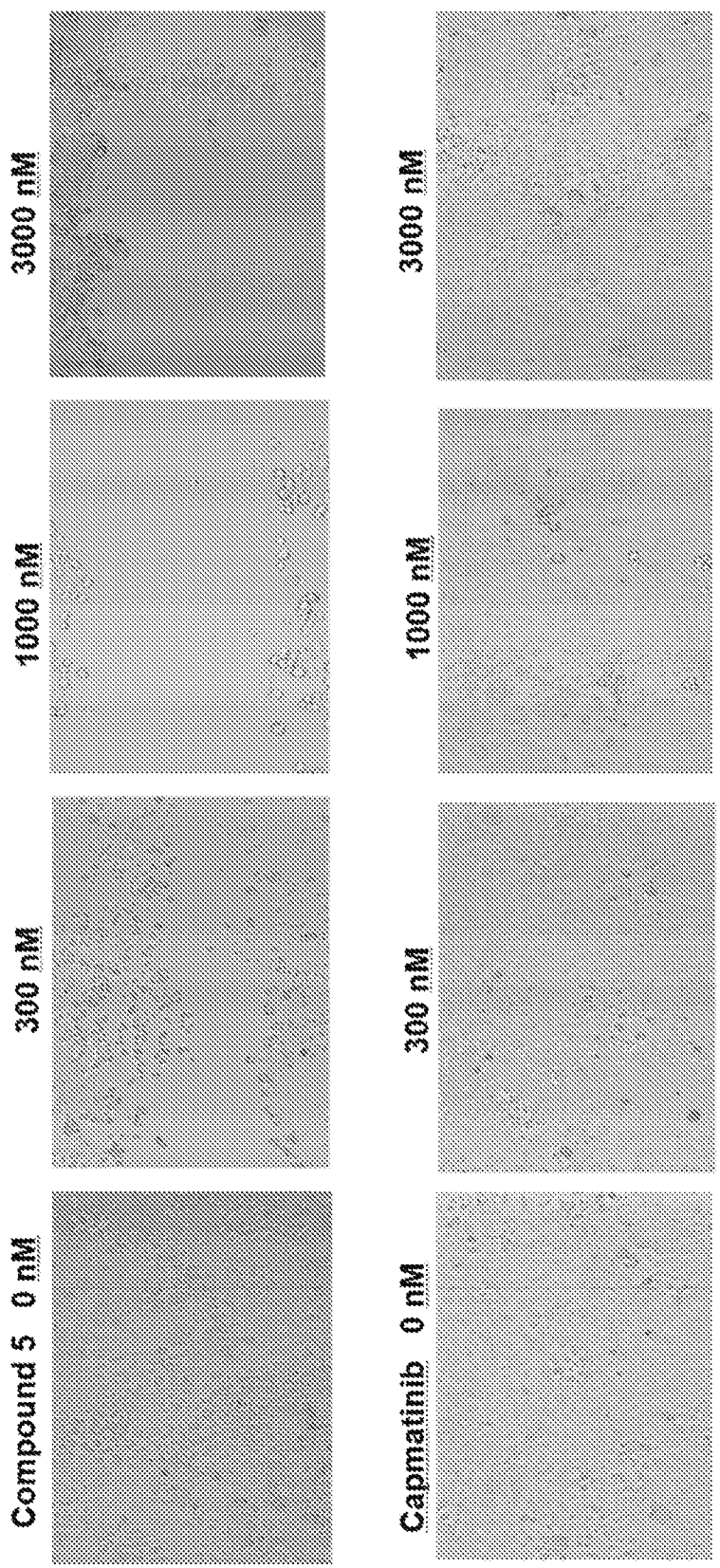

FIG. 6 shows a wound healing assay in which Compound 5 inhibited cell migration of HCC827, and campmatinib showed a minimal effect.

Figure 7:
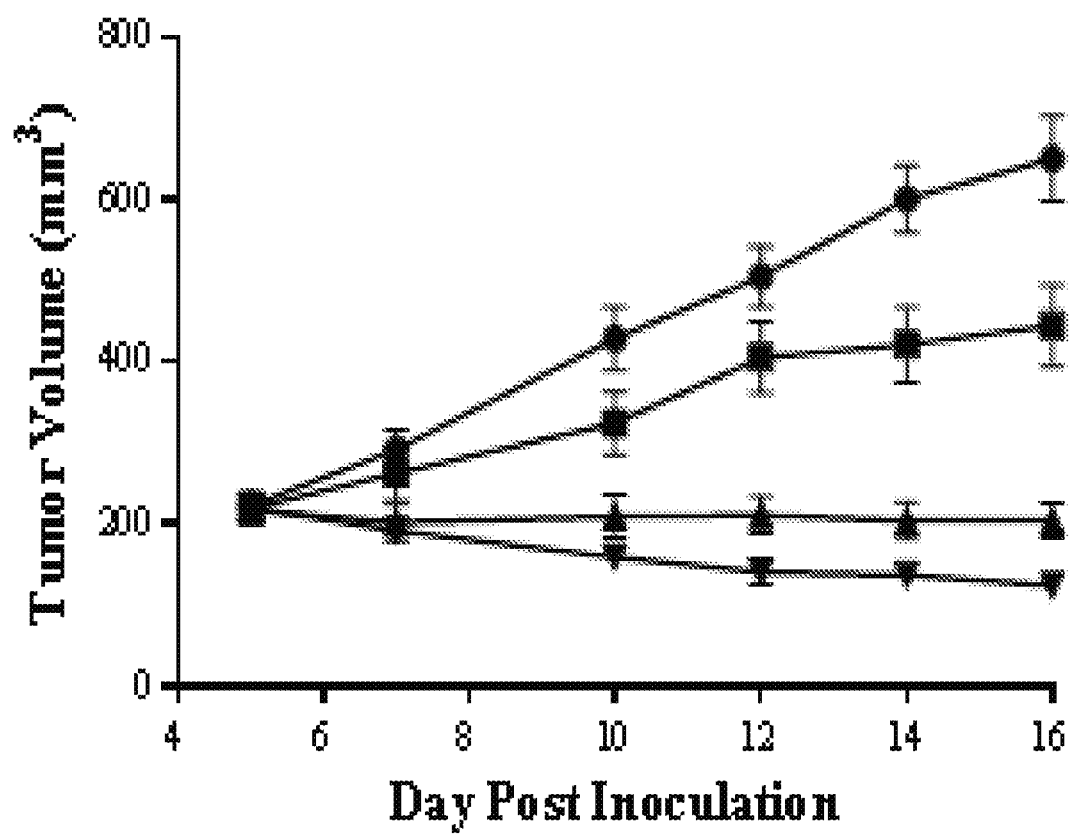

FIG. 7 is a graph showing the effect of Compound 5 on tumor growth in the MKN-45 xenograft model. (●) vehicle, (■) Compound 5 at 3 mg/kg BID, (▲) Compound 5 at 10 mg/kg BID, (▼) Compound 5 at 30 mg/kg BID.

Figure 8:
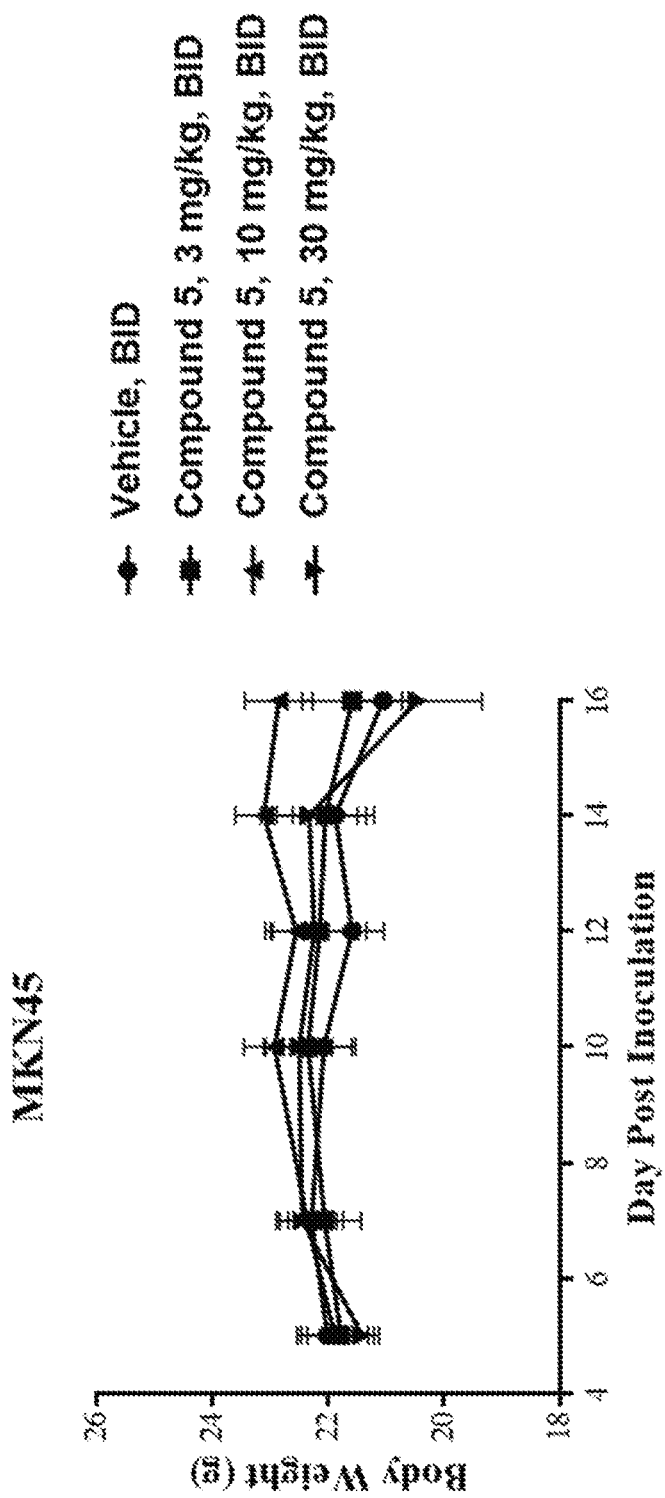

FIG. 8 shows the effect of Compound 5 on the body weight of mice bearing MKN-45 xenograft tumors. (●) vehicle, (■) Compound 5 at 3 mg/kg BID, (▲) Compound 5 at 10 mg/kg BID, (▼) Compound 5 at 30 mg/kg BID.

Figure 9:
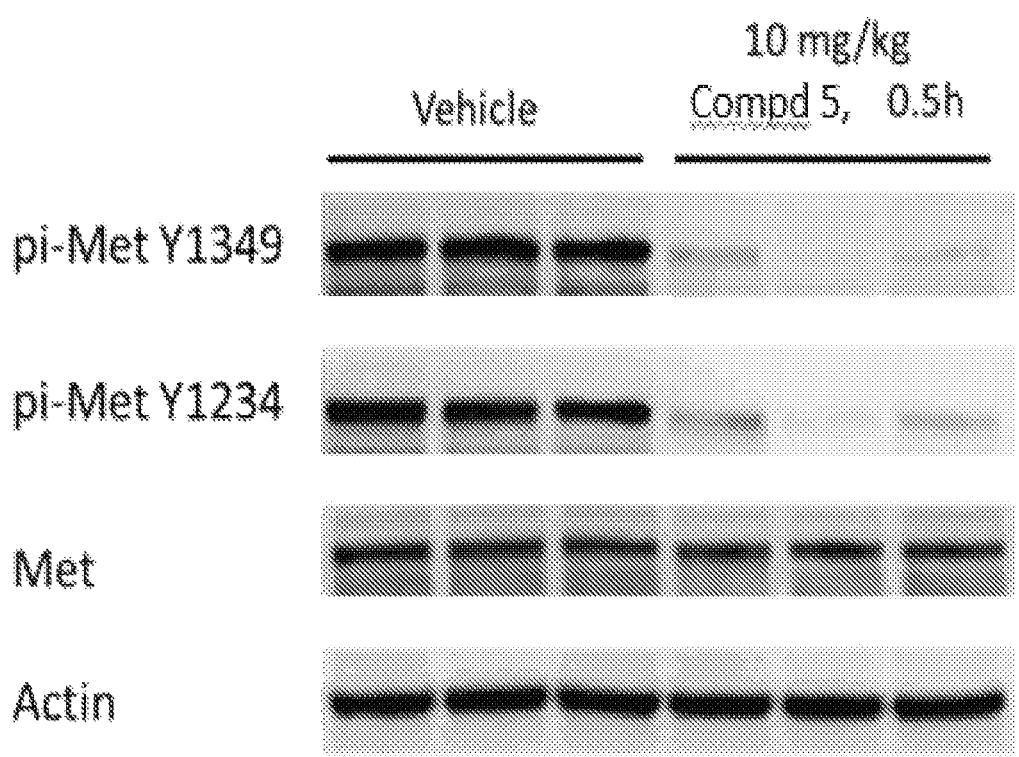

FIG. 9 shows a gel image of studies of inhibition of MET phosphorylation by Compound 5 in the MKN-45 xenograft model.

Figure 10:
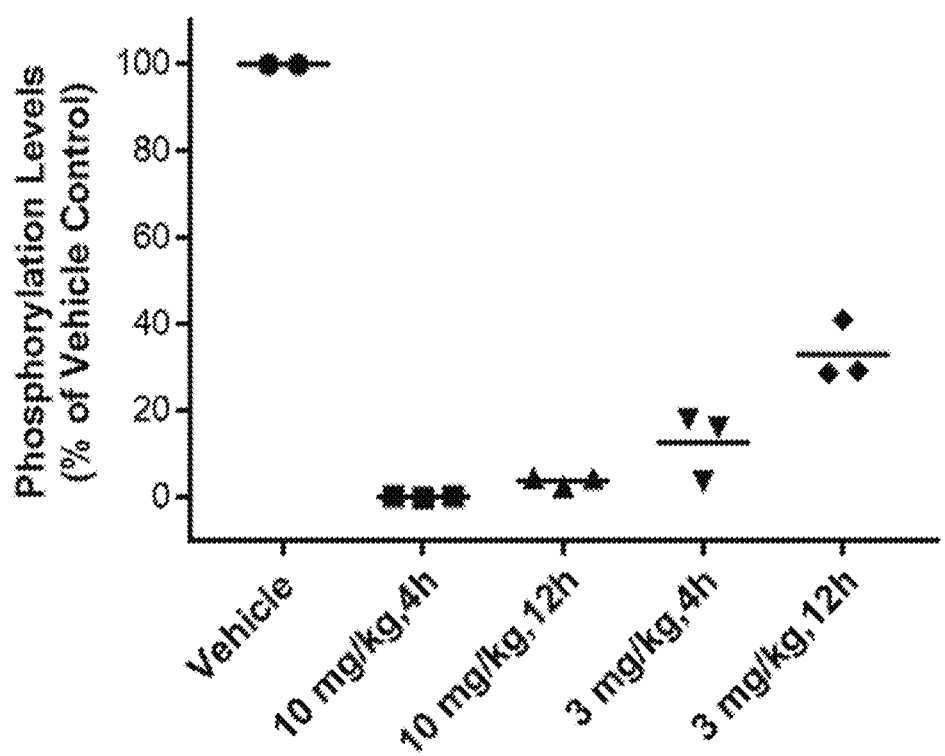

FIG. 10 is a chart showing the effect of Compound 5 on the phosphorylation od Met Y1234/1235 in MKN-45 tumors. (●) Vehicle, (■) Compound 5 at 10 mg/kg 4 Hrs, (▲) Compound 5 at 10 mg/kg 12 Hrs, (▼) Compound 5 at 3 mg/kg 4 Hrs, (♦) Compound 5 at 3 mg/kg 12 Hrs.

Figure 11:
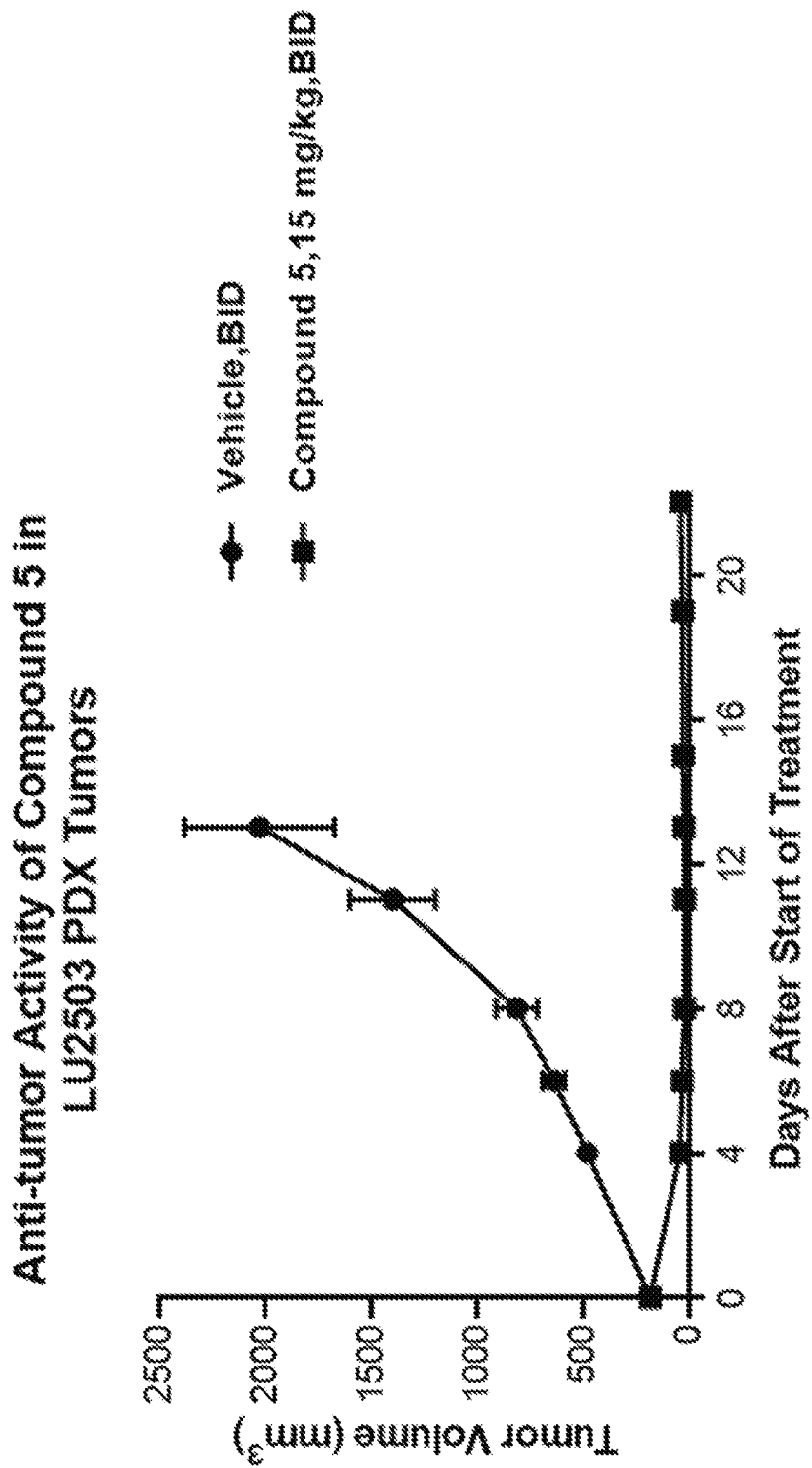

FIG. 11 is a chart showing the anti-tumor activity of Compound 5 in LU2503 PDX tumors. (●) Vehicle, (■) Compound 5 at 15 mg/kg BID.

Figure 12:
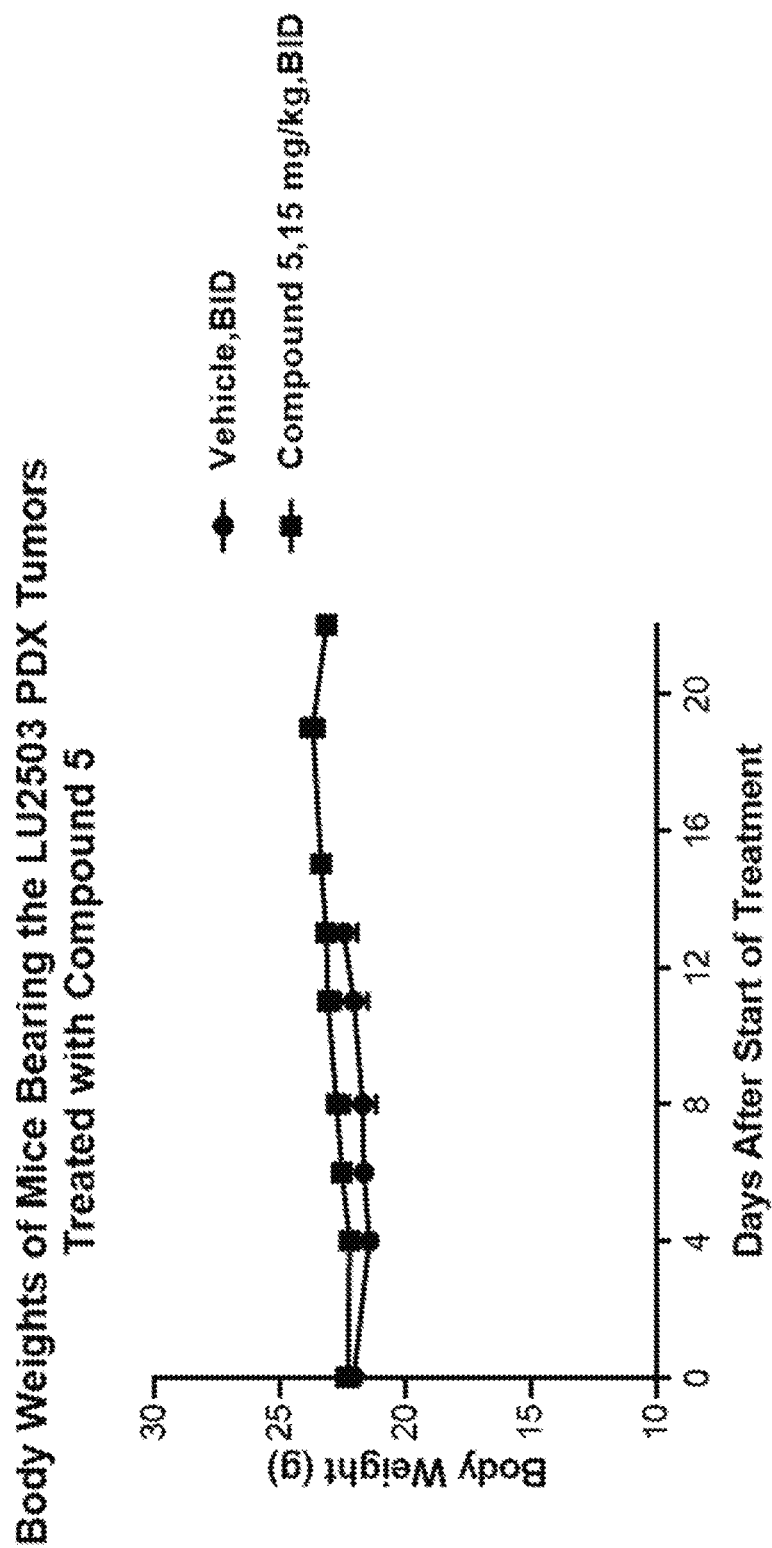

FIG. 12 is a chart showing the body weights of mice bearing LU2503 PDX tumors treated with Compound 5. (●) Vehicle, (■) Compound 5 at 15 mg/kg BID.

Figure 13:
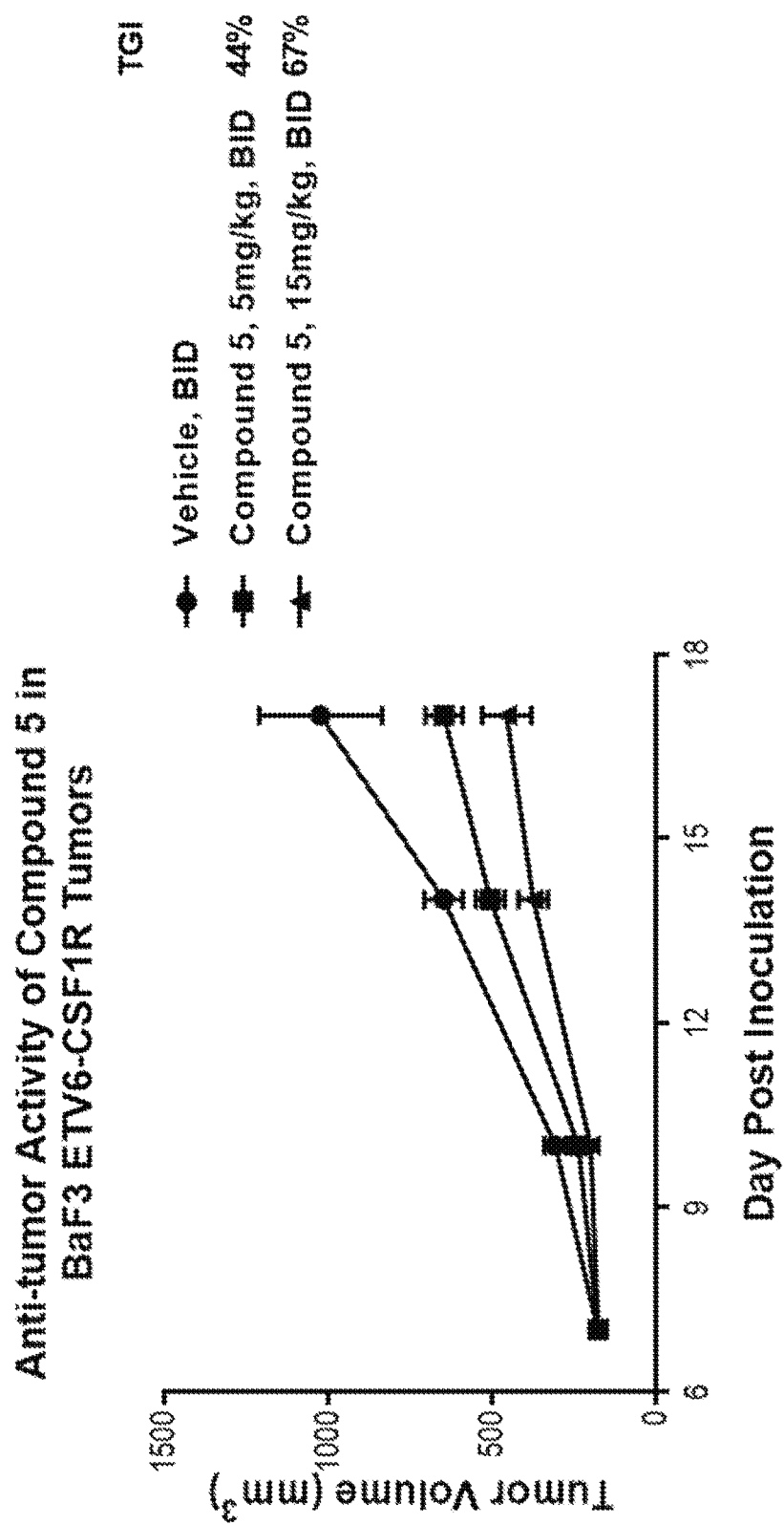

FIG. 13 is a chart showing the anti-tumor activity of Compound 5 in BaF3 ETV6-CSF1R tumors. (●) Vehicle, (■) Compound 5 at 5 mg/kg BID, (▲) Compound 5 at 15 mg/kg BID.

Figure 14:
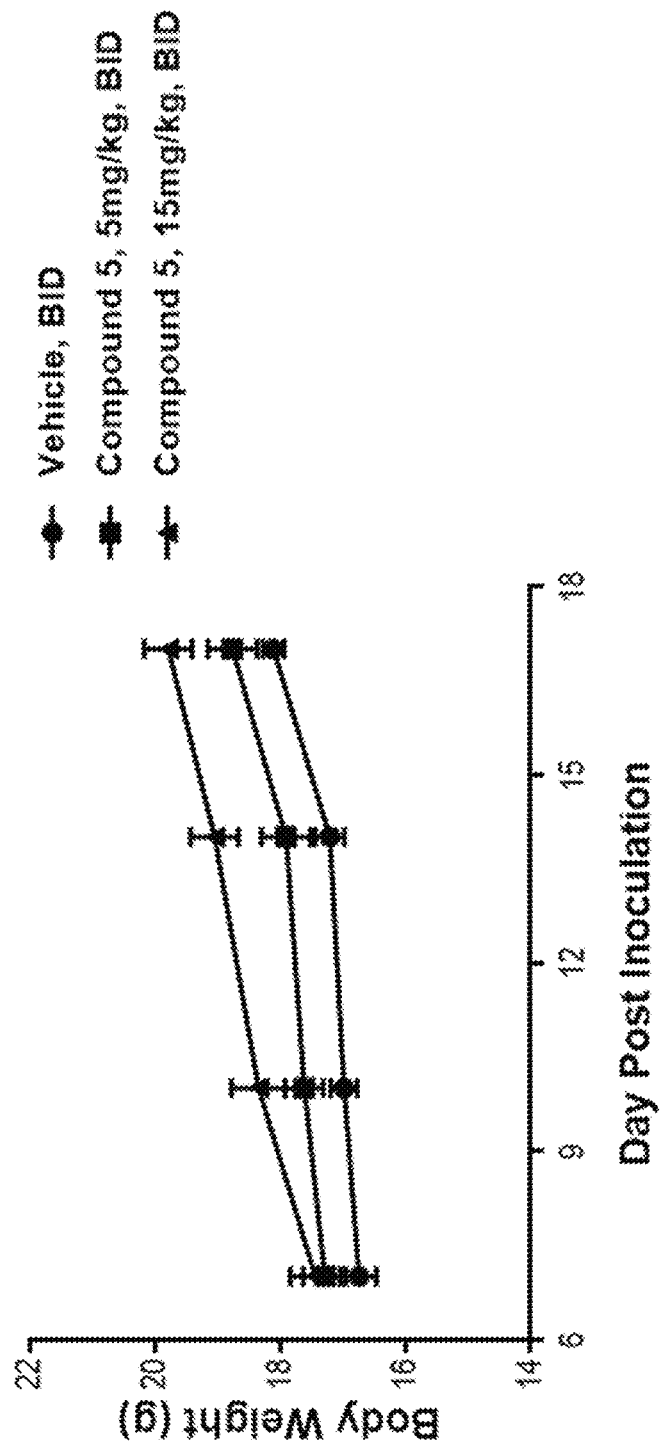

FIG. 14 is a chart showing the body weights of mice bearing LU25BaF3 ETV6-CSF1R tumors treated with Compound 5. (●) Vehicle, (■) Compound 5 at 5 mg/kg BID, (▲) Compound 5 at 15 mg/kg BID.

Figure 15:
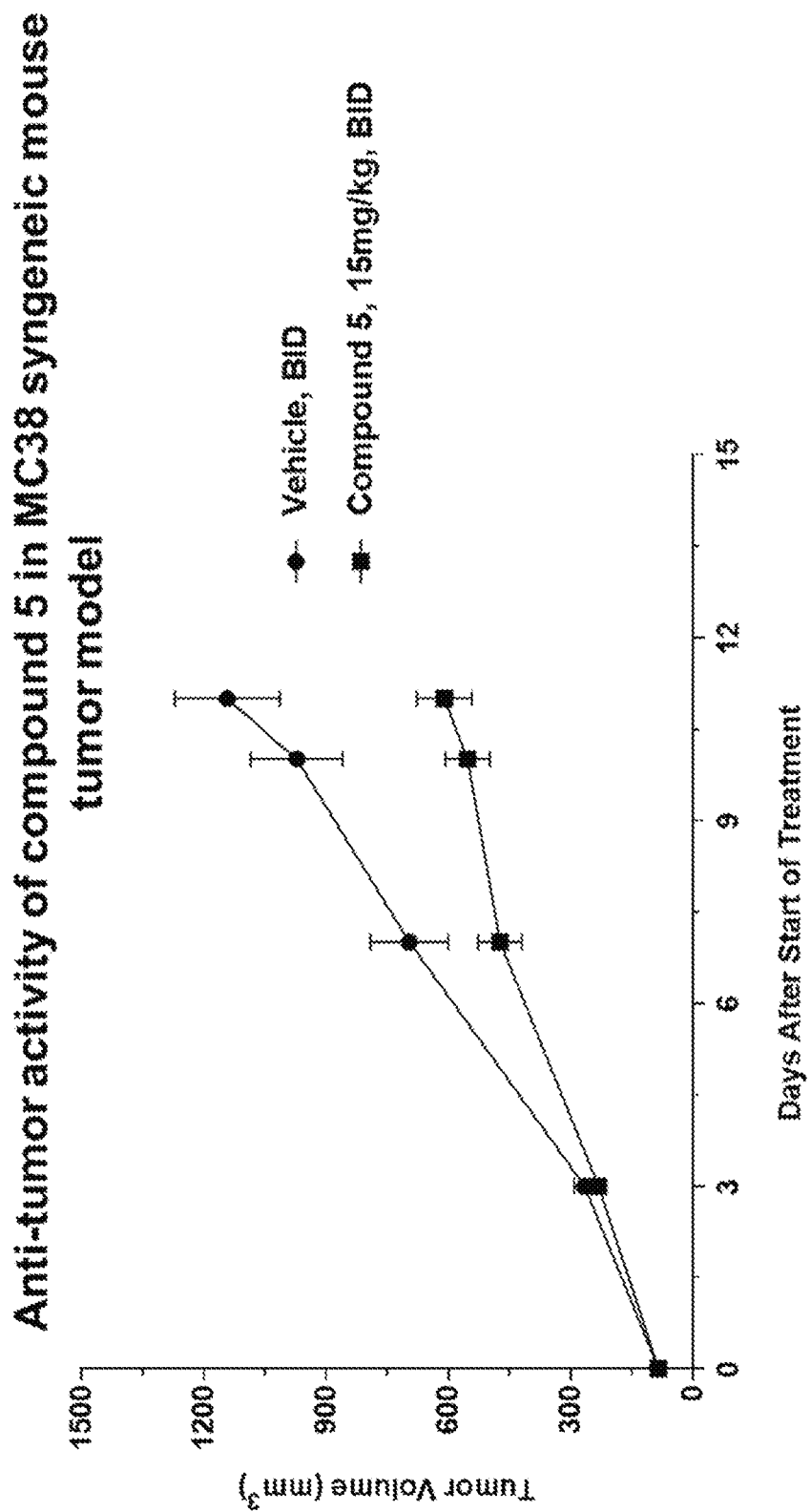

FIG. 15 is a chart showing the anti-tumor activity of Compound 5 in MC38 synergistic mouse tumor model. (●) Vehicle, (■) Compound 5 at 15 mg/kg BID.

Figure 16:
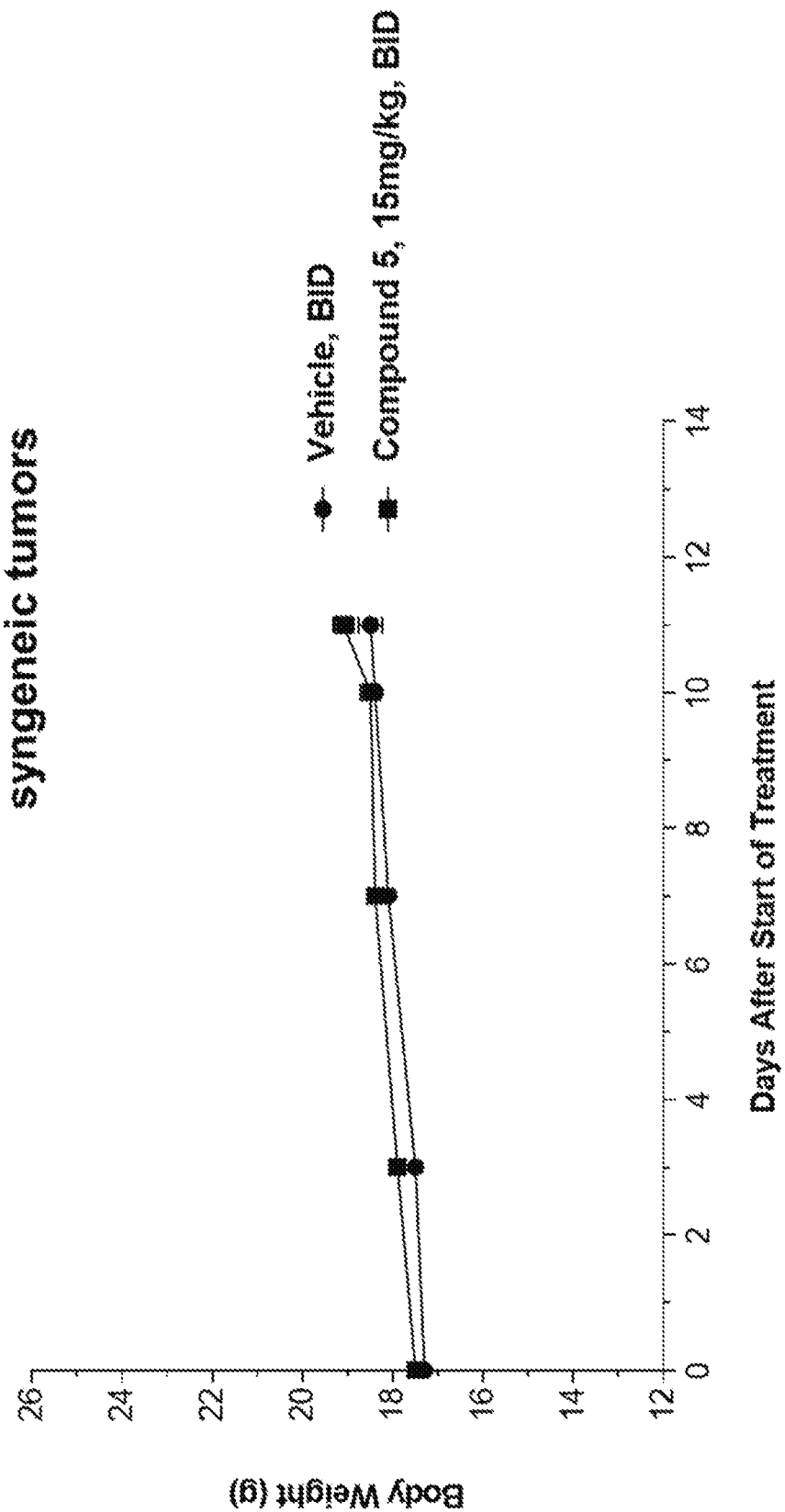

FIG. 16 is a chart showing the body weights of mice bearing MC38 synergistic mouse tumor model treated with Compound 5. (●) Vehicle, (■) Compound 5 at 15 mg/kg BID.

FIG. 17A-17G are graphs showing FACS analysis of tumor samples from each group after Day 7 treatment with Compound 5. FIG. 17A shows % in CD45+ cells; CD8 T-cells.

FIG. 17B shows % in CD45+ cells; CD4 T-cells. FIG. 17C shows % in CD45+ cells; T-Reg.

FIG. 17D shows % in CD45+ cells; MDSCs. FIG. 17E shows % in CD45+ cells; TAMs. FIG. 17F shows % in CD45+ cells; M1 macrophage. 17G shows % in CD45+ cells; M2 macrophage.

FIG. 18A-18G are graphs showing FACS analysis of tumor samples from each group after Day 11 treatment with Compound 5. FIG. 18A shows % in CD45+ cells; CD4 T-cells.

FIG. 18B shows % in CD45+ cells; CD8 T-cells. FIG. 18C shows % in CD45+ cells; T-Reg.

FIG. 18D shows % in CD45+ cells; MDSCs. FIG. 18E shows % in CD45+ cells; TAMs. FIG. 18F shows % in CD45+ cells; M1 macrophage. 18G shows % in CD45+ cells; M2 macrophage.

Figure 19:
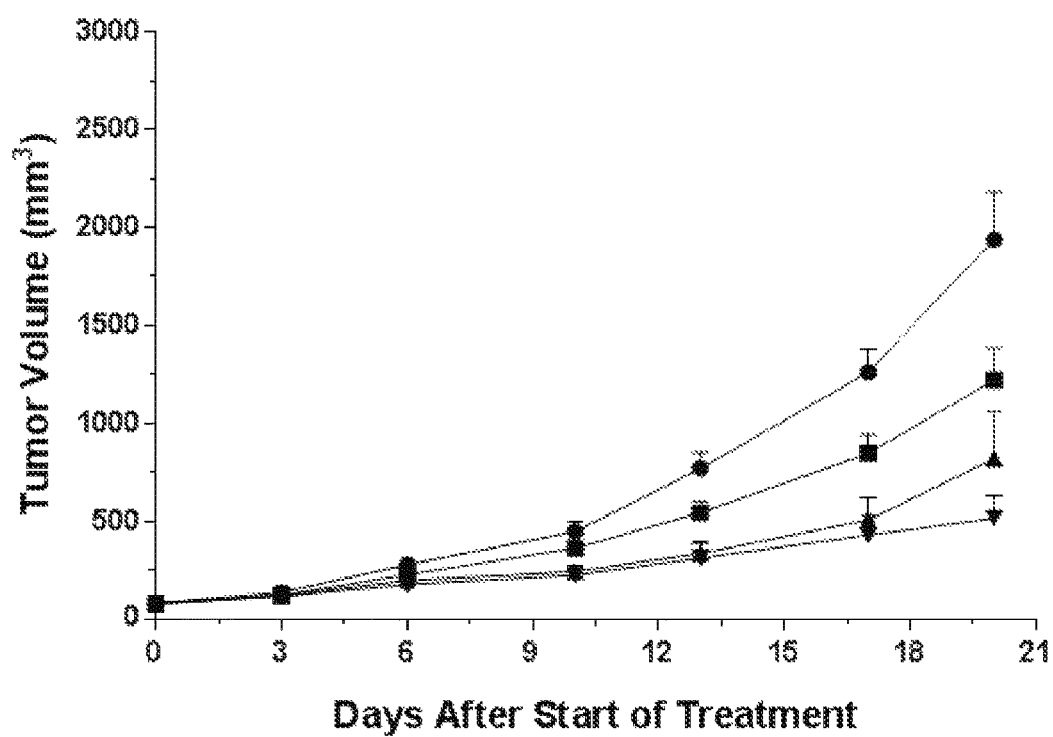

FIG. 19 is a chart showing the in-vivo efficacy of Compound 5 in subcutaneous MC38 synergistic mouse tumor model. (●) G1-Vehiclie+ISO IiG; (■) Compound 5; (▲) Anti-PD-1, (▼) Compound 5+Anti-PD-1.

Figure 20:
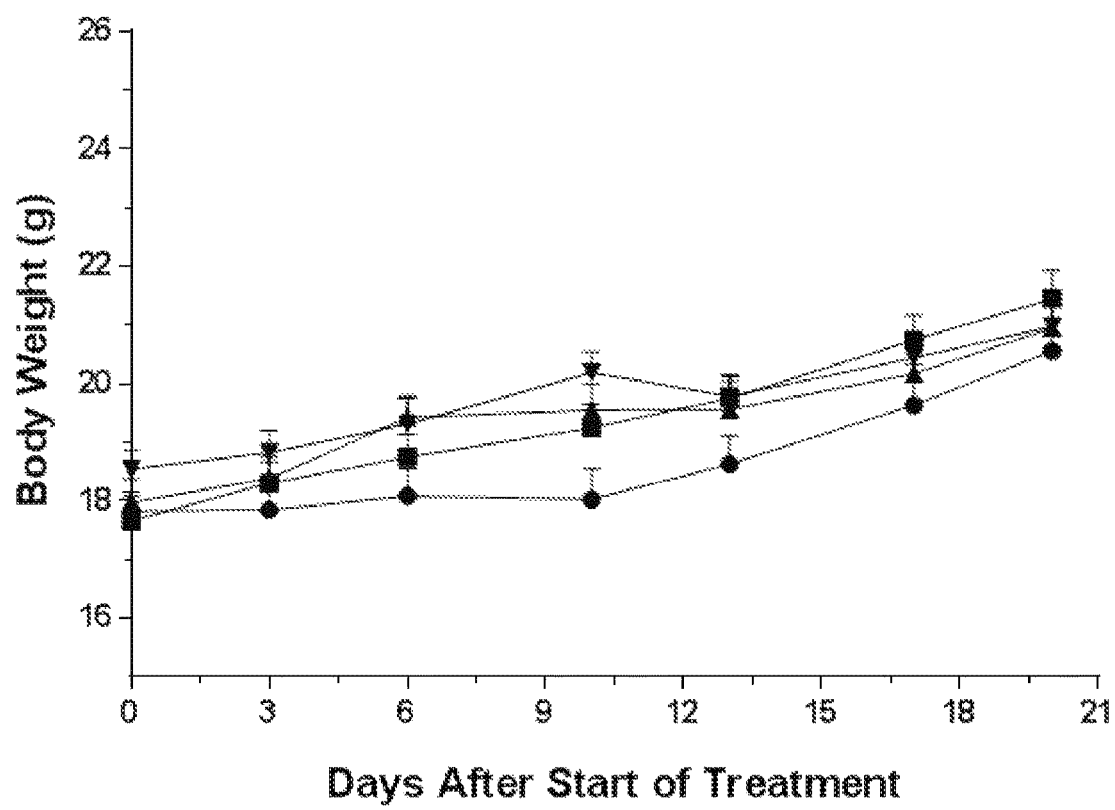

FIG. 20 is a chart showing the body weights of mice bearing subcutaneous MC38 synergistic mouse tumor model. (●) G1-Vehiclie+ISO IiG; (■) Compound 5; (▲) Anti-PD-1, (▼) Compound 5+Anti-PD-1.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbomenyl, 9H-fluoren-9-yl, and the like. Illustrative examples of cycloalkyl groups shown in graphical representations include the following entities, in the form of properly bonded moieties:

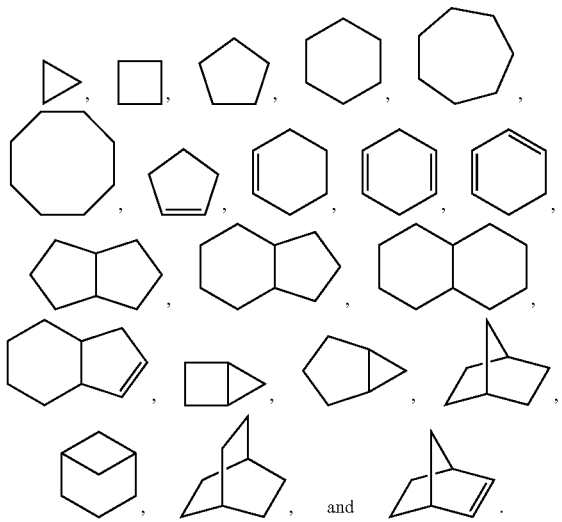

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

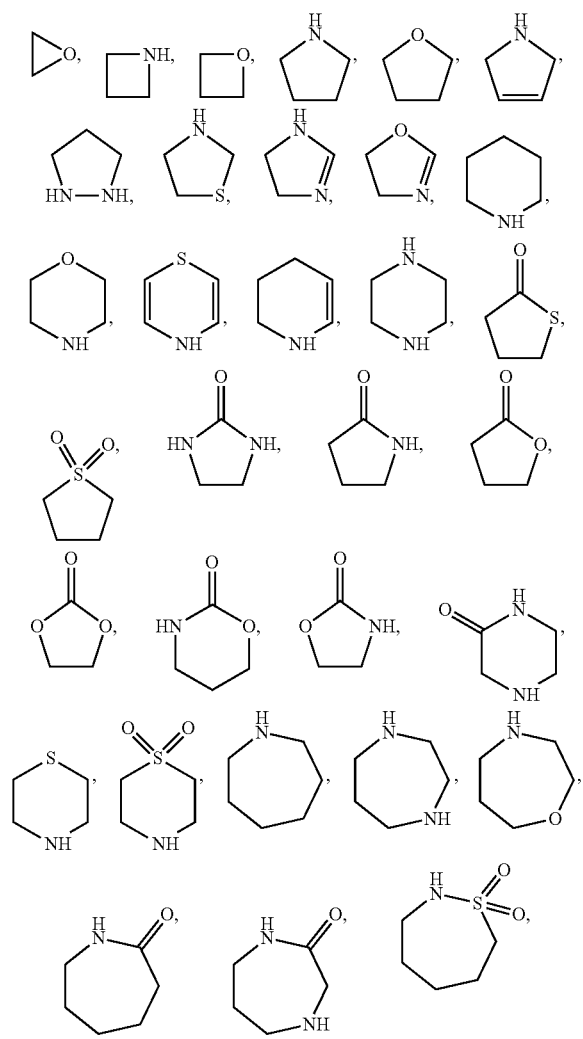

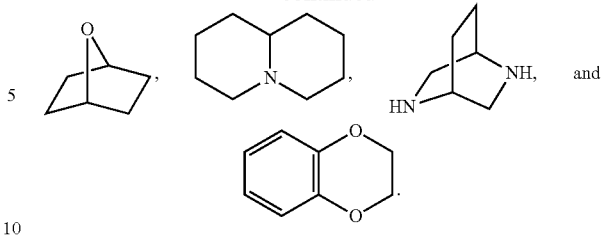

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

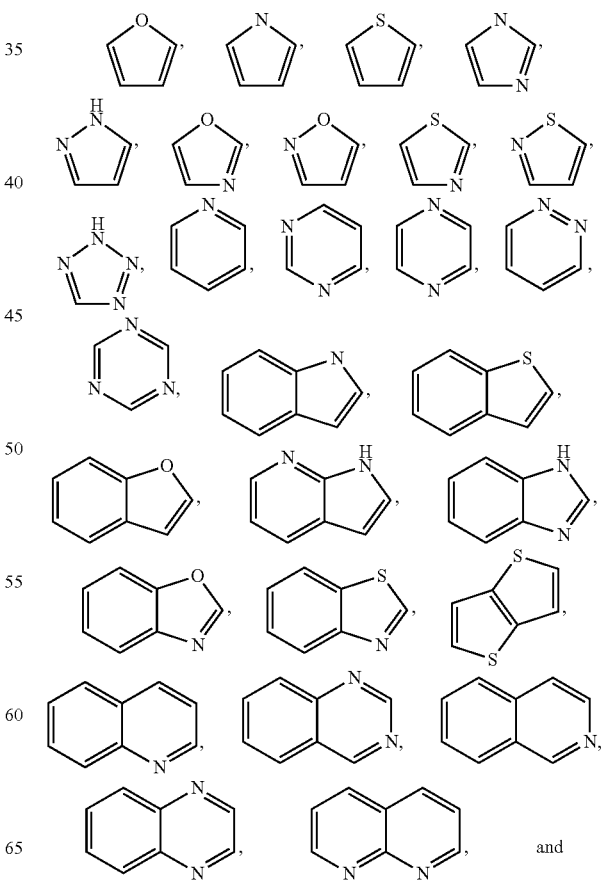

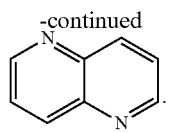

As used herein, "hydroxy" or ""hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, 7-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I, and uses of such metabolites in the methods of the disclosure. A "pharmaceutically active metabolite" means a pharmacologically active product of metabolism in the body of a compound of Formula I, or pharmaceutically acceptable salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " ⟿ " include both stereoisomers for the carbon atom to which the symbol " ⟿ " is attached, specifically both the bonds "■" and "⫶⫶⫶" are encompassed by the meaning of " ⟿ ". For example, in some exemplary embodiments, certain compounds provided herein can be described by the formula

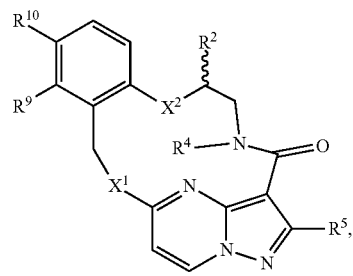

which formula will be understood to encompass compounds having both stereochemical configurations at the relevant carbon atom. Specifically, in this example, the configurations can be described by the formulas

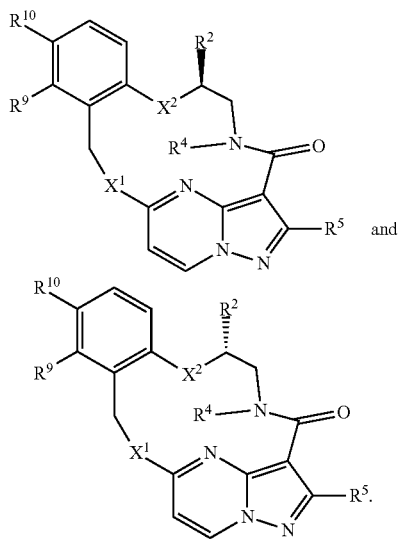

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member. The use of "-" in connection with the various chemical formulae provided herein to describe the various embodiments refers to a covalent bond (also referred to as a point of attachment) from the group to which "-" to the remainder of the molecule.

REPRESENTATIVE EMBODIMENTS

In some embodiments, compounds described herein comprise a moiety of the formula

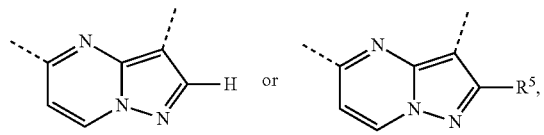

wherein $R^5$ is —$NR^6R^7$; and $R^6$ and $R^7$ are each independently selected from the group consisting of H, $C_1$-$C_6$ alkyl, $C_2$-$C_6$ alkenyl, $C_2$-$C_6$ alkynyl, and $C_3$-$C_6$ cycloalkyl; wherein each hydrogen atom in $C_1$-$C_6$ alkyl, $C_2$-$C_6$ alkenyl, $C_2$-$C_6$ alkynyl, and $C_3$-$C_6$ cycloalkyl is independently optionally substituted by fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —$CO_2H$, —C(O)$OC_1$-$C_6$ alkyl, —C(O)$NH_2$, —C(O)NH ($C_1$-$C_6$ alkyl), or —C(O)N($C_1$-$C_6$ alkyl)$_2$.

In some embodiments, compounds described herein comprise a moiety of the formula

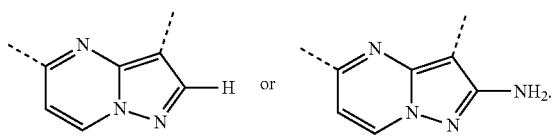

In still other embodiments, compounds described herein comprise a moiety of the formula

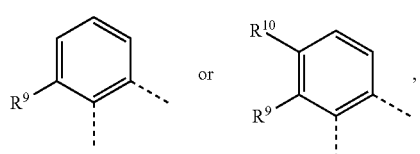

wherein $R^9$ is H, fluoro, chloro, bromo, —CN, —$CF_3$, —$CO_2H$, —C(O)$OC_1$-$C_6$ alkyl, —C(O)$NH_2$, —C(O)NH ($C_1$-$C_6$ alkyl) and —C(O)N($C_1$-$C_6$ alkyl)$_2$; and $R^{10}$ is H, fluoro, chloro or bromo.

In still other embodiments, compounds described herein comprise a moiety of the formula

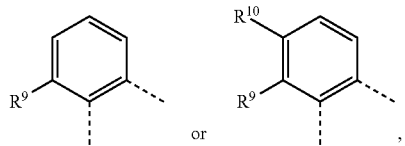

wherein $R^9$ is fluoro, chloro, bromo, —CN, —$CF_3$, —$CO_2H$, —C(O)$OC_1$-$C_6$ alkyl, —C(O)$NH_2$, —C(O)NH ($C_1$-$C_6$ alkyl) and —C(O)N($C_1$-$C_6$ alkyl)$_2$; and $R^{10}$ is fluoro, chloro or bromo.

In some embodiments, when compounds described herein comprise a moiety of the formula

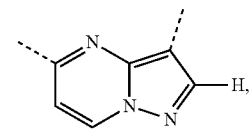

then $R^9$ in the moiety of the formula

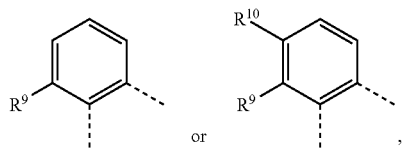

then $R^9$ is selected from the group consisting of —CN, —$CF_3$, —$CO_2H$, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

In still other embodiments, compounds described herein comprise a moiety of the formula

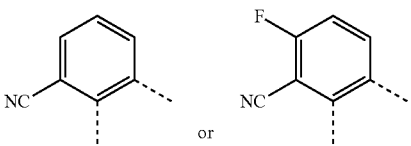

In still other embodiments, compounds described herein comprise a moiety of the formula

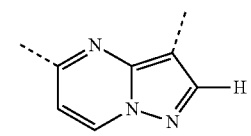

and a moiety of the formula

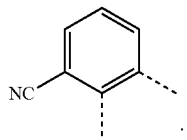

In still other embodiments, compounds described herein comprise a moiety of the formula

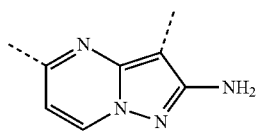

and a moiety of the formula

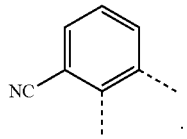

In still other embodiments, compounds described herein comprise a moiety of the formula

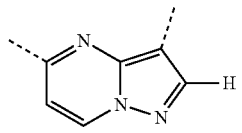

and a moiety of the formula

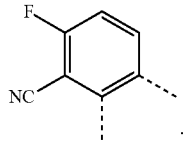

In still other embodiments, compounds described herein comprise a moiety of the formula

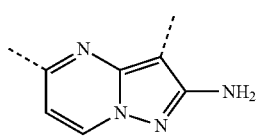

N and a moiety of the formula

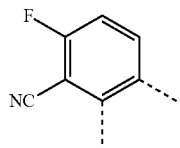

In some embodiments, $X^1$ is —N($R^8$)—. In some embodiments, $X^2$ is —O—. In some embodiments, $X^1$ is —N($R^8$)—, and $X^2$ is —O—.

In some embodiments, R is $C_1$-$C_6$ alkyl, $C_2$-$C_6$ alkenyl, $C_2$-$C_6$ alkynyl, $C_3$-$C_6$ cycloalkyl, $C_3$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl. In some embodiments, $R^1$ is H.

In some embodiments, $R^2$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O$XC_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-

$C_6$ alkyl)$_2$, —P(O)($C_1$-$C_6$ alkyl)$_2$, $C_3$-$C_6$ cycloalkyl, or 3- to 7-membered heterocycloalkyl.

In some embodiments, $R^2$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(OX$C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl, and $R^3$ is H.

In some embodiments, $R^2$ is $C_1$-$C_6$ alkyl, wherein each hydrogen atom in $C_1$-$C_6$ alkyl is independently optionally substituted with one or more moieties selected from group consisting of —F, —OH, —O$C_1$-$C_6$ alkyl, —NH$_2$, —NH($C_1$-$C_6$ alkyl), and —N($C_1$-$C_6$ alkyl)$_2$. In some embodiments, $R^2$ is $C_1$-$C_6$ alkyl, wherein each hydrogen atom in $C_1$-$C_6$ alkyl is independently optionally substituted with one or more moieties selected from group consisting of —F, —OH, —O$C_1$-$C_6$ alkyl, —NH$_2$, —NH($C_1$-$C_6$ alkyl), and —N($C_1$-$C_6$ alkyl)$_2$, and $R^3$ is H. In some embodiments, $R^2$ is methyl. In some embodiments, $R^2$ is methyl, and $R^3$ is H.

In some embodiments, $R^4$ is H. In some embodiments, $R^4$ is $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl.

In some embodiments, $R^8$ is $C_1$-$C_6$ alkyl, wherein each hydrogen atom is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl), or —C(O)N($C_1$-$C_6$ alkyl)$_2$. In some embodiments, $R^8$ is ethyl, propyl, iso-propyl, or methylcyclopropyl.

In other embodiments, the compound of Formula I is selected from the group consisting of (7S)-3-amino-12-chloro-14-ethyl-11-fluoro-7-methyl-6,7,13,14-tetrahydro-1,15-ethenopyrazolo[4,3-f][1,4,8,10]benzoxatriazacyclotridecin-4(5H)-one, (7S)-14-ethyl-7-methyl-4-oxo-4,5,6,7,13,14-hexahydro-1,15-ethenopyrazolo[4,3-f][1,4,8,10]benzoxatriazacyclo-tridecine-12-carbonitrile, 14-ethyl-4-oxo-4,5,6,7,13,14-hexahydro-1,15-ethenopyrazolo[4,3-f][1,4,8,10]benzoxatriazacyclotridecine-12-carbonitrile, (7S)-14-ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile, (7S)-3-amino-14-ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile, (7S)-3-amino-14-ethyl-7-methyl-4-oxo-4,5,6,7,13,14-hexahydro-1,15-ethenopyrazolo[4,3-][1,4,8,10]-benzoxatriazacyclotridecine-12-carbonitrile, (7S)-3-amino-14-(cyclopropylmethyl)-11-fluoro-7-methyl-4-oxo-4,5,6,7,13,14-hexahydro-1,15-ethenopyrazolo[4,3-f][1,4,8,10]benzoxatriazacyclotridecine-12-carbonitrile, (7S)-3-amino-11-fluoro-7-methyl-4-oxo-14-(propan-2-yl)-4,5,6,7,13,14-hexahydro-1,15-ethenopyrazolo[4,3-f][1,4,8,10]benzoxatriaza-cyclotridecine-12-carbonitrile, or a pharmaceutically acceptable salt thereof.

The following represent illustrative embodiments of compounds of the Formula I:

| Cpd | Structure | Name |
|---|---|---|
| 1 | 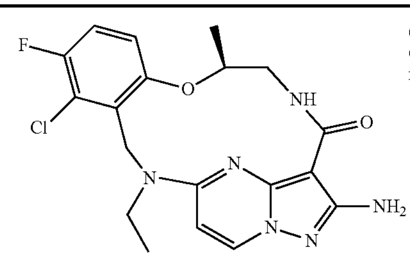 | (7S)-3-amino-12-chloro-14-ethyl-11-fluoro-7-methyl-6,7,13,14-tetrahydro-1,15-ethenopyrazolo[4,3-f][1,4,8,10]benzoxatriazacyclotridecin-4(5H)-one |
| 2 | 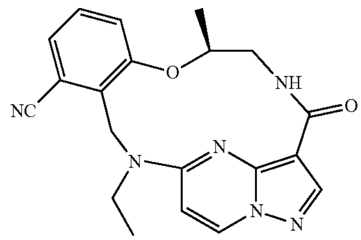 [SMILES: CCN1Cc2c(C#N)cccc2O[C@@H](C)CNC(=O)c2cnn3ccc1nc23] | (7S)-14-ethyl-7-methyl-4-oxo-4,5,6,7,13,14-hexahydro-1,15-ethenopyrazolo[4,3-f][1,4,8,10]benzoxatriazacyclotridecine-12-carbonitrile |

-continued

| Cpd | Structure | Name |
|---|---|---|
| 3 | 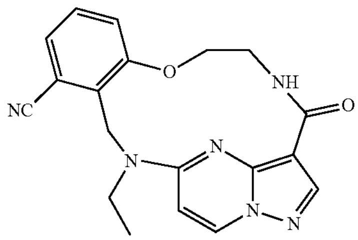 [SMILES: CCN1Cc2c(C#N)cccc2OCCNC(=O)c2cnn3ccc1nc23] | 14-ethyl-4-oxo-4,5,6,7,13,14-hexahydro-1,15-ethenopyrazolo[4,3-f][1,4,8,10]benzoxatriazacyclotridecine-12-carbonitrile |
| 4 | 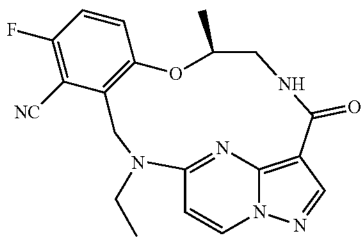 [SMILES: CCN1Cc2c(ccc(F)c2C#N)O[C@@H](C)CNC(=O)c2cnn3ccc1nc23] | (7S)-14-ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |
| 5 | 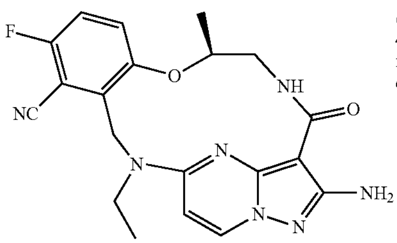 | (7S)-3-amino-14-ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |
| 6 | 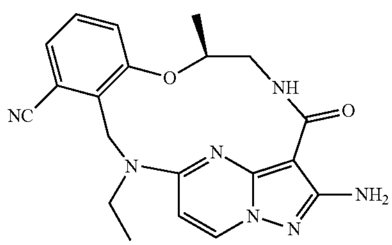 [SMILES: CCN1Cc2c(C#N)cccc2O[C@@H](C)CNC(=O)c2c(N)nn3ccc1nc23] | (7S)-3-amino-14-ethyl-7-methyl-4-oxo-4,5,6,7,13,14-hexahydro-1,15-ethenopyrazolo[4,3-f][1,4,8,10]benzoxatriazacyclotridecine-12-carbonitrile |
| 7 | 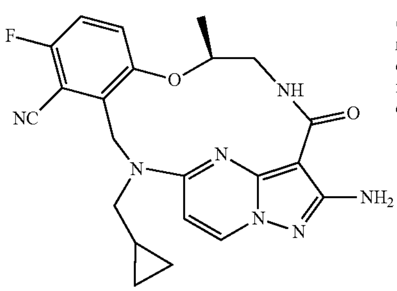 | (7S)-3-amino-14-(cyclopropylmethyl)-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |
| 8 | 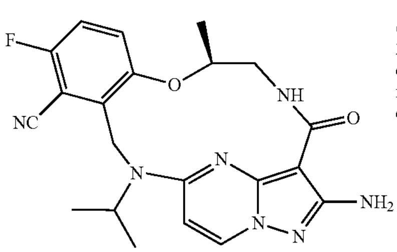 | (7S)-3-amino-11-fluoro-7-methyl-4-oxo-14-(propan-2-yl)-4,5,6,7,13,14-hexahydro-1,15-ethenopyrazolo[4,3-f][1,4,8,10]benzoxatriazacyclotridecine-12-carbonitrile |

| Cpd | Structure | Name |
|---|---|---|
| 9 | 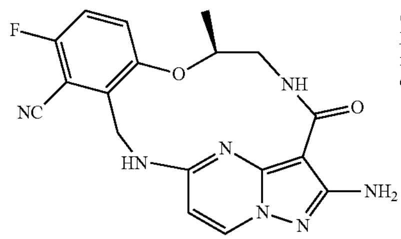 | (7S)-3-amino-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |
| 10 | 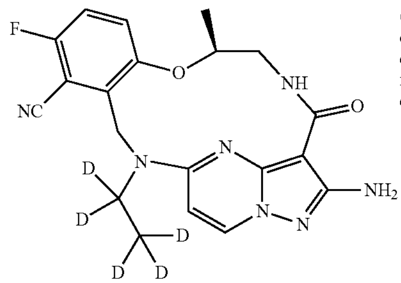 | (7S)-3-amino-14-($^2$H$_5$)ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |
| 11 | 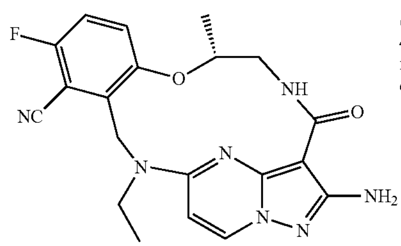 | (7R)-3-amino-14-ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile |

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the description are sterile compositions. Pharmaceutical compositions may be prepared using compounding techniques known or that become available to those skilled in the art.

Sterile compositions are also contemplated by the description, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the description may be administered by a suitable route of delivery, such as oral, parenteral, rectal, nasal, topical, or ocular routes, or by inhalation. Preferably, the compositions are formulated for intravenous or oral administration.

For oral administration, the compounds the description may be provided in a solid form, such as a tablet or capsule, or as a solution, emulsion, or suspension. To prepare the oral compositions, the compounds of the description may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the description may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present description are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the description may utilize a patch formulation to affect transdermal delivery.

Methods of Treatment

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human. As used herein "cancer" includes any cancer known in the art, particularly those cancers where SRC and MET, and/or CSF1R have been implicated in the disease. Examples of cancer types include, but are not limited to, carcinomas, sarcomas, lymphomas, Hodgekin's disease, melanomas, mesotheliomas, Burkitt's lymphoma, nasopharyngeal carcinomas, leukemias, and myelomas. Examples of specific cancers include, but are not limited to, oral cancer, thyroid cancer, endocrine cancer, skin cancer, gastric cancer, esophageal cancer, laryngeal cancer, pancreatic cancer, colon cancer, bladder cancer, bone cancer, ovarian cancer, cervical cancer, uterine cancer, breast cancer, testicular cancer, prostate cancer, renal cancer, rectal cancer, kidney cancer, liver cancer, glioblastoma, or head & neck cancer, and lung cancers, such as non-small cell lung cancer, small cell lung cancer, and the like.

In one aspect, the compounds and pharmaceutical compositions of the description specifically target SRC and MET, and/or CSF1R. Thus, these compounds and pharmaceutical compositions can be used to prevent, reverse, slow, or inhibit the activity of one or more of SRC and MET, and/or CSF1R. In some embodiments, methods of treatment of cancer comprising administering a therapeutically effective amount of a compound that inhibits one or more of SRC and MET, and/or CSF1R are described herein. In other embodiments, methods for treating cancer comprising a. administering a therapeutically effective amount of a compound as described herein that inhibits one or more of SRC and MET, and/or CSF1R are described. In other embodiments, methods for treating cancer comprising a. administering a therapeutically effective amount of a compound as described herein are described. In other embodiments, the cancer is gastric cancer, colon cancer, renal cancer, liver cancer, lung cancer, glioblastoma, or head & neck cancer.

In some embodiments, the disclosure is directed to a compound that inhibits SRC and MET, and/or CSF1R, or a pharmaceutically acceptable salt thereof, for use in the treatment of cancer in a patient. In some embodiments, the compound that inhibits SRC and MET, and/or CSF1R is of the Formula I. In some embodiments, the cancer is gastric cancer, colon cancer, renal cancer, liver cancer, lung cancer, glioblastoma, or head & neck cancer.

In some embodiments, the disclosure is directed to use of a compound that inhibits SRC and MET, and/or CSF1R, or a pharmaceutically acceptable salt thereof, for use in the treatment of cancer in a patient. In some embodiments, the compound that inhibits SRC and MET, and/or CSF1R is of the Formula I. In some embodiments, the cancer is gastric cancer, colon cancer, renal cancer, liver cancer, lung cancer, glioblastoma, or head & neck cancer.

In some embodiments, the disclosure is directed to use of a compound that inhibits SRC and MET, and/or CSF1R, or a pharmaceutically acceptable salt thereof, in the preparation of a medicament for the treatment of cancer in a patient. In some embodiments, the compound that inhibits SRC and MET, and/or CSF1R is of the Formula I. In some embodiments, the cancer is gastric cancer, colon cancer, renal cancer, liver cancer, lung cancer, glioblastoma, or head & neck cancer.

In some embodiments, the disclosure is directed to a composition comprising a compound that inhibits SRC and MET, and/or CSF1R, or a pharmaceutically acceptable salt thereof, in a therapeutically effective amount, for use in the treatment of cancer in a patient. In some embodiments, the compound that inhibits SRC and MET, and/or CSF1R is of the Formula I. In some embodiments, the cancer is gastric cancer, colon cancer, renal cancer, liver cancer, lung cancer, glioblastoma, or head & neck cancer.

In the inhibitory methods of the description, an "effective amount" means an amount sufficient to inhibit the target. Measuring such target modulation may be performed by routine analytical methods such as those described below. Such modulation is useful in a variety of settings, including in vitro assays. In such methods, the cell can be a cancer cell with abnormal signaling due to upregulation, mutation, aberrant activity of, and/or changes in SRC and MET, and/or CSF1R.

In treatment methods according to the description, an "effective amount" means an amount or dose sufficient to generally bring about the desired therapeutic benefit in subjects needing such treatment. Effective amounts or doses of the compounds of the description may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present description or may be included with a compound of the present description in a single pharmaceutical composition. The additional active ingredients may be administered simultaneously with, prior to, or after administration of a compound of the present description.

Combination agents include additional active ingredients are those that are known or discovered to be effective in treating the diseases and disorders described herein, including those active against another target associated with the disease. For example, compositions and formulations of the description, as well as methods of treatment, can further comprise other drugs or pharmaceuticals, e.g., other active agents useful for treating or palliative for the target diseases or related symptoms or conditions. Such additional agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the description may additional comprise one or more of such active agents, and methods of treatment may additionally comprise administering an effective amount of one or more of such active agents.

In some embodiments, the disclosure is directed to a method of treating cancer in a patient comprising, a. administering a therapeutically effective amount of a compound that inhibits SRC and MET, and/or CSF1R; and b. administering a therapeutically effective amount of at least one additional anti-cancer agent. In some embodiments, the at least one additional anti-cancer agent is an EGFR inhibitor, or a pharmaceutically acceptable salt thereof. In some embodiments, the additional anti-cancer agent is an antibody of EGFR. In some embodiments, the compound that inhibits SRC and MET, and/or CSF1R is of the Formula I. In some embodiments, the cancer is gastric cancer, liver cancer, lung cancer, or head & neck cancer.

In some embodiments, the disclosure is directed to a compound that inhibits SRC and MET, and/or CSF1R, or a pharmaceutically acceptable salt thereof, in combination with a therapeutically effective amount of at least one additional anti-cancer agent, or a pharmaceutically acceptable salt thereof, for use in the treatment of cancer in a patient. In some embodiments, the at least one additional anti-cancer agent is an EGFR inhibitor, or a pharmaceutically acceptable salt thereof. In some embodiments, the additional anti-cancer agent is an antibody of EGFR. In some embodiments, the compound that inhibits SRC and MET, and/or CSF1R is of the Formula I. In some embodiments, the cancer is gastric cancer, liver cancer, lung cancer, or head & neck cancer.

In some embodiments, the disclosure is directed to use of a compound that inhibits SRC and MET, and/or CSF1R, or a pharmaceutically acceptable salt thereof, in combination with a therapeutically effective amount of at least one additional anti-cancer agent for the treatment of cancer in a patient. In some embodiments, the compound that inhibits SRC and MET, and/or CSF1R is of the Formula I. In some embodiments of this aspect, the cancer is gastric cancer, liver cancer, lung cancer, or head & neck cancer. In some embodiments, the at least one additional anti-cancer agent is an EGFR inhibitor, or a pharmaceutically acceptable salt thereof. In some embodiments, the additional anti-cancer agent is an antibody of EGFR.

In some embodiments, the disclosure is directed to use of a compound that inhibits SRC and MET, and/or CSF1R, or a pharmaceutically acceptable salt thereof, in the preparation of a medicament for the treatment of cancer in a patient in combination with a therapeutically effective amount of at least one additional anti-cancer agent. In some embodiments, the compound that inhibits SRC and MET, and/or CSF1R is of the Formula I. In some embodiments of this aspect, the cancer is gastric cancer, liver cancer, lung cancer, or head & neck cancer. In some embodiments, the at least one additional anti-cancer agent is an EGFR inhibitor, or a pharmaceutically acceptable salt thereof. In some embodiments, the additional anti-cancer agent is an antibody of EGFR.

In some embodiments, the disclosure is directed to a composition comprising a compound that inhibits SRC and MET, and/or CSF1R, or a pharmaceutically acceptable salt thereof, in a therapeutically effective amount, for use in the treatment of cancer in a patient. In some embodiments of this aspect, the compound that inhibits SRC and MET, and/or CSF1R is of the Formula I. In some embodiments, the cancer is gastric cancer, liver cancer, lung cancer, or head & neck cancer. In some embodiments, the compound is administered in combination with a therapeutically effective amount of at least one additional anti-cancer agent. In some embodiments, the at least one additional anti-cancer agent is an EGFR inhibitor, or a pharmaceutically acceptable salt thereof. In some embodiments, the additional anti-cancer agent is an antibody of EGFR.

In some embodiments, the disclosure relates to a synergistic composition of a compound that inhibits SRC and MET, and/or CSFIR, and an EGFR inhibitor, where the two components come into contact with each other at a locus. In some embodiments, the compound that inhibits SRC and MET, and/or CSF1R is of the Formula I. In some embodiments, the at least one additional anti-cancer agent is an EGFR inhibitor, or a pharmaceutically acceptable salt thereof. In some embodiments, the additional anti-cancer agent is an antibody of EGFR.

EXAMPLES

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

| ABBREVIATIONS The examples described herein use materials, including but not limited to, those described by the following abbreviations known to those skilled in the art: | |
|---|---|
| g | grams |
| eq | equivalents |
| mmol | millimoles |
| mL | milliliters |
| EtOAc | ethyl acetate |
| MHz | megahertz |
| ppm | parts per million |
| δ | chemical shift |
| s | singlet |
| d | doublet |
| t | triplet |
| q | quartet |
| quin | quintet |
| br | broad |

| ABBREVIATIONS The examples described herein use materials, including but not limited to, those described by the following abbreviations known to those skilled in the art: | |
|---|---|
| m | multiplet |
| Hz | hertz |
| THF | tetrahydrofuran |
| ° C. | degrees Celsius |
| PE | petroleum ether |
| EA | ethyl acetate |
| $R_f$ | retardation factor |
| N | normal |
| J | coupling constant |
| DMSO-$d_6$ | deuterated dimethyl sulfoxide |
| n-BuOH | n-butanol |
| DIEA | n,n-diisopropylethylamine |
| TMSCl | trimethylsilyl chloride |
| min | minutes |
| hr | hours |
| Me | methyl |
| Et | ethyl |
| i-Pr | isopropyl |
| TLC | thin layer chromatography |
| M | molar |
| Compd# | compound number |
| MS | mass spectrum |
| m/z | mass-to-charge ratio |
| Ms | methanesulfonyl |
| FDPP | pentafluorophenyl diphenylphosphinate |
| Boc | tert-butyloxycarbonyl |
| TFA | trifluoroacetic acid |
| Tos | toluenesulfonyl |
| DMAP | 4-(dimethylamino)pyridine |
| μM | micromolar |
| ATP | adenosine triphosphate |
| $IC_{50}$ | half maximal inhibitory concentration |
| U/mL | units of activity per milliliter |
| KHMDS | potassium bis(trimethylsilyl)amide |
| DIAD | diisopropyl azodicarboxylate |
| MeTHF | 2-methyltetrahydrofuran |
| MOM | methoxymethyl |
| DCM | dichloromethane |
| DMF | N,N-dimethylformamide |
| DPPA | diphenyl phosphoryl azide |
| DBU | 1,8-diazabicyclo[5.4.0]undec-7-ene |
| DIPEA | N,N-diisopropylethylamine |

General Method A.

Preparation 2-chloro-3-fluoro-6-hydroxybenzaldehyde (A-14)

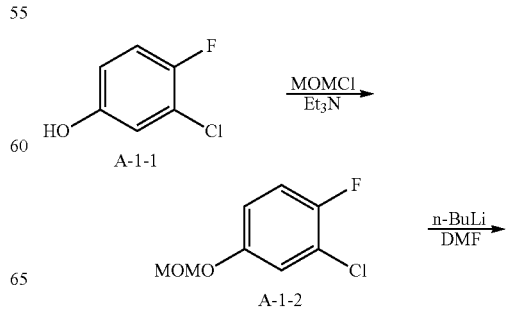

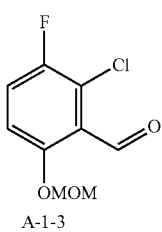 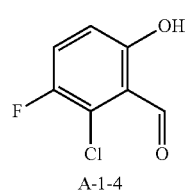 

A-1-3 → A-1-4

A-2-2

Step 1. To a solution of A-1-1 (20.00 g, 136.47 mmol, 1.00 eq.) and sodium hydride (6.55 g, 60% purity, 272.94 mmol, 2.00 eq.) in DMF (200.00 mL) was added MOMCl (21.97 g, 272.94 mmol, 20.73 mL, 2.00 eq.) at 0° C. under $N_2$. The mixture was stirred at 25° C. for 10 hours. TLC (Petroleum ether/Ethyl acetate=5/1) showed the starting material was consumed completely and one new spot was found. The reaction mixture was quenched by water (150 mL), and then diluted with water (150 mL) and extracted with ethyl acetate (3×100 mL). The combined organic layers were washed with brine (150 mL), dried over anhydrous sodium sulfate, filtered and concentrated under reduced pressure to give A-1-2 (20.00 g, 76.89% yield) as a colorless oil. $^1$H NMR (400 MHz, CDCl$_3$) δ: 7.11 (dd, J=2.8, 6.0 Hz, 1H), 7.04 (t, J=8.8 Hz, 1H), 6.90 (td, J=3.2, 9.2 Hz, 1H), 5.12 (s, 2H), 3.47 (s, 3H).

Step 2. To a solution of A-1-2 (20.00 g, 104.93 mmol, 1.00 eq.) in THF (250.00 mL) was added n-BuLi (2.5 M, 125.92 mL, 3.00 eq.) at −65° C. under $N_2$. The mixture was stirred at −65° C. for 2 hours. The mixture was quenched by DMF (76.69 g, 1.05 mol, 80.73 mL, 10.00 eq.) and the mixture was stirred at −65° C. for 15 min under $N_2$. TLC (Petroleum ether: Ethyl acetate=3:1) showed the starting material was consumed completely and one new spot was found. The reaction mixture was diluted with water (300 mL) and extracted with ethyl acetate (150 mL*3). Then combined organic layers were dried over anhydrous sodium sulfate, filtered and concentrated under reduced pressure to give a residue. The residue was purified by column chromatography (SiO$_2$, Petroleum ether/Ethyl acetate=I/O to 1/1) to give A-1-3 (4.80 g, 20.93% yield) as a colorless oil. $^1$H NMR (400 MHz, CDCl$_3$) δ: 10.48 (s, 1H), 7.28 (t, J=8.8 Hz, 1H), 7.15 (dd, J=4.0, 9.2 Hz, 1H), 5.25 (s, 2H), 3.51 (s, 3H).

Step 3. To a solution of A-1-3 (4.00 g, 18.3 mmol, 1.00 eq.) in HCl/dioxane (40.0 mL) was stirred at 25° C. for 2 hours. The reaction mixture was diluted with water (30.0 mL) and extracted with ethyl acetate (25.0 mL×3). The combined organic layers were washed with water (30.0 mL), dried over anhydrous sodium sulfate, filtered and concentrated under reduced pressure to give A-1-4 (2.50 g, 14.3 mmol, yield=78.3%) as a white solid. $^1$H NMR (400 MHz, CDCl$_3$) δ=11.68 (s, 1H), 10.43 (s, 1H), 7.37-7.32 (m, 1H), 6.91 (dd, J=4.0, 9.2 Hz, 1H).

General Method B.

Preparation of 2-bromo-3-fluoro-6-hydroxybenzaldehyde (A-2-4)

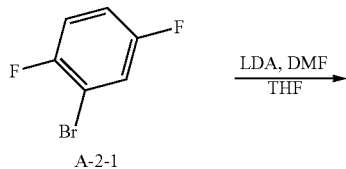

A-2-1

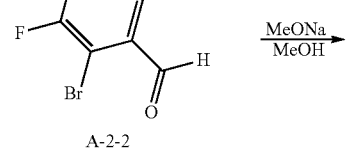

A-2-3 → A-2-4

Step 1. To a solution of A-2-1 (30.0 g, 155 mmol, 1 eq.) in THF (300 mL) was added LDA (2 M, 116 mL, 1.5 eq.) at −78° C. and stirred for 1 hour, then DMF (34.1 g, 466 mmol, 3 eq.) was added at −78° C. and stirred for 2 hours. The reaction mixture was quenched by addition saturated ammonium chloride (200 mL) at 0° C., then diluted with water (300 mL) and extracted with ethyl acetate (1.00 L). The organic layer was washed by brine (200 mL), dried over anhydrous sodium sulfate, filtered and concentrated. The crude product was purified by column chromatography to give A-2-2 (20.0 g, 90.5 mmol, yield=58.2%) as yellow solid. $^1$H NMR (400 MHz, CDCl$_3$) δ=10.34 (s, 1H), 7.37-7.34 (m, 1H), 7.17-7.34 (m, 1H).

Step 2. A solution of A-2-2 (20.0 g, 90.5 mmol, 1.00 eq.) in THF (100 mL) and methanol (240 mL) was heated to 60° C., then a solution of sodium methylate (4.3 M, 25.3 mL, 1.2 eq.) in methanol was added and stirred at 60° C. for 12 hours. The reaction mixture was quenched by addition water (200 mL) and extracted with ethyl acetate (500 mL). The organic layer was washed by brine (100 mL), dried over anhydrous sodium sulfate, filtered and concentrated, and the residue was purified by column chromatography to give A-2-3 (13.5 g, 57.9 mmol, yield=64.0%) as a yellow solid. $^1$H NMR (400 MHz, CDCl$_3$) δ=10.30 (s, 1H), 7.20 (dd, J=7.6, 9.2 Hz, 1H), 6.86 (dd, J=4.0, 9.2 Hz, 1H), 3.84 (s, 3H).

Step 3. To a solution of A-2-3 (13.0 g, 55.8 mmol, 1.00 eq.) in DCM (150 mL) was added BBr$_3$ (28.0 g, 112 mmol, 2.00 eq.) at −40° C. drop-wise, then the mixture was stirred at 0° C. for 3 hours. The reaction mixture was quenched by addition methanol (20.0 mL) and saturated sodium bicarbonate solution (50.0 mL) at 0° C., then extracted with ethyl acetate (300 mL). The organic layer was washed by brine (100 mL), dried over anhydrous sodium sulfate, filtered and concentrated, and the residue was purified by column chromatography to give A-2-4 (10.5 g, 43.2 mmol, yield=77.4%) as a yellow solid. $^1$HNMR (400 MHz, CDCl$_3$) δ=11.78 (s, 1H), 10.35 (s, 1H), 7.32 (dd, J=7.6, 9.2 Hz, 1H), 6.96 (dd, J=4.0, 9.2 Hz, 1H).

General Method C.

Preparation of ethyl 2-amino-5-chloropyrazolo[1,5-a]pyrimidine-3-carboxylate (Δ-6-7)

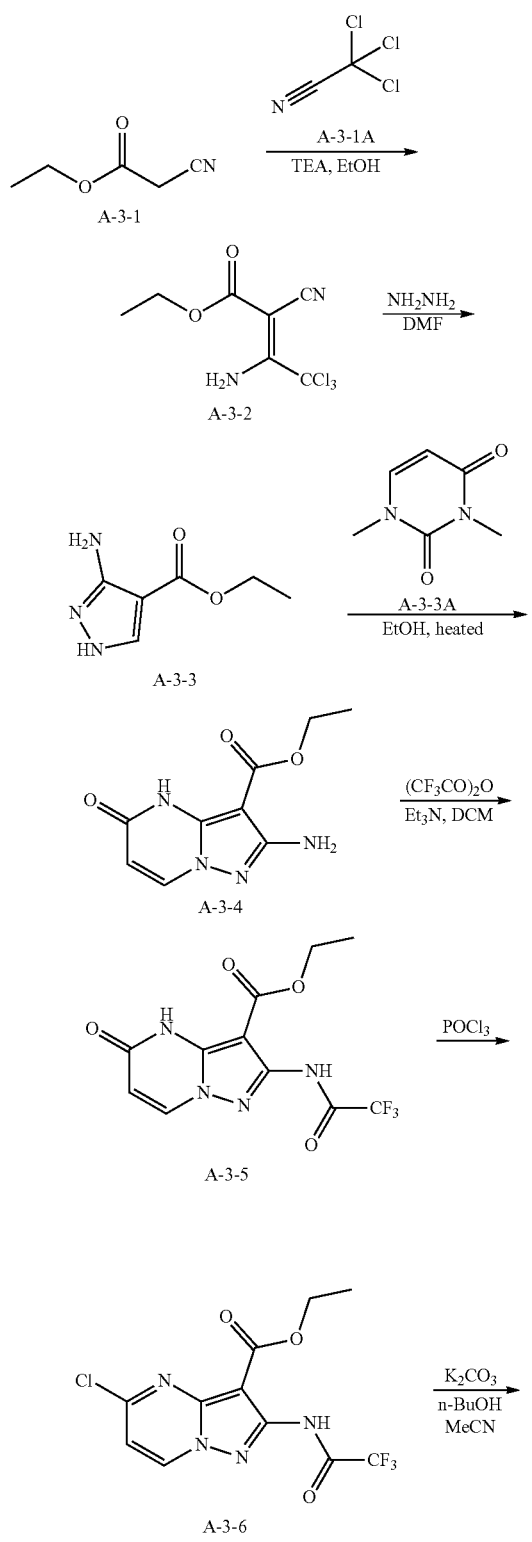

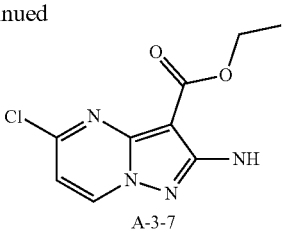

Step 1. To a solution of A-3-1 (100 g, 884 mmol, 1.00 eq.) and A-3-1A (230 g, 1.59 mol, 1.80 eq.) in ethanol (1.50 L) was added TEA (4.47 g, 44.2 mmol, 0.05 eq.) at 0° C. The mixture was stirred at 25° C. for 12 hours. The solvent was removed to give the crude product which was purified by column chromatography to give A-3-2 (200 g, 738 mmol, yield=83.5%) as off-white oil. $^1$H NMR (400 MHz, CDCl$_3$) δ=10.21 (br s, 1H), 6.95 (br s, 1H), 4.29-4.34 (m, 2H), 1.37 (t, J=7.2 Hz, 3H).

Step 2. To a solution of ethyl A-3-2 (100 g, 388 mmol, 1.00 eq.) in DMF (500 mL) was added hydrazine hydrate (311 g, 3.11 mol, 50.0% purity, 8.00 eq.). The mixture was stirred at 100° C. for 2 hours. Removed the solvent and added DCM (500 mL), the resulting mixture was stirred for 12 hours. The solid was filtered and washed with DCM (200 mL) to give A-3-3 (60.0 g, 317 mmol, yield=81.7%) as brown solid. $^1$H NMR (400 MHz, DMSO-d$_6$) δ=7.91 (s, 1H), 7.50 (s, 2H), 4.57 (s, 2H), 4.03 (q, J=7.2 Hz, 2H), 1.16 (t, J=7.2 Hz, 3H).

Step 3. To a solution of fresh prepared sodium ethoxide (0.50 M, 2.35 L, 4.00 eq.) in ethanol (200 mL) was added A-3-3 (50.0 g, 294 mmol, 1.00 eq.), then A-3-3A (41.2 g, 294 mmol, 1.00 eq.) was added. The mixture was stirred at 90° C. for 9 hours. Filtered and filter cake was washed with ethanol (100 mL) to give the A-3-4 (25.0 g, 113 mmol, yield=38.3%) as a brown solid. $^1$H NMR (400 MHz, DMSO-d$_6$) δ=7.71 (d, J=7.2 Hz, 1H), 5.57-5.46 (m, 3H), 4.15 (q, J=7.2 Hz, 2H), 1.25 (t, J=7.2 Hz, 3H).

Step 4. To a solution of A-3-4 (18.0 g, 81.0 mmol, 1.00 eq.) in DCM (300 mL) was added triethylamine (20.5 g, 202 mmol, 2.50 eq.) at 0° C., then trifluoroacetic anhydride (20.4 g, 97.2 mmol, 1.20 eq.) was added. The mixture was stirred at 25° C. for 12 hours. The solid was collected by filtration and washed with DCM (100 mL) to give A-3-5 (18.0 g, 47.4 mmol, yield=58.5%) as a yellow solid. LCMS:EW6129-170-P1D (M+1:319.1).

Step 5. A solution of A-3-5 (18.0 g, 56.6 mmol, 1.00 eq.) in fresh distilled POCl$_3$ (180 mL) was stirred at 100° C. for 5 hours. The mixture was poured into ice-water (500 mL) at 0° C., filtered and filter cake washed with water (200 mL) and then collected to give A-3-6 (15.0 g, 43.6 mmol, yield=77.1%) as a black brown solid. $^1$H NMR (400 MHz, DMSO-d$_6$) δ=11.93 (s, 1H), 9.31 (d, J=7.2 Hz, 1H), 7.47 (d, J=7.2 Hz, 1H), 4.28 (q, J=7.2 Hz, 2H), 1.28 (br t, J=7.2 Hz, 3H).

Step 6. To a solution of A-3-6 (13.0 g, 38.6 mmol, 1.00 eq.) in n-butanol (150 mL) and acetonitrile (150 mL) was added potassium carbonate (10.7 g, 77.2 mmol, 2.00 eq.). The mixture was stirred at 60° C. for 8 hours. The reaction mixture was quenched by addition water (200 mL) and extracted with dichloromethane/methanol=10/1 (500 mL×3). The combined organic layers were washed with brine (300 mL), dried over anhydrous sodium sulfate, filtered and concentrated under reduced pressure to give a residue. The residue was purified by Prep-HPLC (basic condition) to give the A-3-7 (4.8 g, 19.2 mmol, yield=49.6%) as white solid. $^1$H NMR (400 MHz, CDCl$_3$) δ=8.23 (d, J=7.2 Hz, 1H), 6.74 (d, J=7.2 Hz, 1H), 5.44 (s, 2H), 4.37 (q, J=7.2 Hz, 2H), 1.37 (t, J=7.2 Hz, 3H).

General Method D.

Preparation of ethyl 2-amino-5-((2-chloro-3-fluoro-6-hydroxybenzyl)(ethyl)amino)pyrazolo[1,5-a]pyrimidine-3-carboxylate (A-1)

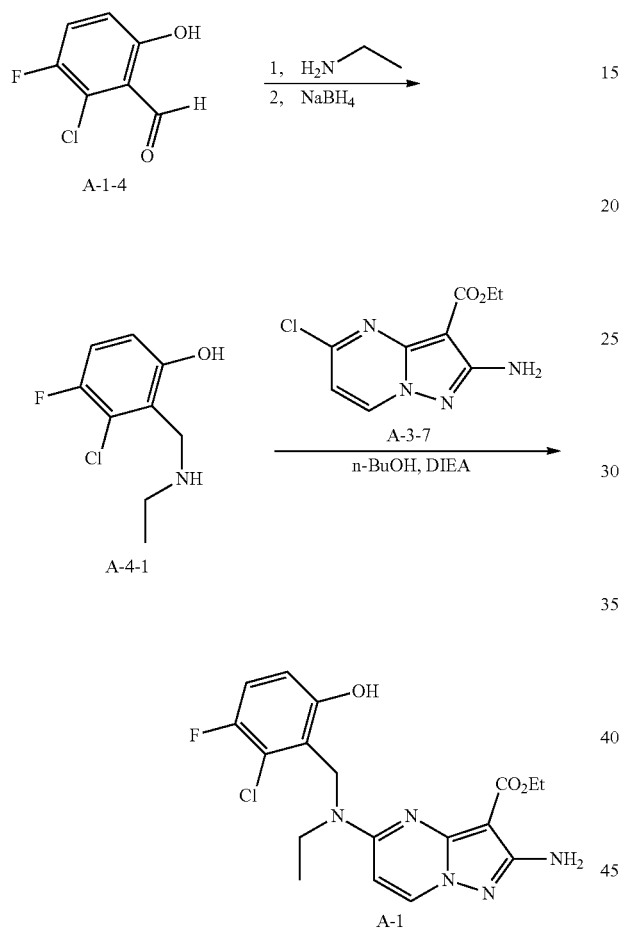

General Method E.

Preparation of ethyl 5-((2-cyano-6-hydroxybenzyl)(ethyl)amino)pyrazolo[1,5-a]pyrimidine-3-carboxylate (A-2)

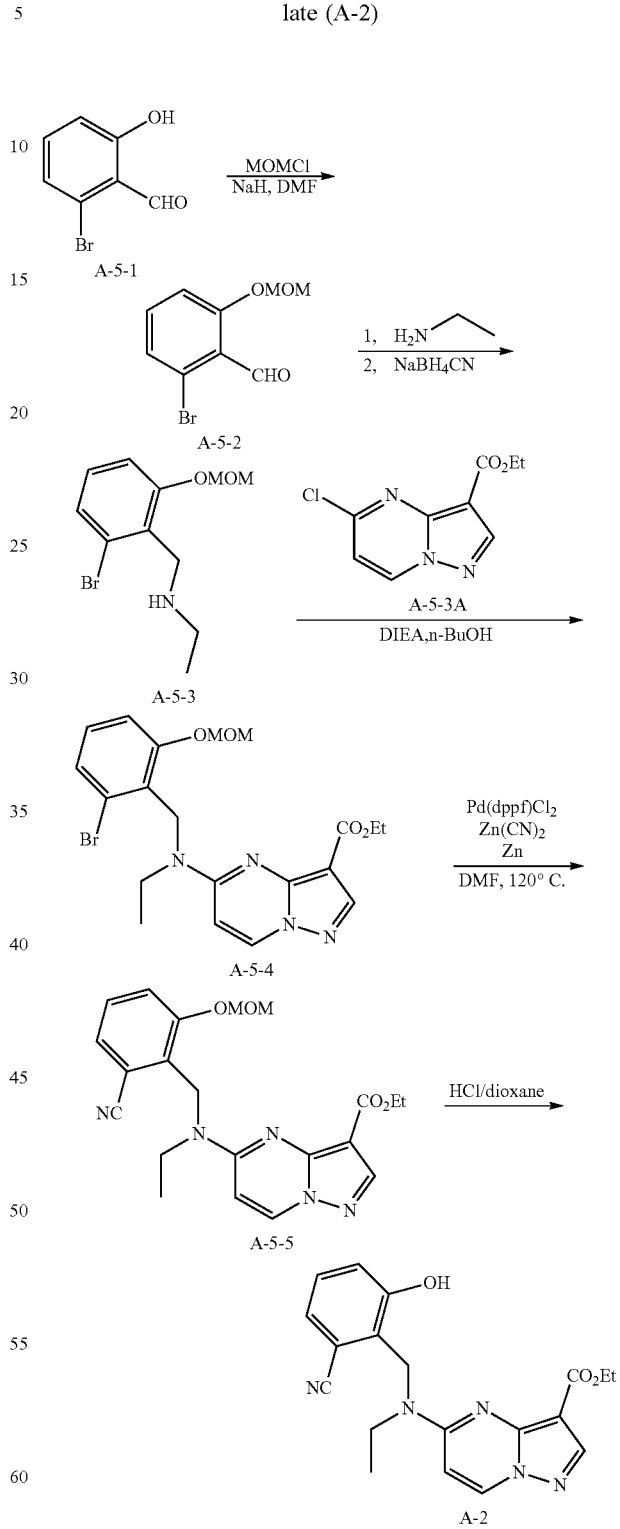

Step 1. A solution of A-1-4 (166 mg, 951 μmol, 1 eq.) and ethylamine (129 mg, 2.85 mmol, 3.0 eq.) in methanol (4.8 mL) was stirred for 1 hour at 65° C. The reaction mixture was cooled to room temperature and NaBH$_4$ (53 mg, 1.4 mmol, 1.5 eq.) was added, the reaction mixture was stirred at 25° C. for 30 min. The mixture was quenched with water (15 mL) and stirred for 5 min. The mixture was extracted with DCM (3×15 mL), dried with Na$_2$SO$_4$ and concentrated under reduced pressure. Flash chromatography (ISCO system, silica (12 g), 0-100% ethyl acetate in hexane) provide C$_9$H$_{11}$OFClN (175.3 mg, 860.8 μmol, 90.5% yield).

Step 2. To a mixture of A-4-1 (97.3 mg, 0.477 mmol, 1.15 eq.) and A-3-7 (100 mg, 0.415 mmol, 1.0 eq.) in n-butanol (2.00 mL) was added DIEA (269 mg, 2.1 mmol, 5.00 eq.). The mixture was heated to 85° C. and stirred for 20 hours. Removed the solvent and the residue was purified by column chromatography to give compound A-1 (146 mg, 357 μmol, yield=86%).

Step 1. To a solution of A-5-1 (2.00 g, 9.95 mmol, 1.00 eq.) in DMF (20.00 ML) was added sodium hydride (796 mg, 19.9 mmol, 60% purity, 2.00 eq.) at 0° C. under N$_2$ atmosphere. The mixture was stirred at 0° C. for 30 mins, then chloro(methoxy)methane (1.20 g, 14.92 mmol, 1.13 mL, 1.50 eq.) was added at 0° C. The mixture was stirred at 20° C. for 3 hours. Then the mixture was quenched by water (100 mL) and extracted with ethyl acetate (50.0 mL×3). The organic layer washed by brine (100 mL) and dried over anhydrous sodium sulfate, filtered and concentrated to give A-5-2 (2.70 g, crude) as a yellow solid. LCMS:EW6129-85-P1A(M+23:268.9).

Step 2. To a solution of A-5-2 (2.70 g, 11.0 mmol, 1.00 eq.) and ethanamine (745 mg, 16.5 mmol, 1.08 mL, 1.50 eq.) in methanol (20.0 mL) was added sodium acetate (1.08 g, 13.2 mmol, 1.20 eq.) in one portion at 20° C. under N₂ atmosphere. The mixture was stirred at 20° C. for 30 mins, then sodium cyanoborohydride (1.04 g, 16.5 mmol, 1.50 eq.) was added and stirred at 20° C. for 15 hours. The mixture was concentrated, diluted with water (30.0 mL) and extracted with ethyl acetate (15.0 mL×3). The combined organic layer washed by brine (30.0 mL), dried over anhydrous sodium sulfate, filtered and concentrated under reduced pressure to give A-5-3 (2.95 g, 10.7 mmol, yield=97.6%) as a yellow solid. LCMS:EW6129-100-P1B (M+1:274).

Step 3. To a solution of A-5-3 (2.95 g, 10.7 mmol, 1.00 eq.) and A-5-3A (2.43 g, 10.7 mmol, 1.00 eq.) in n-BuOH (20.0 mL) was added DIEA (5.56 g, 43.0 mmol, 7.51 mL, 4.00 eq.) in one portion at 20° C. under N₂ atmosphere. The mixture was heated to 95° C. and stirred for 2 hours. Then the mixture was diluted with water (50.0 mL) and extracted with ethyl acetate (30.0 mL×3). The organic layer washed by brine (50.0 mL) and dried over anhydrous sodium sulfate. The residue was purified by column chromatography (SiO₂, Petroleum ether/ethyl acetate=5/1 to 1:1) to give A-5-4 (1.66 g, 3.58 µmol, yield=33.3%) as a yellow solid. $^1$H NMR (400 MHz, CDCl₃) δ=8.32-8.28 (m, 2H), 7.30-7.28 (m, 1H), 7.17 (t, J=8.4 Hz, 1H), 7.14-7.08 (m, 1H), 6.55 (br s, 1H), 5.32-5.15 (m, 2H), 5.11 (s, 2H), 4.34 (q, J=7.2 Hz, 2H), 3.51 (s, 2H), 3.34 (s, 3H), 1.38 (t, J=7.2 Hz, 3H), 1.14 (t, J=7.2 Hz, 3H).

Step 4. To a solution of A-5-4 (1.50 g, 3.24 mmol, 1.00 eq.) in DMF (20.0 mL) was added Pd(dppf)Cl₂ (237 mg, 324 µmol, 0.10 eq.), Zn(CN)₂ (570 mg, 4.86 mmol, 308 µL, 1.50 eq.) and Zn (10.6 mg, 162 µmol, 0.05 eq.) at 20° C. under N₂ atmosphere. The mixture was heated to 120° C. and stirred for 15 hours. The mixture was diluted with water (100 mL) and extracted with ethyl acetate (50.0 mL×3). The organic layer was combined and washed by brine (100 mL) and dried over anhydrous sodium sulfate. The residue was purified by column chromatography (SiO₂, Petroleum ether/ethyl acetate=10/1 to 1:1) to give A-5-5 (830 mg, 2.03 mmol, yield=62.7%) as a yellow oil. LCMS:EW6129-107-PA(M+1:410.2).

Step 5. To a solution of A-5-5 (730 mg, 1.78 mmol, 1.00 eq.) in HC/dioxane (30.0 mL) was stirred at 20° C. for 3 hours. The reaction mixture was concentrated under reduced pressure to give A-2 (630 mg, 1.72 mmol, yield=96.6%) as a white solid. $^1$H NMR (400 MHz, CDCl₃) δ=10.84 (br s, 1H), 8.37 (d, J=7.6 Hz, 1H), 8.34 (s, 1H), 7.36-7.31 (m, 1H), 7.24-7.20 (m, 2H), 6.44 (br d, J=7.6 Hz, 1H), 5.14 (s, 2H), 4.43 (q, J=7.2 Hz, 2H), 3.72-3.67 (m, 2H), 1.40 (t, J=7.2 Hz, 3H), 1.34 (t, J=7.2 Hz, 3H).

General Method F

Preparation of ethyl 5-((2-bromo-3-fluoro-6-hydroxybenzyl)(ethyl)amino)pyrazolo[1,5-a]pyrimidine-3-carboxylate (A-3)

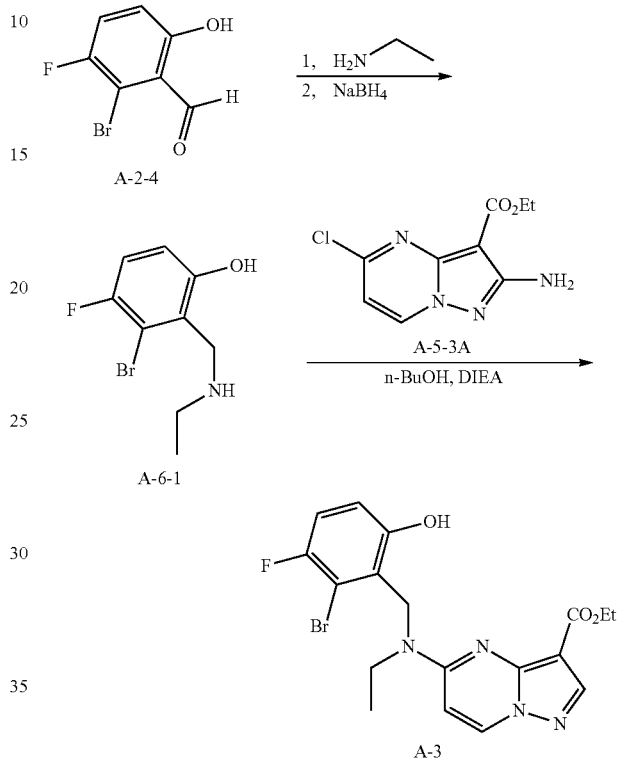

Step 1. A solution of A-2-4 (3.00 g, 13.7 mmol, 1 eq.) and ethanamine (1.24 g, 27.4 mmol, 2.00 eq.) in methanol (30.0 mL) was stirred for 30 min at 25° C. and then NaBH₄ (1.04 g, 27.4 mmol, 2.00 eq.) was added, the reaction mixture was stirred at 25° C. for 12 hours. The solvent was removed and the result mixture was diluted with water (20 mL), extracted with ethyl acetate (100 mL). The organic layer was washed by brine (100 mL), dried over anhydrous sodium sulfate, filtered and concentrated to give A-6-1 (2.40 g, 8.71 mmol, yield=63.6%) as a white solid. $^1$HNMR (400 MHz, CDCl₃) δ=6.93 (t, J=8.4 Hz, 1H), 6.71 (dd, J=4.4, 8.4 Hz, 1H), 4.23 (s, 2H), 2.76 (q, J=7.2 Hz, 2H), 1.19 (t, J=7.2 Hz, 3H).

Step 2. To a mixture of A-6-1 (1.20 g, 4.84 mmol, 1.00 eq.) and A-5-3A (1.31 g, 5.80 mmol, 1.20 eq.) in n-butanol (10.0 mL) was added DIEA (2.50 g, 19.4 mmol, 4.00 eq.) in one portion at 25° C. under N₂ protecting. The mixture was heated to 95° C. and stirred for 2 hours. Removed the solvent and the residue was purified by column chromatography to give compound A-3 (1.20 g, 2.37 mmol, yield=49.0%) as a white solid. $^1$HNMR (400 MHz, CDCl₃) δ=10.40 (s, 1H), 8.37-8.29 (m, 2H), 7.03 (dd, J=8.0, 8.8 Hz, 1H), 6.88 (dd, J=4.8, 8.8 Hz, 1H), 6.40 (d, J=8.0 Hz, 1H), 5.18 (br s, 2H), 4.40 (q, J=7.2 Hz, 2H), 3.65 (q, J=7.2 Hz, 2H), 1.38 (t, J=7.2 Hz, 3H), 1.31 (t, J=7.2 Hz, 3H).

General Method G.

Preparation of ethyl 2-amino-5-((2-bromo-3-fluoro-6-hydroxybenzyl)(ethyl)amino)pyrazolo[1,5-a]pyrimidine-3-carboxylate (A-4)

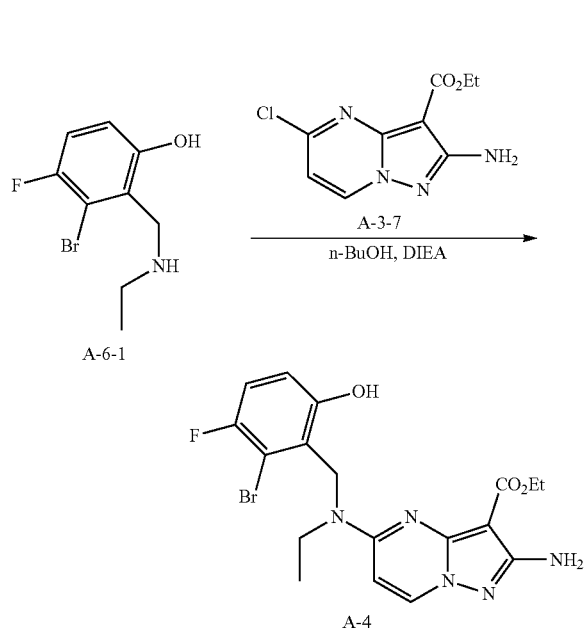

Step 1. To a mixture of A-6-1 (0.30 g, 1.21 mmol, 1.00 eq.) and A-3-7 (349 mg, 1.45 mmol, 1.2 eq.) in n-butanol (5.00 mL) was added DIEA (625 mg, 4.84 mmol, 4.00 eq.) in one portion at 25° C. under $N_2$ protecting. The mixture was heated to 95° C. and stirred for 2 hours. Removed the solvent and the residue was purified by column chromatography to give compound A-4 (250 mg, 514 μmol, yield=42.5%) as a yellow solid. $^1$HNMR (400 MHz, $CDCl_3$) δ=(br s, 1H), 8.05 (d, J=7.6 Hz, 1H), 7.04 (dd, J=8.0, 8.8 Hz, 1H), 6.85 (dd, J=4.8, 8.8 Hz, 1H), 6.18 (d, J=7.8 Hz, 1H), 5.29 (s, 2H), 5.16 (br s, 2H), 4.40 (q, J=7.2 Hz, 2H), 3.58 (q, J=7.2 Hz, 2H), 1.39 (t, J=7.2 Hz, 3H), 1.29 (t, J=7.2 Hz, 3H).

Preparation of ethyl 2-amino-5-((2-bromo-6-hydroxybenzyl)(ethyl)amino)pyrazolo[1,5-a]pyrimidine-3-carboxylate (A-5)

General method F and G were used to make A-5 starting with A-5-1 in general method E.

Preparation of ethyl 2-amino-5-((2-bromo-3-fluoro-6-hydroxybenzyl)(cyclopropylmethyl)amino)pyrazolo[1,5-a]pyrimidine-3-carboxylate (A-6)

General method D was used to make A-6.

Preparation of ethyl 2-amino-5-((2-bromo-3-fluoro-6-hydroxybenzyl)(isopropyl)amino)pyrazolo[1,5-a]pyrimidine-3-carboxylate (A-7)

General method D was used to make A-7.
General Method H.

Preparation of ethyl 2-amino-5-{[(2-bromo-3-fluoro-6-hydroxyphenyl)methyl]amino}pyrazolo[1,5-α]pyrimidine-3-carboxylate (A-8)

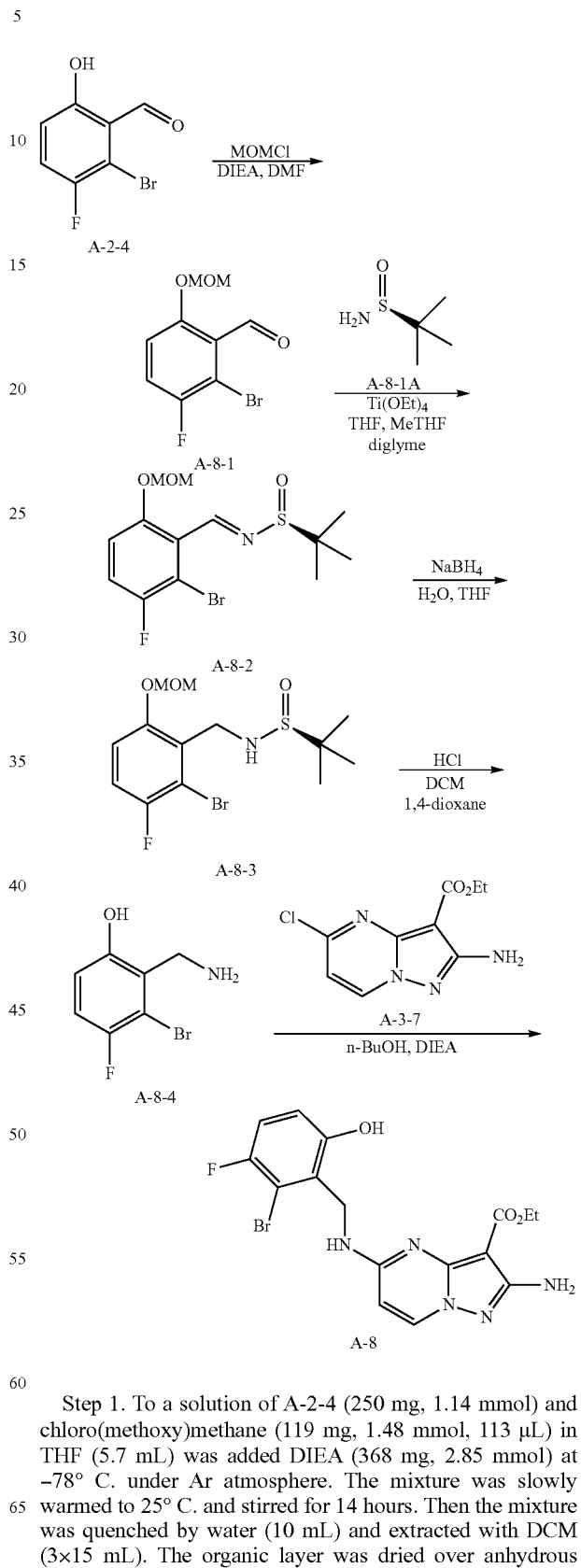

Step 1. To a solution of A-2-4 (250 mg, 1.14 mmol) and chloro(methoxy)methane (119 mg, 1.48 mmol, 113 μL) in THF (5.7 mL) was added DIEA (368 mg, 2.85 mmol) at −78° C. under Ar atmosphere. The mixture was slowly warmed to 25° C. and stirred for 14 hours. Then the mixture was quenched by water (10 mL) and extracted with DCM (3×15 mL). The organic layer was dried over anhydrous sodium sulfate, filtered and concentrated. Flash chromatography (ISCO system, silica (12 g), 5-15% ethyl acetate in hexane) provided A-8-1 (96.6 mg, 32% yield).

Step 2. To a solution of A-8-1-(96.6 mg, 0.367 mmol) and A-8-1A (111 mg, 0.918 mmol) in THF (1.0 mL), Me-THF (1.0 mL) and diglyme (52 µL) was added Ti(OEt)$_4$ (586 mg, 2.57 mmol, 538 µL) under Ar atmosphere. The mixture was heated to 75° C. and stirred for 2 hours. The mixture was cooled to room temperature and poured into a 5:1 MOH: water solution (60 mL). To this suspension was added celite and the mixture filtered through abed a celite. The celite pad was washed with MeOH (50 mL) and ethyl acetate (50 m). Combined filtrates were added to water (100 mL) and the mixture extracted with ethyl acetate (3×75 mL). The combined organic extracts were washed with brine (50.0 mL), dried over anhydrous sodium sulfate, filtered and concentrated under reduced pressure. Flash chromatography (ISCO system, silica (12 g), 0-30% ethyl acetate in hexane) provided A-8-2 (101.6 mg, 75% yield).

Step 3. To a solution of A-8-2 (101.6 mg, 0.28 mmol) and water (15.0 mg, 0.83 mmol) in THF (1.4 mL) at −78° C. was added NaBH$_4$ (31.5 mg, 0.83 mmol) in one portion. The mixture was slowly warmed to 25° C. and stirred for 14 hours. Then the mixture was cooled to −20° C. and quenched with water (10.0 mL) and extracted with DCM (3×15 mL). Combined extracts were dried with Na$_2$SO$_4$ then concentrated under reduced pressure. Flash chromatography (ISCO system, silica (12 g), 30-60% ethyl acetate in hexane) provided A-8-3 (quantitative).

Step 4. To a solution of A-8-3 (102 mg, 0.28 mmol, 1.00 eq.) in DCM (4.0 mL) was added 4M HCl in dioxane (3.0 mL). The reaction mixture was stirred at 25° C. for 1.5 hours then concentrated under reduced pressure. The solids were suspended in DCM (5 mL) and saturated bicarbonate solution (5 mL) was added and the mixture stirred for 5 min. The mixture was extracted with DCM (3×15 mL). Combined extracts were dried with Na$_2$SO$_4$ then concentrated under reduced pressure. Flash chromatography (ISCO system, silica (4 g), 80-100% ethyl acetate in hexane) provided A-8-4 (53.5 mg, 88% yield).

Step 5. General method G was used to make A-8 starting with A-8-4.

| Compd # | Structure | MS m/z |
|---|---|---|
| A-1 | | 408.1 |
| A-2 | | 366.1 |
| A-3 | 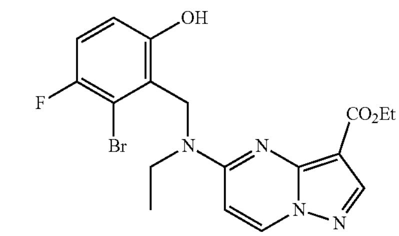 | 437.0 |
| A-4 | 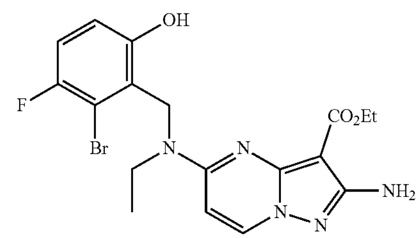 [SMILES: CCOC(=O)c1c(N)nn2ccc(N(CC)Cc3c(O)ccc(F)c3Cl)nc12] | 452.3 |
| A-5 | 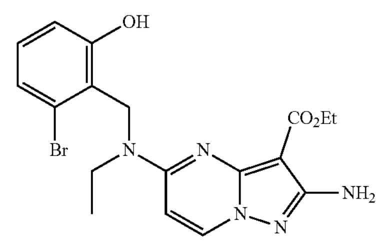 [SMILES: CCOC(=O)c1c(N)nn2ccc(N(CC)Cc3c(O)cccc3Br)nc12] | 434.2 |
| A-6 | 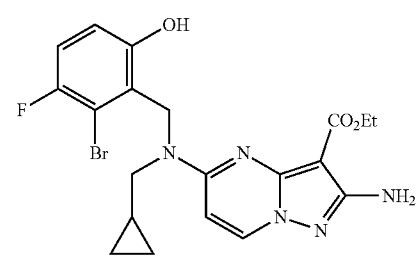 [SMILES: CCOC(=O)c1c(N)nn2ccc(N(Cc3c(O)ccc(F)c3Br)CC3CC3)nc12] | 478.3 |
| A-7 | 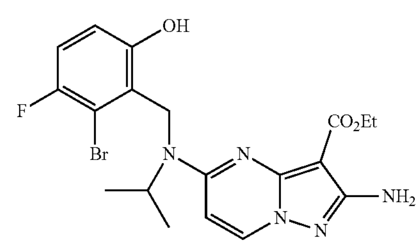 [SMILES: CCOC(=O)c1c(N)nn2ccc(N(Cc3c(O)ccc(F)c3Br)C(C)C)nc12] | 466.0 |
| A-8 | 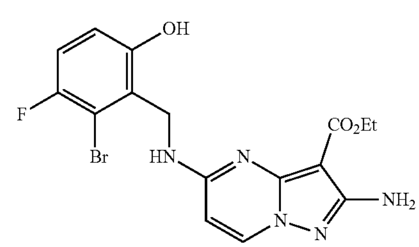 [SMILES: CCOC(=O)c1c(N)nn2ccc(NCc3c(O)ccc(F)c3Br)nc12] | 424.0 |

General Method H.

Preparation of (7S)-3-amino-12-chloro-14-ethyl-11-fluoro-7-methyl-6,7,13,14-tetrahydro-1,15-ethenopyrazolo[4,3-f][1,4,8,10]benzoxatriazacyclotridecin-4(5H)-one (1)

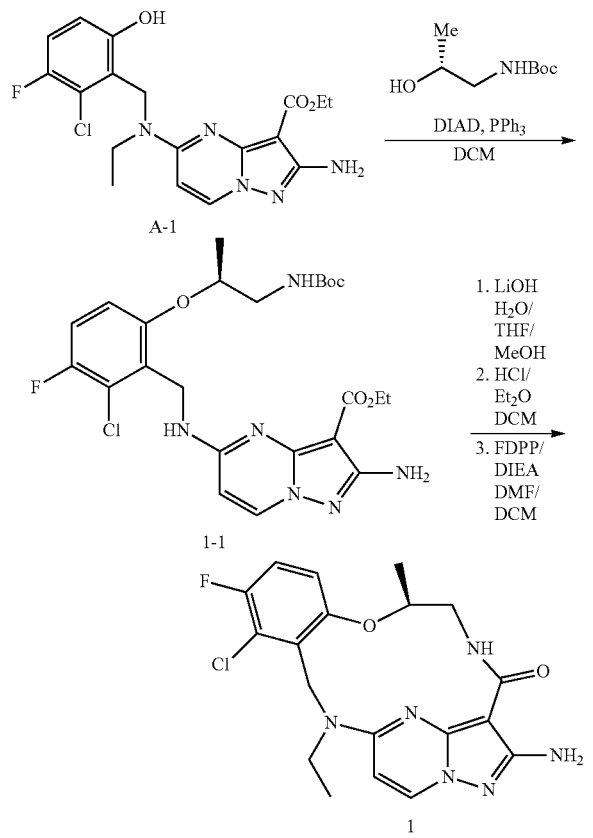

Step 1. To a solution of azeotrope dried phenol A-1 (50 mg, 0.12 mmol) and (R)-tert-butyl (2-hydroxypropyl)carbamate (25.8 mg, 0.147 mmol) in dichloromethane (300 µL) was added PPh3 (40.2 g, 0.153 mmol). The mixture was stirred until completely dissolved then cooled to 0° C. and DIAD (32.2 mg, 0.159 mmol, 31.3 µL) was added dropwise with mixing. The mixture was warmed to 35° C. and stirred for 1 hour. Flash chromatography (ISCO system, silica (12 g), 0-100% ethyl acetate in hexane) provided impure 1-1.

Step 2. To a solution of 1-7 (69.2 mg, 122 µmol) in MeOH (4 mL) and THF (2 mL) at ambient temperature was added aqueous LiOH solution (2.0 M, 2 mL). The mixture was heated at 70° C. for 25 hours, cooled to −20° C. then quenched with aqueous HCl solution (2.0 M) to acidic. The mixture was extracted with DCM (3×5 mL), dried with Na2SO4 concentrated under reduced pressure, and dried under high vacuum. The crude material was dissolved in DCM (4 mL) followed by addition of HCl in 1,4-dioxane (4 M, 3 mL). The mixture was stirred ambient temperature for 1 hour, concentrated under reduced pressure, and dried under high vacuum. The crude material was dissolved in DMF (2.0 mL) and DCM (8.0 mL) and Hünig's base (158 mg, 1.22 mmol, 213 µL) then FDPP (61.2 mg, 159 µmol) was added in one portion. The reaction was stirred for 3 hours then quenched with 2 M Na2CO3 solution (5 mL). Mixture was stirred for 5 min then extracted with DCM (4×10 mL). Combined extracts were dried with Na2SO4 and concentrated under reduced pressure. Flash chromatography (ISCO system, silica (12 g), 0-7.5% methanol in dichloromethane) provided 1 (11.1 mg, 26.5 µmol, 21% yield).

General Method I.

Preparation of (7S)-14-ethyl-7-methyl-4-oxo-4,5,6,7,13,14-hexahydro-1,15-ethenopyrazolo[4,3-f][1,4,8,10]benzoxatriazacyclotridecine-12-carbonitrile (2)

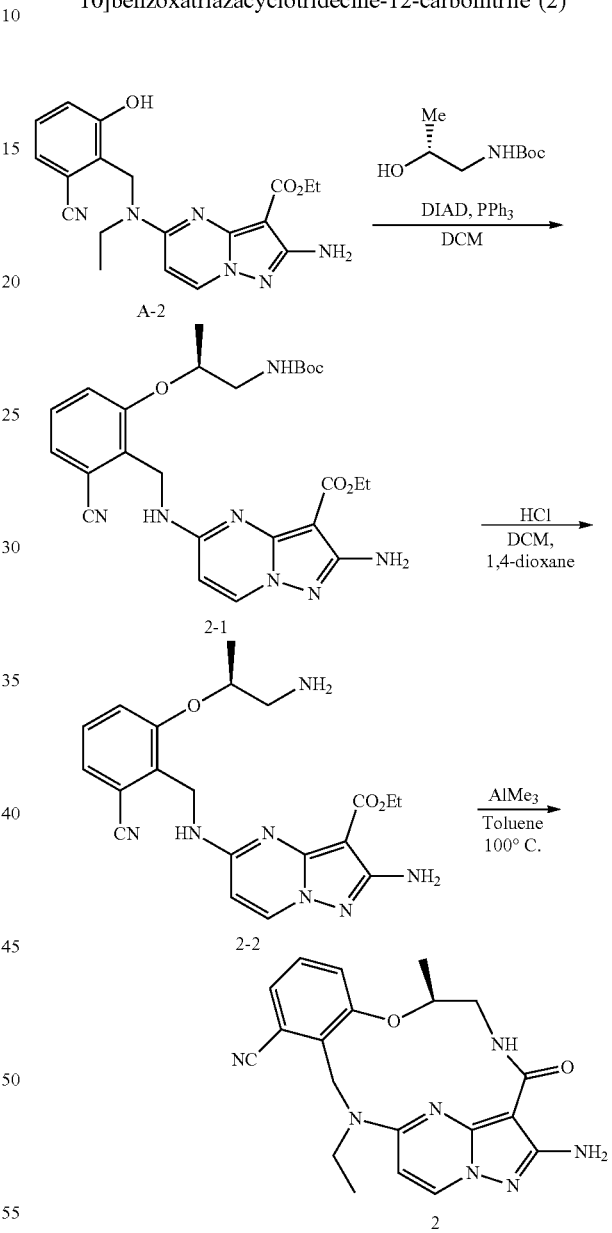

Step 1. To a solution of azeotrope dried phenol A-2 (100 mg, 0.274 mmol) and (R)-tert-butyl (2-hydroxypropyl)carbamate (95.9 mg, 0.547 mmol) in dichloromethane (182 µL) was added PPh3 (144 mg, 0.547 mmol). The mixture was stirred until completely dissolved then cooled to 0° C. and DIAD (116 mg, 0.574 mmol, 113 µL) was added dropwise with mixing. The mixture was warmed to 35° C. and stirred for 18 hours. Flash chromatography (ISCO system, silica (12 g), 0-80% ethyl acetate in hexane) provided 2-1. (81.1 mg, 155 µmol, 56% yield).

Step 2. To a solution of 2-1 (81.1 mg, 155 µmol) in DCM (1.5 mL) was added HCl in 1,4-dioxane (4 M, 1.5 mL). The mixture was stirred ambient temperature for 1 hour, concentrated under reduced pressure, and dried under high vacuum to provide 2-2.

Step 3. To a solution of 2-2 (65.6 mg, 155 µmol) in toluene (3.1 mL) was added trimethylaluminum in THF (2 M, 465 µL). The mixture was heated to 100° C. and stirred for 1 hour. The mixture was cooled to room temperature and quenched with 2.0 N aqueous HC (4 mL), diluted with water (10 mL) and extracted with ethyl acetate (3×10 mL). Combined organic layers was washed with brine and dried over sodium sulfate and concentrated under reduced pressure. Flash chromatography (ISCO system, silica (12 g), 0-10% methanol in dichloromethane) provided 2. (29.0 mg, 77 µmol, 49% yield).

Compound 3 was prepared according to General Method I.

General Method J.

Preparation of (7S)-14-ethyl-11-fluoro-7-methy-4-oxo-4,5,6,7,13,14-hexahydro-1,15-ethenopyrazolo[4,3-f][1,4,8,10]benzoxatriazacyclotridecine-12-carbonitrile (4)

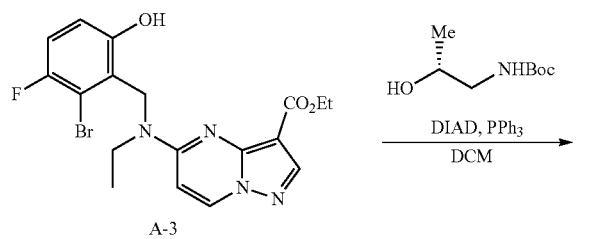

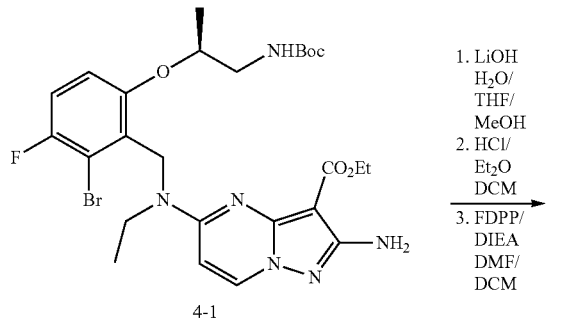

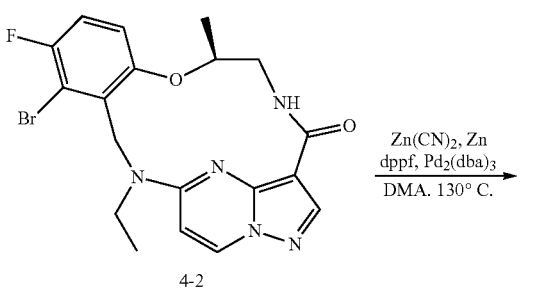

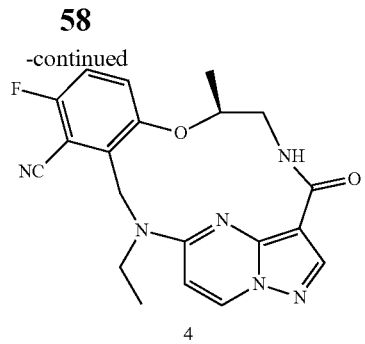

Step 1. A-3 was converted to 4-1 following step 1 in general method H.

Step 2. 4-1 was converted to 4-2 following step 2 in general method H.

Step 3. To a degassed mixture of 4-2 (8.0 mg, 17.9 µmol), Zn(CN)$_2$ (10.5 mg, 8i9.2 µmol), Zn (0.12 mg, 1.8 µmol) and dppf (3.96 mg, 7.14 µmol) in DMA (1.12 mL) was added Pd$_2$(dba)$_3$ (3.3 mg, 3.6 µmol). The mixture was heated to 130° C. for 3 hours. The reaction was cooled and water (3 mL) added followed by extracted with dichloromethane (3×3 mL) Combined extracts were dried with Na$_2$SO$_4$ then concentrated under reduced pressure. Flash chromatography (ISCO system, silica (12 g), 0-5% methanol in dichloromethane) followed by reverse phase purification ISCO system, C18 (50 g, gold), 0-100% acetonitrile in water w/0.035% TFA) provided 4 (6.7 g, 16.7 µmol, 95% yield).

Compound 5 through 9 were prepared according to General Method I and J starting with A-4 through A-8 respectively.

General Method K.

Preparation of tert-butyl 2-amino-5-[(4-methylbenzene-1-sulfonyl)oxy]pyrazolo[1,5-α]pyrimidine-3-carboxylate (A-10-5)

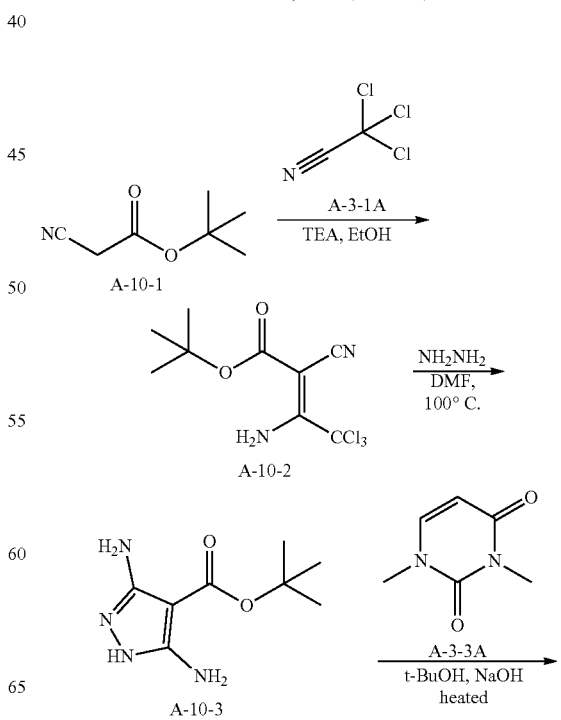

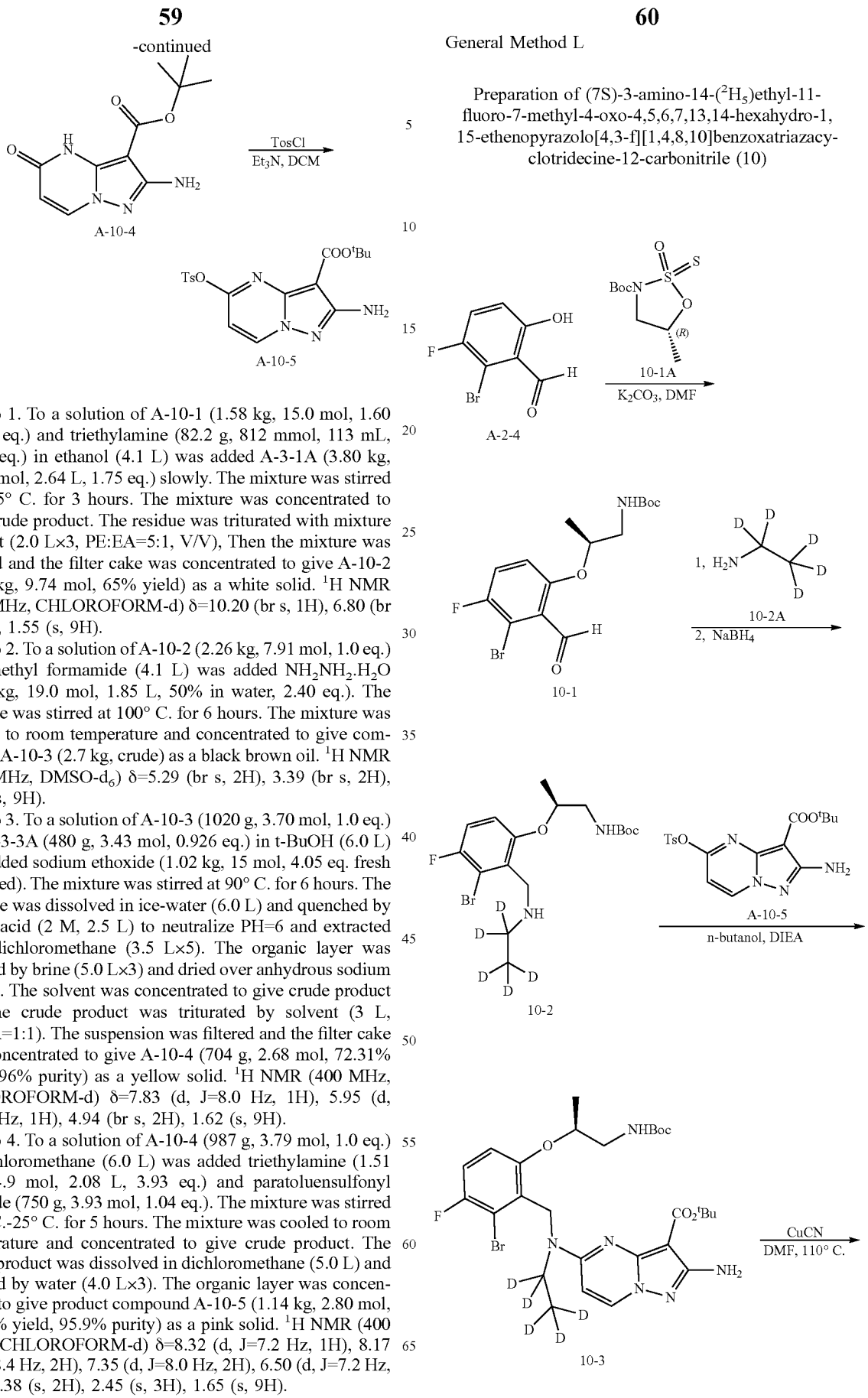

General Method L

Preparation of (7S)-3-amino-14-($^2H_5$)ethyl-11-fluoro-7-methyl-4-oxo-4,5,6,7,13,14-hexahydro-1,15-ethenopyrazolo[4,3-f][1,4,8,10]benzoxatriazacyclotridecine-12-carbonitrile (10)

Step 1. To a solution of A-10-1 (1.58 kg, 15.0 mol, 1.60 L, 1.0 eq.) and triethylamine (82.2 g, 812 mmol, 113 mL, 0.054 eq.) in ethanol (4.1 L) was added A-3-1A (3.80 kg, 26.30 mol, 2.64 L, 1.75 eq.) slowly. The mixture was stirred at 0-25° C. for 3 hours. The mixture was concentrated to give crude product. The residue was triturated with mixture solvent (2.0 L×3, PE:EA=5:1, V/V), Then the mixture was filtered and the filter cake was concentrated to give A-10-2 (2.78 kg, 9.74 mol, 65% yield) as a white solid. $^1$H NMR (400 MHz, CHLOROFORM-d) δ=10.20 (br s, 1H), 6.80 (br s, 1H), 1.55 (s, 9H).

Step 2. To a solution of A-10-2 (2.26 kg, 7.91 mol, 1.0 eq.) in dimethyl formamide (4.1 L) was added NH$_2$NH$_2$.H$_2$O (1.91 kg, 19.0 mol, 1.85 L, 50% in water, 2.40 eq.). The mixture was stirred at 100° C. for 6 hours. The mixture was cooled to room temperature and concentrated to give compound A-10-3 (2.7 kg, crude) as a black brown oil. $^1$H NMR (400 MHz, DMSO-d$_6$) δ=5.29 (br s, 2H), 3.39 (br s, 2H), 1.47 (s, 9H).

Step 3. To a solution of A-10-3 (1020 g, 3.70 mol, 1.0 eq.) and A-3-3A (480 g, 3.43 mol, 0.926 eq.) in t-BuOH (6.0 L) was added sodium ethoxide (1.02 kg, 15 mol, 4.05 eq. fresh Prepared). The mixture was stirred at 90° C. for 6 hours. The mixture was dissolved in ice-water (6.0 L) and quenched by acetic acid (2 M, 2.5 L) to neutralize PH=6 and extracted with dichloromethane (3.5 L×5). The organic layer was washed by brine (5.0 L×3) and dried over anhydrous sodium sulfate. The solvent was concentrated to give crude product and the crude product was triturated by solvent (3 L, PE:EA=1:1). The suspension was filtered and the filter cake was concentrated to give A-10-4 (704 g, 2.68 mol, 72.31% yield, 96% purity) as a yellow solid. $^1$H NMR (400 MHz, CHLOROFORM-d) δ=7.83 (d, J=8.0 Hz, 1H), 5.95 (d, J=8.0 Hz, 1H), 4.94 (br s, 2H), 1.62 (s, 9H).

Step 4. To a solution of A-10-4 (987 g, 3.79 mol, 1.0 eq.) in dichloromethane (6.0 L) was added triethylamine (1.51 kg, 14.9 mol, 2.08 L, 3.93 eq.) and paratoluensulfonyl chloride (750 g, 3.93 mol, 1.04 eq.). The mixture was stirred at 0° C.-25° C. for 5 hours. The mixture was cooled to room temperature and concentrated to give crude product. The crude product was dissolved in dichloromethane (5.0 L) and washed by water (4.0 L×3). The organic layer was concentrated to give product compound A-10-5 (1.14 kg, 2.80 mol, 73.79% yield, 95.9% purity) as a pink solid. $^1$H NMR (400 MHz, CHLOROFORM-d) δ=8.32 (d, J=7.2 Hz, 1H), 8.17 (d, J=8.4 Hz, 2H), 7.35 (d, J=8.0 Hz, 2H), 6.50 (d, J=7.2 Hz, 1H), 5.38 (s, 2H), 2.45 (s, 3H), 1.65 (s, 9H).

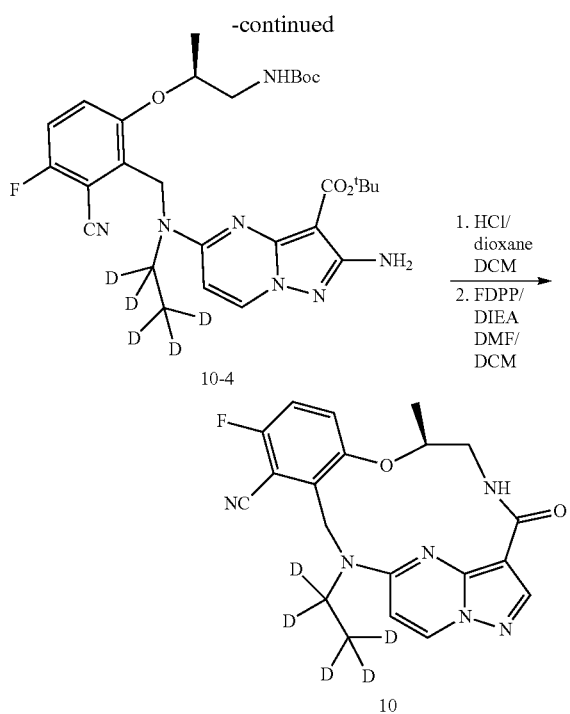

Step 1. A solution of A-2-4 (1.0 g, 4.57 mmol), 10-1A (1.14 g, 4.79 mmol) and K₂CO₃ (1.89 g, 13.7 mmol) in DMF (15 mL) was stirred for 3 hours at 25° C. The reaction mixture was diluted with DCM (100 mL) and water (75 mL) and adjusted till acidic with 20% citric acid solution and stirred vigorously for 10 min. The organic layer was removed and the aqueous layer extracted with DCM (2×25 mL). The combined extracts were washed with brine (50 mL), dried over anhydrous sodium sulfate, filtered and concentrated to dryness. Flash chromatography (ISCO system, silica (80 g), 10-40% ethyl acetate in hexane) provided 10-1 (1.70 g, 99% yield).

Step 2. A solution of 10-1 (4.09 g, 10.9 mmol) and 10-2A (1.8 g, 35.9 mmol) in dry methanol (54 mL) was stirred for 1 hour at 50° C. Reaction was cooled to room temperature and NaBH₄ (822 mg, 21.7 mmol) was added. The reaction mixture was stirred for 14 hours then quenched with water (75 mL). The mixture was extracted with DCM (3×75 mL). The combined extracts were washed with brine (50 mL), dried over anhydrous sodium sulfate, filtered and concentrated. Flash chromatography (ISCO system, silica (40 g), 10-80% ethyl acetate in hexane) provided 10-2 (4.05 g, 90% yield).

Step 3. To a mixture of A-10-5 (2.8 g, 6.92 mmol), 10-2 (2.98 g, 7.27 mmol) and molecular sieve (3 g) in n-butanol (10.0 mL) was added DIEA (4.47 g, 34.6 mmol). The mixture was heated to 90° C. and stirred for 26 hours. The reaction was cooled and diluted with DCM (100 mL) then filtered through celite. The filtrate was washed with 1 M Na₂CO₃ solution (50 mL) then brine (50 mL) and dried over anhydrous sodium sulfate, filtered and concentrated. Flash chromatography (ISCO system, silica (120 g), 0-60% ethyl acetate in dichloromethane) provided 10-3 (4.07 g, 91% yield).

Step 4. To a degassed solution of 10-3 (4.07 g, 6.33 mmol) in DMF (12.6 mL) was added CuCN (850 mg, 9.5 mmol). The mixture was heated to 110° C. and stirred for 39 hours. The reaction was cooled and diluted with DCM (15 mL) then 6 M NH₄OH solution (50 mL) was added. The mixture was stirred vigorously for 15 min then extracted with DCM (4×35 mL) and combined extracts were again mixed vigorously with a 6 M NH₄OH solution (50 mL) for 30 min extracted with DCM (3×50 mL) and repeated treatment with NH₄OH solution 2 more time. Combined extracts were dried with brine (50 mL) then Na₂SO₄ and concentrated under reduced pressure. Flash chromatography (ISCO system, silica (120 g), 20-60% ethyl acetate in dichloromethane) followed by reverse phase purification (ISCO system, C18 (50 g, gold), 0-100% acetonitrile in water w/0.035% TFA, 6 injections) provided 10-4 (2.82 g, 75% yield).

Step 5. To a solution of 10-4 (2.82 mg, 4.80 mmol) in DCM (25 mL) was added HCl in 1,4-dioxane (4 M, 20 mL, 80 mmol). The mixture was stirred ambient temperature for 16 hours, concentrated under reduced pressure, and dried under high vacuum. The crude material was dissolved in in DMF (10 mL) and DCM (60 mL) and Hünig's base (1.56 g, 120 mmol, 21 mL) then FDPP (2.02 g, 5.27 mmol) was added in one portion. The reaction was stirred for 87 hours then quenched with 2 M Na₂CO₃ solution (100 mL). Mixture was stirred for 5 min then extracted with DCM (3×150 mL). Combined extracts were washed with 2 M Na₂CO₃ solution (100 mL), brine (100 mL) and dried with Na₂SO₄ and concentrated under reduced pressure. Flash chromatography (ISCO system, silica (120 g), 1.25-6.25% methanol in dichloromethane) provided 10 (1.59 g, 79% yield).

General Method M

Preparation of (7R)-3-amino-14-ethyl-11-fluoro-7-methyl-4-oxo-4,5,6,7,13,14-hexahydro-1,15-etheno-pyrazolo[4,3-f][1,4,8,10]benzoxatriazacyclotridecine-12-carbonitrile (11)

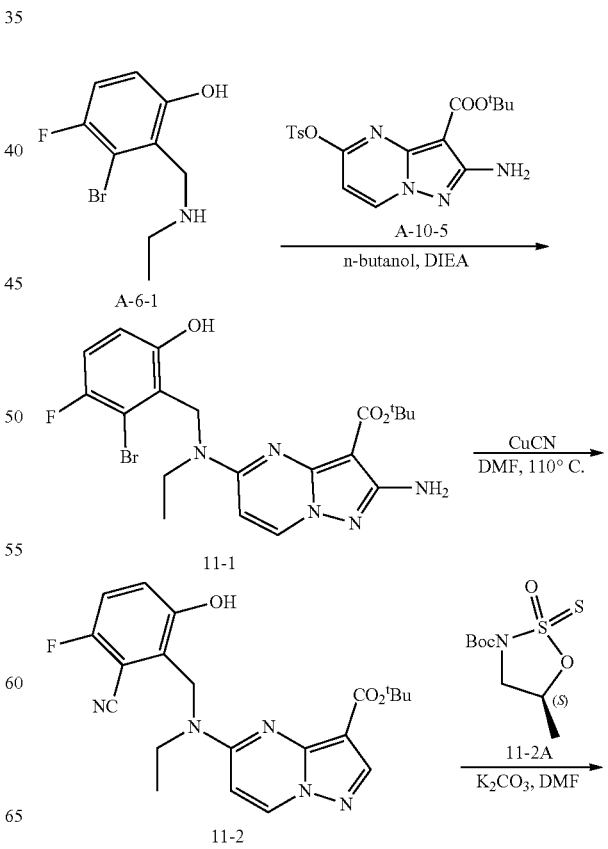

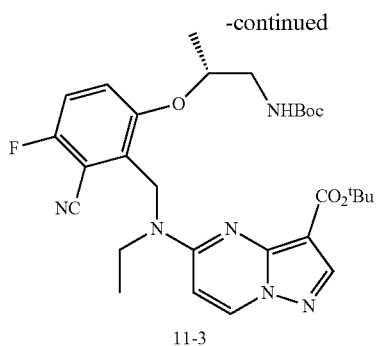

11-3

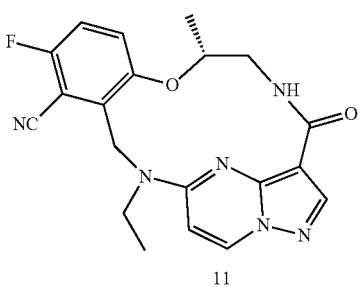

11

Step 1. To a solution of A-6-1 (438.42 g, 1.70 mol, 1.0 eq.) and A-10-5 (690 g, 1.70 mol, 1.0 eq.) in n-BuOH (6.0 L) was added diisopropylethylamine (742 g, 5.74 mol, 1.0 L, 3.38 eq.) and 4A MS (200 g). The mixture was stirred at 90° C. for 8 hours. TLC (PE:EA=1:1) showed the compound 7 was consumed and two new spots were found. The mixture was filtered at 50° C. and the filtrate was quenched by water (8.0 L) and extracted with ethyl acetate (4.0 L×3). The organic layer washed by brine (4.0 L×3), dried over anhydrous sodium sulfate and concentrated to give crude product. The filter cake was stirred in n-BuOH (2.0 L) at 90° C. for 1 hour, then filtered at 50° C., repeated this work up for three times until no desired product remained which monitored by TLC, then the filtrate was concentrated to give crude product. All the residues were triturated with mixture solvent [500 mL×3; ethyl actate:petroleum ether=1:2 (v/v)] and the mother liquid was purified by column chromatography (SiO$_2$, Petroleum ether/Ethyl acetate=10/1 to 0:1) to give 11-1 (570 g, 1.10 mol, 65.1% yield, 93.4% purity) as a yellow solid. $^1$H NMR (400 MHz, CHLOROFORM-d) δ=10.31 (s, 1H), 8.02 (d, J=7.6 Hz, 1H), 7.02 (dd, J=8.0, 8.8 Hz, 1H), 6.82 (dd, J=4.8, 8.8 Hz, 1H), 6.14 (d, J=7.6 Hz, 1H), 5.29 (s, 2H), 5.17 (br s, 2H), 3.54 (q, J=7.2 Hz, 2H), 1.60 (s, 9H), 1.26 (t, J=7.2 Hz, 3H).

Step 2. To a solution of 11-1 (8.00 g, 16.7 mmol, 1.00 eq.) in dimethyl formamide (25.0 mL) was added cuprous cyanide (2.24 g, 24.9 mmol, 5.46 mL, 1.50 eq.). The mixture was stirred at 130° C. for 10 hours. The reaction mixture was added ammonium hydroxide (10.0 mL) and diluted with water (300 mL). Then the mixture was extracted with ethyl acetate (300 mL×3). The combined organic layers were washed with saturated ammonium chloride (100 mL×5), dried over saturated sodium sulfate, filtered and concentrated under reduced pressure to give a residue, The residue was purified by prep-HPLC (column: Phenomenex Gemini C18 250*50 mm*10 um; mobile phase: [water (0.05% ammonia hydroxide v/v)-ACN]; B %: 40%-60%, 45MIN; 70% min) to give 11-2 (2.00 g, 4.54 mmol, 27.2% yield, 96.7% purity) as a brown solid. $^1$H NMR (400 MHz, DMSO-d$_6$) δ=10.66 (br s, 1H), 8.38 (d, J=7.6 Hz, 1H), 7.31 (t, J=9.2 Hz, 1H), 7.16 (dd, J=4.8, 8.8 Hz, 1H), 6.52 (d, J=7.6 Hz, 1H), 5.96 (s, 2H), 4.94 (br s, 2H), 3.50 (br d, J=6.8 Hz, 2H), 1.46 (s, 9H), 1.10 (t, J=6.8 Hz, 3H).

Step 3. To a solution of 11-2 (2.05 g, 4.81 mmol, 1.00 eq.) in dimethyl formamide (20.0 mL) was added potassium carbonate (1.66 g, 12.0 mmol, 2.50 eq.) and 11-2A (1.71 g, 7.21 mmol, 1.50 eq.). The mixture was stirred at 30° C. for 6 hours. The reaction mixture was diluted with water (100 mL) and extracted with ethyl acetate (100 mL×3). The combined organic layers were washed with brine (100 mL×3), dried over anhydrous sodium sulfate, filtered and concentrated under reduced pressure to give a residue, The residue was purified by prep-HPLC (column: Phenomenex Gemini C18 250*50 mm*10 um; mobile phase: [water (0.05% ammonia hydroxide v/v)-ACN]; B %: 50%-80%, 25MIN80% min) to give 11-3 (1.80 g, 3.05 mmol, 63.4% yield, 98.9% purity) as a light yellow solid. $^1$H NMR (400 MHz, DMSO-d$_6$) δ=8.36 (d, J=8.0 Hz, 1H), 7.52-7.40 (m, 2H), 6.96 (br s, 1H), 6.52 (br d, J=7.6 Hz, 1H), 5.93 (s, 2H), 5.12-4.91 (m, 2H), 4.58-4.44 (m, 1H), 3.44 (br s, 2H), 3.21-3.09 (m, 1H), 3.08-2.95 (m, 1H), 1.44 (s, 9H), 1.34 (s, 9H), 1.11 (d, J=6.4 Hz, 3H), 1.07 (t, J=6.8 Hz, 3H).

Step 4. 11-3 was converted to 11 following step 5 in General Method L.

| Cpd | Structure | MS m/z | $^1$H NMR (300 MHz, DMSO-d$_6$) δ ppm |
|---|---|---|---|
| 1 | 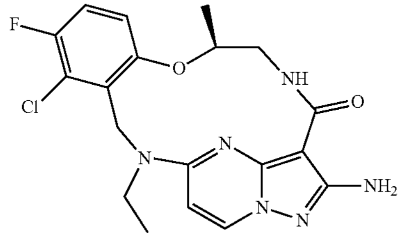 [SMILES: CCN1Cc2c(ccc(F)c2Cl)O[C@@H](C)CNC(=O)c2c(N)nn3ccc1nc23] | 419.1 419.1 | 8.84 (t, J = 4.68 Hz, 1 H) 8.35 (d, J = 7.70 Hz, 1 H) 7.18-7.30 (m, 1 H) 7.07-7.18 (m, 1 H) 6.48 (d, J = 7.89 Hz, 1 H) 5.81 (s, 2 H) 5.55 (dd, J = 15.04, 1.83 Hz, 1 H) 4.80-4.92 (m, 1 H) 3.97-4.13 (m, 2 H) 3.67-3.83 (m, 2 H) 3.22-3.29 (m, 1 H) 1.44 (d, J = 6.05 Hz, 3 H) 1.18 (t, J = 6.97 Hz, 3 H) |

| Cpd | Structure | MS m/z | ¹H NMR (300 MHz, DMSO-d₆) δ ppm |
|---|---|---|---|
| 2 | 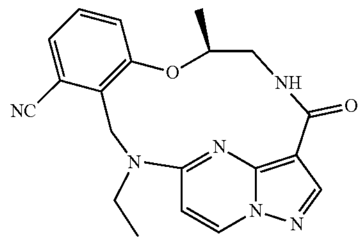 [SMILES: CCN1Cc2c(C#N)cccc2O[C@@H](C)CNC(=O)c2cnn3ccc1nc23] | 377.2 | 9.05-8.95 (m, 1H), 8.78 (d, J = 7.9 Hz, 1H), 8.09 (s, 1H), 7.49 (dd, J = 2.6, 7.0 Hz, 1H), 7.40-7.29 (m, 2H), 6.95 (d, J = 8.0 Hz, 1H), 5.51 (d, J = 15.1 Hz, 1H), 5.02-4.86 (m, 1H), 4.39-4.13 (m, 2H), 3.90-3.74 (m, 2H), 3.32-3.21 (m, 1H), 1.48 (d, J 3H), 1.23-1.17 (m, 3H) |
| 3 | 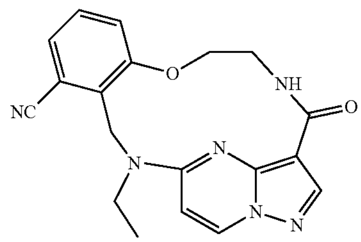 [SMILES: CCN1Cc2c(C#N)cccc2OCCNC(=O)c2cnn3ccc1nc23] | 363.2 | 8.88 (dd, J = 3.3, 5.8 Hz, 1H), 8.78 (d, J 1H), 8.09 (s, 1H), 7.51 (dd, J = 3.0, 6.6 Hz, 1H), 7.41-7.33 (m, 2H), 6.95 (d, J = 8.0 Hz, 1H), 5.54 (d, J = 15.1 Hz, 1H), 4.72-4.59 (m, 1H), 4.51 (ddd, J = 5.3, 9.2, 11.6 Hz, 1H), 4.35-4.13 (m, 2H), 3.83 (dd, J = 7.2, 15.3 Hz, 1H), 3.73-3.49 (m, 2H), 1.20 (t, J = 7.0 Hz, 3H) |
| 4 | 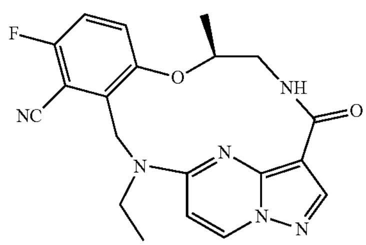 [SMILES: CCN1Cc2c(ccc(F)c2C#N)O[C@@H](C)CNC(=O)c2cnn3ccc1nc23] | 395.2 | 8.93 (t, J = 4.9 Hz, 1H), 8.80 (d, J = 7.9 Hz, 1H), 8.10 (s, 1H), 7.55 (dd, J = 4.7, 9.4 Hz, 1H), 7.32 (t, J = 8.9 Hz, 1H), 6.96 (d, J = 8.0 Hz, 1H), 5.55-5.43 (m, 1H), 4.99-4.85 (m, 1H), 4.34 (d, J = 15.3 Hz, 1H), 4.28-4.15 (m, 1H), 3.38-3.28 (m, 1H), 1.47 (d, J = 6.1 Hz, 3H), 1.20 (t, J = 7.0 Hz, 3H) |
| 5 | 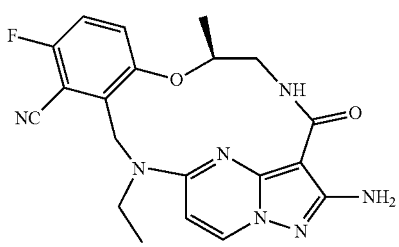 [SMILES: CCN1Cc2c(ccc(F)c2C#N)O[C@@H](C)CNC(=O)c2c(N)nn3ccc1nc23] | 410.2 | 8.69 (t, J = 5.00 Hz, 1 H) 8.41 (d, J = 7.61 Hz, 1 H) 7.53 (dd, J = 9.49, 4.72 Hz, 1 H) 7.26 - 7.37 (m, 1 H) 6.60 (d, J = 7.79 Hz, 1H) 5.86-6.14 (m, 2 H) 5.45 (br d, J = 15.41 Hz, 1 H) 4.85-4.97 (m, 1 H) 4.26 (d, J = 15.50 Hz, 1 H) 4.02-4.17 (m, 1 H) 3.64-3.80 (m, 2 H) 3.23-3.35 (m, 1 H) 1.46 (d, J = 6.24 Hz, 3 H) 1.17 (t, J = 6.92 Hz, 3 H) |
| 6 | 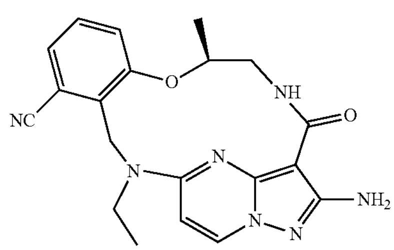 [SMILES: CCN1Cc2c(C#N)cccc2O[C@@H](C)CNC(=O)c2c(N)nn3ccc1nc23] | 392.2 | 8.76 (t, J = 4.86 Hz, 1 H) 8.39 (d, J = 7.61 Hz, 1 H) 7.48 (dd, J = 6.97, 2.75 Hz, 1 H) 7.29-7.37 (m, 2 H) 6.58 (d, J = 7.79 Hz, 1 H) 5.48 (d, J = 15.04 Hz, 1 H) 4.86-5.00 (m, 1 H) 4.21 (d, J = 15.13 Hz, 1 H) 4.03-4.17 (m, 1 H) 3.68-3.83 (m, 2 H) 3.29 (dt, J = 13.04, 5.03 Hz, 1 H) 1.47 (d, J = 6.14 Hz, 3 H) 1.17 (t, J = 6.97 Hz, 3 H) |
| 7 | 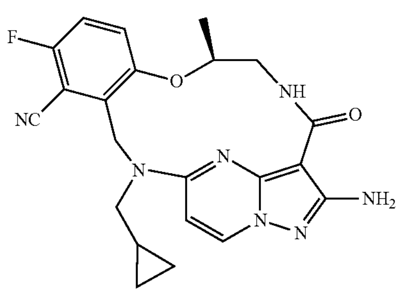 [SMILES: C[C@H]1CNC(=O)c2c(N)nn3ccc(nc23)N(CC2CC2)Cc2c(ccc(F)c2C#N)O1] | 436.2 | 8.73 (t, J = 5.09 Hz, 1 H) 8.39 (d, J = 7.70 Hz, 1 H) 7.53 (dd, J = 9.49, 4.81 Hz, 1 H) 7.31 (t, J = 8.89 Hz, 1 H) 6.71 (d, J = 7.70 Hz, 1 H) 5.45-5.57 (m, 1 H) 4.83-4.94 (m, 1 H) 4.38 (br d, J = 15.13 Hz, 2 H) 4.22 (br dd, J = 15.36, 5.64 Hz, 3 H) 3.73 (dt, J = 13.53, 4.93 Hz, 1 H) 3.23-3.37 (m, 2 H) 1.47 (d, J = 6.14 Hz, 3 H) 1.02-1.17 (m, 1 H) 0.43-0.57 (m, 3 H) 0.21-0.31 (m, 1 H) |

| Cpd | Structure | MS m/z | ¹H NMR (300 MHz, DMSO-d₆) δ ppm |
|---|---|---|---|
| 8 | 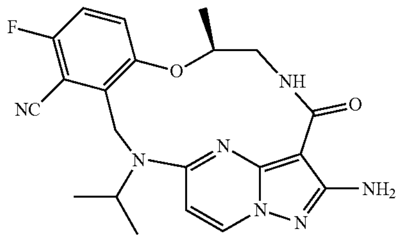 [SMILES: CC(C)N1Cc2c(ccc(F)c2C#N)O[C@@H](C)CNC(=O)c2c(N)nn3ccc1nc23] | 424.2 | 8.39-8.51 (m, 2 H) 7.55 (dd, J = 9.54, 4.68 Hz, 1 H) 7.28 (t, J = 8.80 Hz, 1 H) 6.73 (d, J = 7.70 Hz, 1 H) 5.17 (br d, J = 15.77 Hz, 1 H) 4.95-5.04 (m, 2 H) 4.48 (dt, J = 13.02, 6.33 Hz, 2 H) 4.33 (br d, J = 15.68 Hz, 1 H) 3.59-3.71 (m, 1 H) 3.30 (ddd, J = 13.89, 6.05, 3.07 Hz, 1 H) 1.58 (d, J = 6.51 Hz, 3 H) 1.48 (d, J = 6.24 Hz, 3 H) 1.16 (d, J = 6.33 Hz, 3 H) |
| 9 | 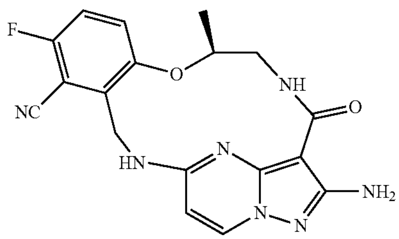 [SMILES: C[C@H]1CNC(=O)c2c(N)nn3ccc(nc23)NCc2c(ccc(F)c2C#N)O1] | 382.2 | 9.32-9.43 (m, 1 H) 8.65 (br t, J = 5.41 Hz, 1 H) 8.25 (d, J = 7.43 Hz, 1 H) 7.48 (dd, J = 9.49, 4.81 Hz, 1 H) 7.28-7.40 (m, 1 H) 6.29 (d, J = 7.34 Hz, 1 H) 5.15 (br dd, J = 14.86, 2.66 Hz, 1 H) 4.66-4.79 (m, 1 H) 4.10-4.22 (m, 1 H) 3.77-3.87 (m, 1 H) 3.15-3.25 (m, 1 H) 1.44 (d, J = 6.05 Hz, 3 H) |
| 10 | 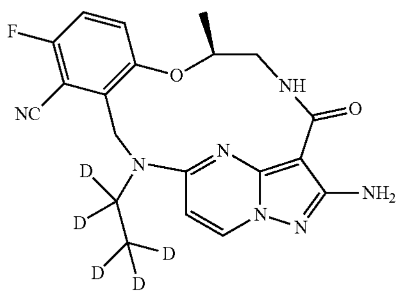 [SMILES: [2H]C([2H])([2H])C([2H])([2H])N1Cc2c(ccc(F)c2C#N)O[C@@H](C)CNC(=O)c2c(N)nn3ccc1nc23] | 415.3 | 8.69 (t, J = 4.72 Hz, 1 H) 8.41 (d, J = 7.70 Hz, 1 H) 7.54 (dd, J = 9.49, 4.81 Hz, 1 H) 7.23-7.39 (m, 1 H) 6.60 (d, J = 7.70 Hz, 1 H) 5.85 (s, 2 H) 5.44 (dd, J = 15.13, 1.38 Hz, 1 H) 4.82-5.00 (m, 1 H) 4.26 (d, J = 15.22 Hz, 1 H) 3.70 (dt, J = 13.64, 4.37 Hz, 1 H) 3.22-3.32 (m, 1 H) 1.46 (d, J = 6.24 Hz, 3 H) |
| 11 | 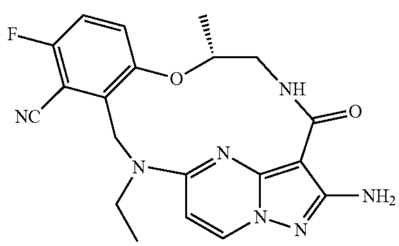 [SMILES: CCN1Cc2c(ccc(F)c2C#N)O[C@H](C)CNC(=O)c2c(N)nn3ccc1nc23] | 410.1 | 8.69 (br t, J = 4.72 Hz, 1 H) 8.41 (d, J = 7.61 Hz, 1 H) 7.53 (dd, J = 9.40, 4.72 Hz, 1 H) 7.31 (t, J = 8.89 Hz, 1 H) 6.60 (d, J = 7.70 Hz, 1 H) 5.85 (s, 2 H) 5.44 (br d, J = 15.31 Hz, 1 H) 4.83-5.00 (m, 1 H) 4.26 (br d, J = 15.31 Hz, 1 H) 4.00-4.18 (m, 1 H) 3.61-3.81 (m, 2 H) 3.23-3.31 (m, 1 H) 1.46 (d, J = 6.24 Hz, 3 H) 1.17 (t, J = 6.88 Hz, 3 H) |
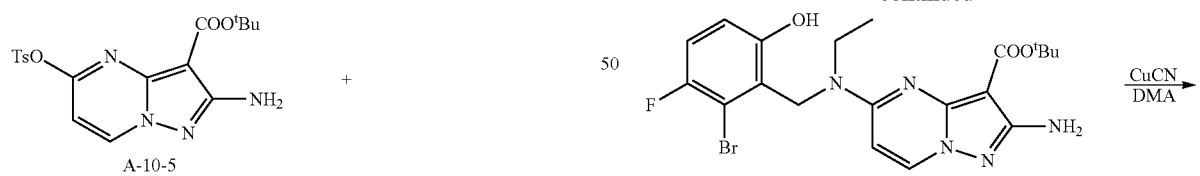
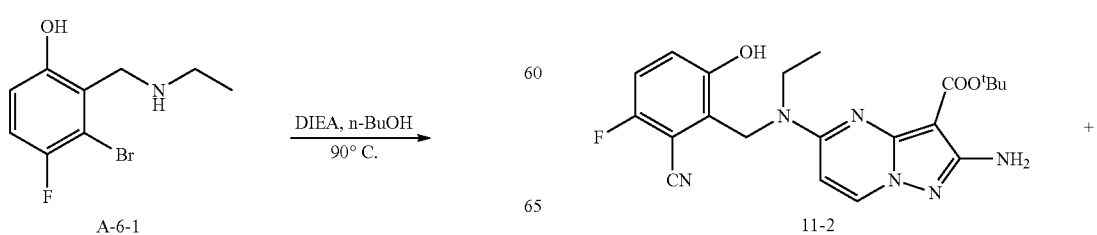

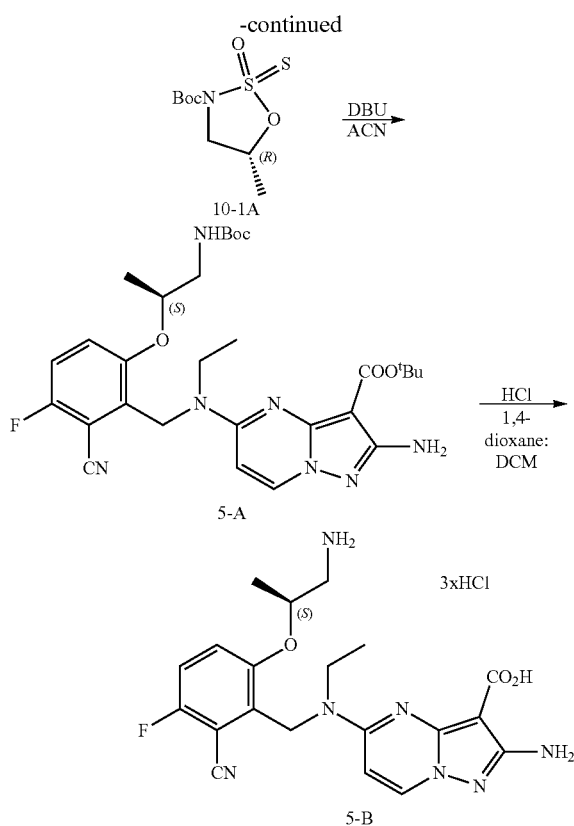

Charged the reactor with A-10-5 (1.0 eq), A-6-1 (1.1 eq), DIPEA (3.0 eq) and n-butanol (10 vol). The resulting mixture was heated at 90-95° C. for 10 h. The reaction progress was monitored by HPLC, 2% of A-10-5 revealed that the reaction is complete. After a passing IPC test the reaction mixture was cooled to 0-5° C. The reaction mixture was stirred for 2 hours. The solids were filtered and washed with cold MTBE (2×0.5 volume). The solids were dried under vacuum oven at 40-50° C. to constant weight with yield 2950 g (75%) and 99.9% HPLC purity.

Charged the reactor with 11-1 (1.0 eq), DMA (5 vol) and CuCN (2.5 eq). The resulting mixture was heated at 90-100° C. for 92 hours. The reaction progress was monitored by HPLC, NMT 2% of 11-1 revealed that the reaction is complete. After a passing IPC test. Transferred the reaction mixture into $2^{nd}$ reactor containing DCM (46 L, 15 vol), Celite (3073 g) at 35-40° C. The reaction mixture was stirred for 30 min at 20-30° C. Filtered the reaction mixture through one inch celite bed and washed with DCM (2×5 vol). Filtrate was charged with Celite (3073 g), charcoal (1000 g) and Buffer ($H_2O/NH_4Cl/NH_4OH$, 9.4/4.0/3.8; 31 L, 10 v) to filtrate. The reaction mixture was stirred for 2 hours at 20-30° C. Filtered the reaction mixture through one inch celite bed and washed with DCM (2×5 vol). Separated the layers and the organic layer was washed with Buffer (2×31 L, 2×10 v) and water (2×10 vol). Concentrated the organic to minimum volume and co-evaporated with MTBE (2×5 vol). The reaction mixture was cooled to 15-30° C. and stirred for 4 hours. The solids were filtered and washed with cold Methanol (2×1 volume). The solids were dried under vacuum oven at 40-50° C. to constant weight with yield 2310 g (82%) and 99% HPLC purity.

Charged the reactor with 11-2 (1.0 eq), 10-1A (1.15 eq), acetonitrile (5 vol) and DBU (2.5 eq). The resulting mixture was stirred at 20-30° C. for 2 hours. The reaction progress was monitored by HPLC, 1% of 11-2 revealed that the reaction is complete. After a passing IPC test. The reactor was charged ethyl acetate (10 vol) and 25 wt % citric acid solution (10 vol). The reaction mixture was stirred overnight and separated the layers and back extracted the aqueous layer with Ethyl acetate (10 volumes). Combined organic layer was concentrated to minimum volume and co-evaporated with DCM (2×5 vol). Concentrated to dryness obtained 1630 g (92%) and 99% HPLC purity.

Charged the reactor with 5-A (1.0 eq), DCM (10 vol) and 4M HCl in Dioxane (10 eq). The resulting mixture was stirred at 20-30° C. for 2 hours. The reaction progress was monitored by HPLC, 1% of 5-A revealed that the reaction is complete. After a passing IPC test. The solids were filtered, washed with MTBE (2×5 vol) and dried the solids in filter with vacuum under nitrogen to obtained yield with 1450 g (Assume 100% 1300 g) and 97% purity.

Charged the reactor with 5-B (1.0 eq), DIPEA (5.0 eq) and DCM (20 vol) and DMF (1 vol). The resulting mixture was stirred at room temperature for (15-30° C.) for 15-30 min. Charged reactor with FDPP (1.3 eq) in one portion. The resulting mixture was stirred at room temperature for (15-30° C.) overnight. The reaction progress was monitored by HPLC, 1% of 5-B revealed that the reaction is complete. After a passing IPC test. The reactor was charged 1M $Na_2CO_3$ solution (10 volumes). The reaction mixture was stirred for 30 min. and separated the layers. The organic layer was washed with 1M $Na_2CO_3$ solution (10 volumes) and water (2×10 vol) and brine (50 volumes). The organic layer was concentrated the organic to minimum volume and co-evaporated with methanol (2×5 vol). Organic layer was dried with $MgSO_4$ and charcoal and Filtered the organic layer though GF paper and concentrated the organic to minimum volume and co-evaporated with ethanol (2×5 vol). Concentrated to dryness and added EtOH (2 L) and stir at room temperature for 1 hour. The solids were filtered and washed with cold Methanol (2×1 volume). The solids were dried under vacuum oven at 40-50° C. to constant weight with yield 850 g (86%).

Charged the reactor with crude 5 (1.0 eq) and water (12 vol). The resulting mixture was stirred at room temperature for 3 days. The solids were filtered and washed with water (2×1 volume). The solids were dried under vacuum oven at 40-50° C. to constant weight with yield 723 g (86%) and 98.7% HPLC purity.

Biologic Assays

In-Vitro Assays
Materials and Methods
Biochemical Kinase Assay Method

The biochemical kinase assay was performed at Reaction Biology Corporation (www.reactionbiology.com, Malvern, Pa.) following the procedures described in the reference (Anastassiadis T, et al *Nat Biotechnol.* 2011, 29, 1039). Specific kinase/substrate pairs along with required cofactors were prepared in reaction buffer 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2). Compounds were delivered into the reaction, followed ~20 minutes later by addition of a mixture of ATP (Sigma, St. Louis Mo.) and $^{33}P$ ATP (Perkin Elmer, Waltham Mass.) to a final concentration of 10 μM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. $IC_{50}$ values and curve fits were obtained using Prism (GraphPad Software).

Cell Lines and Cell Culture:

Human gastric cancer cell line SNU-5, lung cancer cell lines HCC827, H1975, mouse myelogenous leukemia cell line M-NFS-60 were obtained from ATCC. Cell lines Ba/F3, MKN-45 were purchased from DSMZ. SNU-216 cell line was purchased from KCLB.

Cloning and Ba/F3 Stable Cell Line Creation

The TEL-CSF-1R cDNA was synthesized at GenScript and cloned into pCDH-CMV-MCS-EF1-Puro plasmid (System Biosciences, Inc). Ba/F3 TEL-CSF1R was generated by transducing Ba/F3 cells with lentivirus containing TEL-CSF1R cDNA clone. Stable cell lines were selected by puromycin treatment, followed by IL-3 withdrawal. Briefly, $1 \times 10^6$ Ba/F3 cells were transduced with lentivirus supernatant in the presence of 8 μg/mL protamine sulfate. The transduced cells were subsequently selected with 1 μg/mL puromycin in the presence of IL3-containing medium RPMI1640, plus 10% FBS. After 10-12 days of selection, the surviving cells were further selected for IL3 independent growth.

Cell Proliferation Assays:

Two thousand cells per well were seeded in 384 well white plate for 24 hrs, and then treated with compounds for 72 hours (37° C., 5% $CO_2$). Cell proliferation was measured using CellTiter-Glo luciferase-based ATP detection assay (Promega) following the manufacturer's protocol. $IC_{50}$ determinations were performed using GraphPad Prism software (GraphPad, Inc., San Diego, Calif.).

Immunoblotting for Cellular Kinase Phosphorylation Assays

Gastric carcinoma cell lines MKN-45, SNU-5 (both with MET overexpression), HCC827 cells (harboring endogenous EGFR mutation delE1746_A750), NCI-H1975 cells (harboring endogenous EGFR double mutations L858R/T790M) or SNU216 cells were cultured in RPMI 1640 medium, supplemented with 10% fetal bovine serum and 100 U/mL of penicillin/streptomycin. Half a million cells per well were seeded in 24 well plate for 24 hrs, and then treated with compounds for 4 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 μg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting phosphorylated MET (Y1234/Y1235) (Cell Signaling Technology), MET (Y1349), MET (Y1003), total MET (Cell Signaling Technology), phosphorylated EGFR (Y1068) and total EGFR (Cell Signaling Technology), phosphorylated STAT3 and STAT5, total STAT3 and STAT5 (Cell Signaling Technology), phosphorylated AKT (Cell Signaling Technology), total AKT (Cell Signaling Technology), phosphorylated ERK (Cell Signaling Technology), total ERK (Cell Signaling Technology), phosphorylated PLCγ2 and total PLCγ2 (Cell Signaling Technology), phosphorylated SRC Y416 (Cell Signaling Technology), total SRC (Cell Signaling Technology), phosphorylated paxillin Y118 (Cell Signaling Technology), total paxillin (Cell Signaling Technology), PARP, actin (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). The relative density of the chemiluminescent bands were quantified via Image Studio Digits from LICOR. The half inhibitory concentration ($IC_{50}$) value is calculated using non-linear regression analysis through GraphPad Prism software (GraphPad, Inc., San Diego, Calif.).

The Scratch Wound Healing Assays

MKN-45 or HCC827 cells were seeded in 24-well plate. After 12-24 hours, confluent cell monolayers were gently scraped with a sterile pipette tip to form a scratch. The plates were washed with fresh medium, and the cells were incubated with medium alone or medium containing various concentration of compounds. After 36-48 hours, the plates were examined and recorded by an EVOS FL microscopy (Life Technology) to monitor resealing of the cell monolayer.

In-Vivo Methods

Cell Lines

MKN-45 and Ba/F3 ETV6-CSF1R cells were cultured using standard techniques in RPMI-1640 medium (Corning, Inc) with 10% fetal bovine serum (Thermo Fisher Scientific, Inc) at 37° C. in a humidified atmosphere with 5% $CO_2$. For implantation, cells were harvested and pelleted by centrifugation at 250 g for 2 minutes. Cells were washed once and resuspended in serum-free medium supplemented with 50% matrigel (v/v).

Subcutaneous Xenograft Models in Immune Compromised Mice

Female athymic nude mice (5-8 weeks of age) were obtained from Charles River Laboratory and were housed in Innovive IVC disposable cages on HEPA filtered ventilated racks with ad libitum access to rodent chow and water. Five million cells in 100 μL serum-free medium supplemented with 50% matrigel (Corning, Inc) were implanted subcutaneously in the right flank region of the mouse. Tumor size and body weight were measured on designated days. Tumor size was measured with an electronic caliper and tumor volume was calculated as the product of length*width$^2$*0.5. Mice were randomized by tumor size into treatment groups when tumor volume reached about 200 mm$^3$ and Compound 5 was administered orally (BID) at determined doses.

Tumor Processing and Immunoblotting for In Vivo Pharmacodynamic Studies

Mice bearing xenograft tumors were humanely euthanized and tumors were resected and snap frozen in liquid nitrogen and stored at −80° C. Frozen tumor samples were processed at 4° C. in 1× Cell Lysis Buffer (Cell Signaling Technologies) to extract proteins. SDS loading samples were prepared by adding one volume of 4×LDS Sample Buffer (Life Technologies, Inc) to three volumes of protein lysate. Tumor SDS protein samples were processed by SDS-PAGE and immunoblotted with rabbit anti-phosphorylated MET, mouse anti-MET and mouse anti-actin antibodies (Cell Signaling Technologies). The signals from immunoblot were detected by C-DiGit Blot Scanner from LI-COR and the signal intensity were quantified using the Image Studio Digit software (LI-COR).

Subcutaneous Patient-Derived Xenograft Model in Immune Compromised Mice

Female BALB/c nude mice (6-7 weeks) were obtained from Beijing Anikeeper Biotech Co. Ltd (Beijing, China). Primary human tumor xenograft model LU2503 tumors were grown in stock mice. Tumor fragments (2-3 mm in diameter) were harvested from stock mice and inoculated into the right front back of each mouse for tumor development. 16 mice were enrolled in the study. All animals were randomly allocated to the 2 different study groups. Tumor size and body weight were measured on designated days. Tumor size was measured using a caliper and tumor volume was calculated as the product of length*width$^2$*0.5. Mice were randomized by tumor size into treatment groups when tumor volume reached about 200 mm$^3$ and Compound 5 was administered orally (BID) at 15 mg/kg.

Subcutaneous MC38 Syngeneic Model in C57BL/6 J Mice

C57BL/6 J female mice (6 weeks) were purchased from the Jackson Laboratory, and maintained in accordance with the guidelines for the care and use of laboratory animals. Half million MC38 cancer cells in 100 μL serum-free medium were implanted subcutaneously in the right flank region of the mouse. Tumor size and body weight were measured on designated days. Tumor size was measured with an electronic caliper and tumor volume was calculated as the product of length*width$^2$*0.5. Mice were randomized by tumor size into treatment groups when tumor volume reached about 70-90 mm$^3$. Vehicle control, Compound 5, PD-1 antibody or Compound 5 plus PD-1 antibody were administered orally (BID) at determined doses.

MC38 Syngeneic Model PD Biomarker Studies

MC38 tumors were collected on day 7 and day 11. The collected tumors were dissociated using MiltenyiGentleMax. FACS analysis of tumors were performed for the tumor associated immune cells including tumor associated macrophages (TAM) and TAM subtypes (M1 and M2), myeloid derived suppression cells (MDSC), cytotoxic T lymphocytes (CTL, i.e. CD8+ T cells), CD4+ T cells, and regulatory T cells (Treg).

Data and Results:
Enzymatic Kinase Activities

The enzymatic kinase inhibition activities at 10 μM ATP concentration were determined at Reaction Biology. The results of IC$_{50}$ were summarized in Table 1.

TABLE 1

| Compd # | Enzymatic Kinase SRC IC$_{50}$ (nM) | Enzymatic Kinase MET IC$_{50}$ (nM) | Enzymatic Kinase c-FMS (CSF1R) IC$_{50}$ (nM) |
| --- | --- | --- | --- |
| 1 | ND* | 20.4 | ND |
| 2 | 3.00 | 36.5 | ND |
| 3 | 97.1 | 110.0 | ND |
| 4 | 0.49 | 1.85 | 0.42 |
| 5 | 0.12 | 0.14 | 0.76 |
| 6 | 13.6 | 9.7 | ND |
| 7 | 0.70 | 2.2 | ND |
| 8 | 0.83 | 3.8 | ND |

*ND = not determined

Anti-Cell Proliferation Activities

The anti-cell proliferation activities against MET and CSF1R driven cell lines were conducted with MKN-45, SNU-5, Ba/F3 TEL-CSF1R cells, and M-NFS-60 respectively. The results of IC$_{50}$ were summarized in Table 2 and Table 3.

TABLE 2

| Compd # | MET Cell Proliferation MKN-45 IC$_{50}$ (nM) | MET Cell Proliferation SNU-5 IC$_{50}$ (nM) | CSF1R Cell Proliferation Ba/F3 TEL-CSF1R IC$_{50}$ (nM) |
| --- | --- | --- | --- |
| 1 | 193 | 173.9 | 180.3 |
| 2 | 129 | 135.9 | 281.4 |
| 3 | 471 | 674.1 | 1740 |
| 4 | 12 | 5.8 | 98.1 |
| 5 | 0.2 | 0.17 | 19.3 |
| 6 | 58.3 | 36.8 | 187.7 |
| 7 | 17.7 | 1.0 | 108.1 |
| 8 | 1.0 | 1.0 | 39.0 |
| 9 | 297 | | |
| 10 | 0.2 | | |
| 11 | 251 | | |

TABLE 3

| M-NFS-60 (IC$_{50}$s nM) | CSF-1 (ng/mL) | | | | | | |
| --- | --- | --- | --- | --- | --- | --- | --- |
| | 0 | 0.3 | 1 | 3 | 10 | 30 | 100 |
| Pexidartinib (PLX-3397) | <0.1 | 2 | 146.4 | 212.5 | 379.7 | 594.7 | 702.3 |
| Compound 5 | 0.3 | 3 | 11.6 | 78.2 | 84.1 | 180.8 | 174.5 |

Compound 5 Inhibited the Phosphorylation of MET and Downstream Signaling

Figure 1:
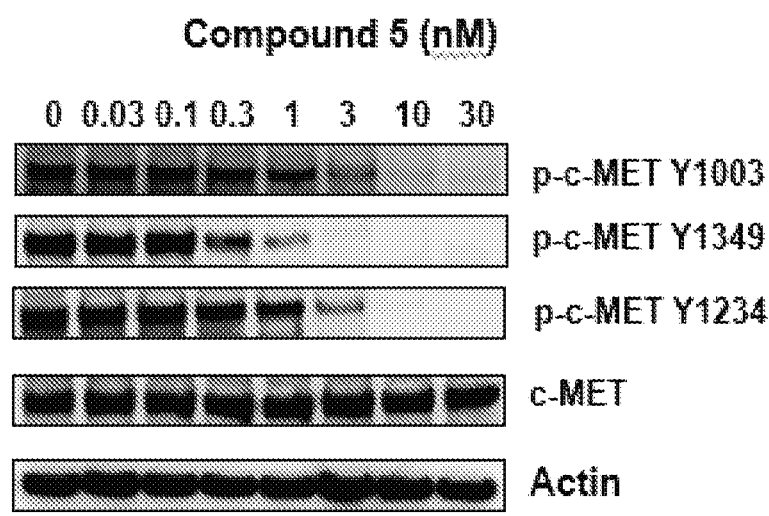
FIG. 1 shows a gel image of studies of MET phosphorylation in SNU-5 cells after 4 hour incubation with Compound 5. The gel shows that Compound 5 inhibited MET phosphorylation in SNU-5 cells.
Figure 2:
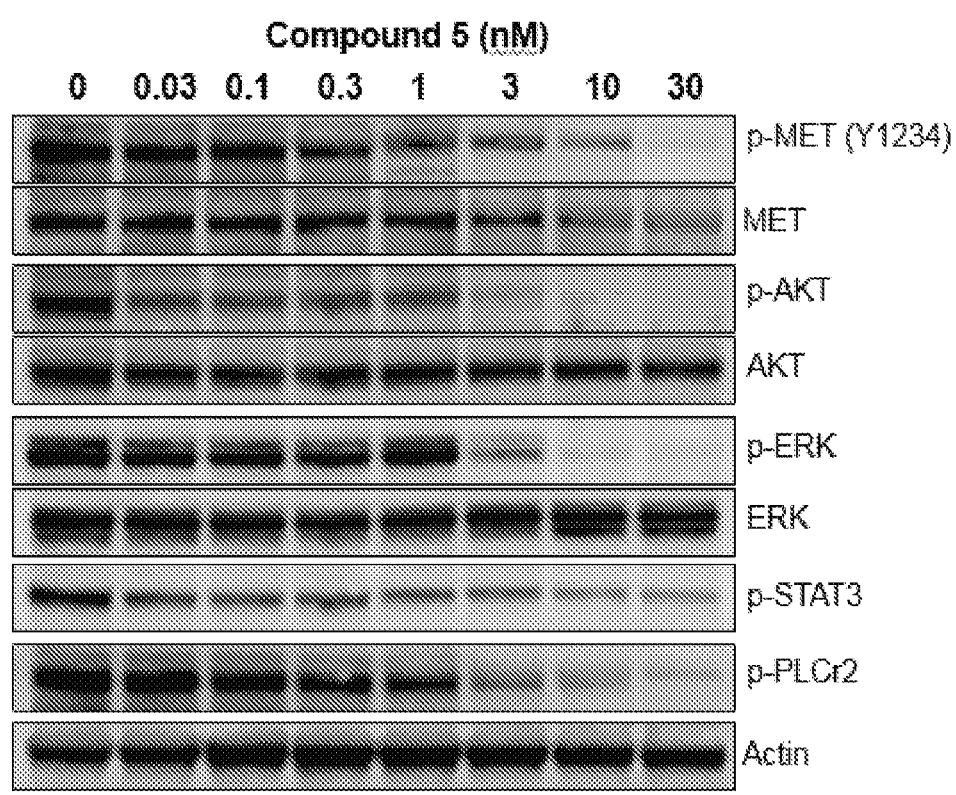
FIG. 2 shows a gel image of studies of phosphorylation of MET and downstream effectors in MKN-45 cells after 16 hour incubation with Compound 5. The gel shows that Compound 5 inhibited MET phosphorylation and downstream effectors in MKN-45 cells.

The pharmacodynamic inhibiting activity of Compound 5 on MET and the corresponding downstream signaling in MET-driven cells was evaluated, and the results were shown in FIGS. 1 and 2. Compound 5 caused the suppression of MET autophosphorylation as well as the downstream STAT3, ERK and AKT phosphorylation at IC$_{50}$s of around 1-3 nM in SNU-5 and MKN-45 cell lines (FIGS. 1 & 2).

Compound 5 Synergized with AZD9291 in HCC827 Cells

Figure 3:
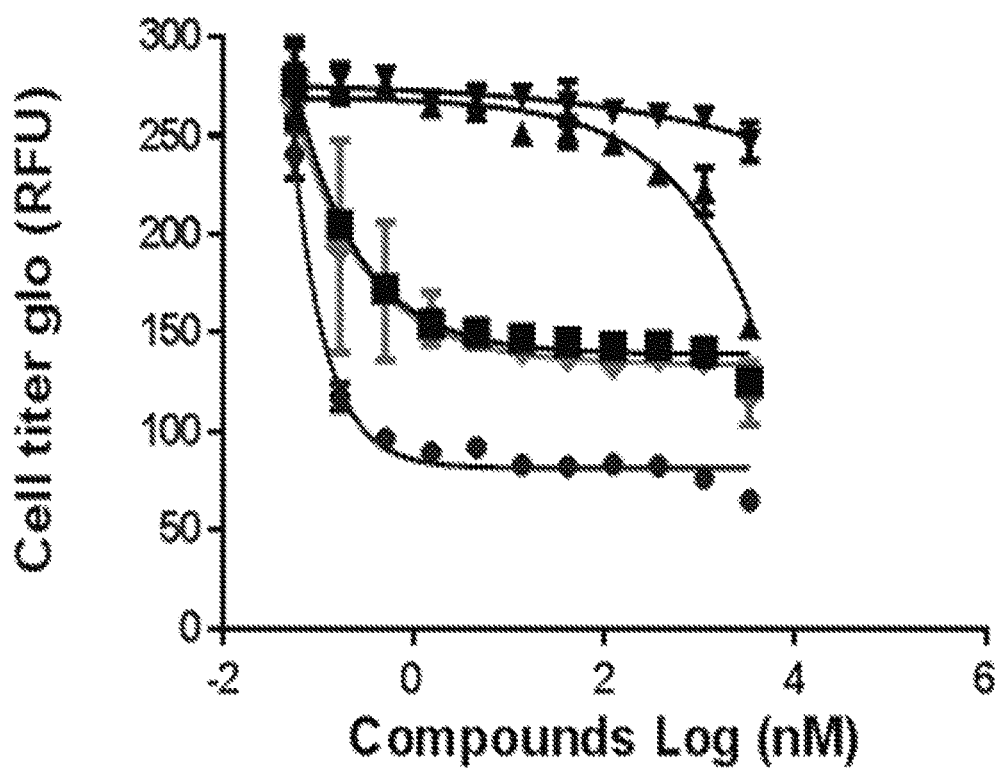
FIG. 3 is a graph showing the effects of Compound 5, capmatinib, and AZD9291 on HCC827 cell proliferation. A strong synergistic activity was observed in the combination of AZD9291 with Compound 5 with an $IC_{50}$ of 2 nM and Emax 71% in HCC827 cell proliferation assay. (▼) capmatinib ($IC_{50}$: >10000 nM, Emax %: –), (▲) Compound 5 ($IC_{50}$: 3000 nM, Emax %: –), (■) AZD9291 ($IC_{50}$: 5 nM (partial), Emax %: 47), (♦) capmatinib (1 μM)+AZD9291

The lung cancer cell line HCC827 has endogenous EGFR exon 19 deletion with MET overexpression. The EGFR inhibitor AZD9291 showed an IC$_{50}$ of 5 nM, however, with a maximum inhibition of Emax 47% in cell proliferation assay. The selective MET inhibitor capmatinib is not active in HCC827 cell proliferation assay. The combination of AZD9291 with capmatinib showed a similar effect as AZD9291 alone with an IC$_{50}$ of 5 nM and Emax 48%. The MET/SRC dual inhibitor Compound 5 showed an IC$_{50}$ of 3000 nM in HCC827 cell proliferation assay. A strong synergistic activity was observed in the combination of AZD9291 with Compound 5 with an IC$_{50}$ of 2 nM and Emax 71% in HCC827 cell proliferation assay. The results were summarized in FIG. 3. Compound 5 synergized with AZD9291 for apoptosis in HCC827 cell line as shown in FIG. 4.

Evaluation of the Migration Inhibition of Compound 5

Compound 5 inhibited the migration of MKN-45 or HCC827 cells after 36-48 hours treatment in the wound healing assays, whereas, the selective MET inhibitor capmatinib only inhibited the migration of MKN-45 cells and has minimum effect on HCC827 cells. The results were presented in FIGS. 5 & 6.

In-Vivo Studies

Antitumor Efficacy of Compound 5 in Xenograft Tumor Models

The antitumor efficacy of Compound 5 was evaluated in several tumor xenograft models representing cancer populations in which dysregulation of MET is implicated.

MKN-45 Gastric Adenocarcinoma Model

The Met gene amplification in MKN-45 cells underlies the molecular mechanism for tumor growth. Athymic nude mice bearing MKN-45 tumors (at the average tumor size of 210 mm$^3$) were dosed with Compound 5 orally BID for twelve days (FIG. 7). The control group of mice were given vehicle only. Tumor volume (TMV) was measured by caliper on the indicated days and is shown at mean±sem in FIG. 7. The mean TMVs are significantly lower in the treated groups compared to that of the control group (p<0.05) as determined by two-way repeated ANOVA followed by post hoc analysis. Tumor growth inhibition (TGI) was calculated as $100\%*\{1-[(TMV_{Treated\ Last\ Day\ of\ Treatment} - TMV_{Treated\ First\ Day\ of\ Treatment})/(TMV_{Control\ on\ Last\ Day\ of\ Treatment} - TMV_{Control\ on\ First\ Day\ of\ Treatment})]\}$ when $TMV_{Treated\ Last\ Day\ of\ Treatment} \geq TMV_{Treated\ First\ Day\ of\ Treatment}$. In the case of $TMV_{Treated\ Last\ Day\ of\ Treatment} < TMV_{Treated\ First\ Day\ of\ Treatment}$, tumor regression (REG) was calculated as $100\%*(1-TMV_{Treated\ Last\ Day\ of\ Treatment}/TMV_{Treated\ First\ Day\ of\ Treatment})$. In this study, Compound 5 demonstrated the ability to inhibit tumor growth at 47% at the dose of 3 mg/kg, BID. When dosed at 10 mg/kg, BID and 30 mg/kg, BID, treatment of Compound 5 resulted in 6% and 44% tumor regression, respectively. Tumor size was reduced in 5 out 10 mice treated with Compound 5 at 10 mg/kg, BID and in 9 out of 10 mice treated with Compound 5 at 30 mg/kg. Body weight of the mice were measured on the designated days of the mice as shown in FIG. 8.

Inhibition of MET Activity in MKN-45 Tumors Following Oral Administration of Compound 5

To evaluate the effect of Compound 5 on the inhibition of MET phosphorylation, MKN-45 tumors were harvested at either 0.5 hour after an oral dose of Compound 5 at 10 mg/kg. The level of MET phosphorylation was determined by immunoblotting combined with signal quantification by the Image Studio Digit Software. Compound 5 inhibited MET phosphorylation to 16% and 13% of the control level at Tyr-1234 and Tyr-1349, respectively (FIG. 9). In another experiment, tumors were harvested after repeated dose administration at 4 hours and 12 hours after last dose of Compound 5. The level of MET phosphorylation at Tyr-1234 was determined by ELISA. Compound 5 inhibited MET phosphorylation to 0.2% and 4.0% of control level at 4 hours and 12 hours after last dose of 10 mg/kg Compound 5 treatment; Compound 5 inhibited MET phosphorylation to 12.7% and 33.1% of control level at 4 hours and 12 hours after last dose of 10 mg/kg Compound 5 treatment (FIG. 10).

LU2503 Patient Derived Xenograft (PDX) NSCLC Model

The LU2503 is a PDX model derived from a NSCLC patient and harboring gene amplification and exon 14 skipping mutation of the Met gene. Treating mice bearing LU2503 tumors with Compound 5 at 15 mg/kg, BID for 13 days resulted in a 85% tumor regression, whereas the tumors grew from 189 mm$^3$ to 2032 mm$^3$ in the vehicle treated group (FIG. 11). No body weight loss was observed after 21 days of BID treatment with Compound 5 at 15 mg/kg (FIG. 12).

Inhition of the Growth of Ba/F3 ETV6-CSF1R Tumors

In the Ba/F3 ETV6-CSF1R xenograft tumor model, the growth of tumor is presumably dependent on the exotopic CSF1R activity. SCID/Beige mice bearing Ba/F3 ETV6-CSF1R tumors with average tumor size of ~180 mm$^3$) were dosed with Compound 5 orally BID for 10 days (FIG. 13). The control group of mice were given vehicle only. Tumor volume (TMV) was measured by caliper on the indicated days and is shown at mean±sem in FIG. 12. The mean TMVs are significantly lower in the treated groups compared to that of the control group (p<0.05) as determined by two-way repeated ANOVA followed by post hoc analysis. Compound 5 demonstrated the ability to inhibit tumor growth at 44% and 67% at the dose of 5 mg/kg, BID and 15 mg/kg, BID, respectively. Body weight of the mice were measured on the designated days of the mice as shown in FIG. 14.

The PD Marker Evaluation of Compound 5 in the Subcutaneous MC38 Syngeneic Mouse Tumor Model Anti-tumor effects of Compound 5 on MC38 syngeneic tumors was analyzed by tumor volume. The average tumor volume of vehicle control group (G1) on day 7 was 696.3±299.7, while Compound 5 treated group (G2) was 473.5±170.4 mm$^3$. On day 11, the average tumor volume of G1 and G2 were 1142.6±290.0 and 610.4±151.8 mm$^3$, respectively. On day 11, tumor volume showed statistically significant difference between treatment groups with p<0.006, while the difference was not statistically significant on Day 7. Percent tumor volume change is shown in FIG. 15. No body weight loss and overt abnormality was observed in mice treated with Compound 5 at 15 mg/kg BID for 7 or 11 days, as showed in FIG. 16.

Figure 17:
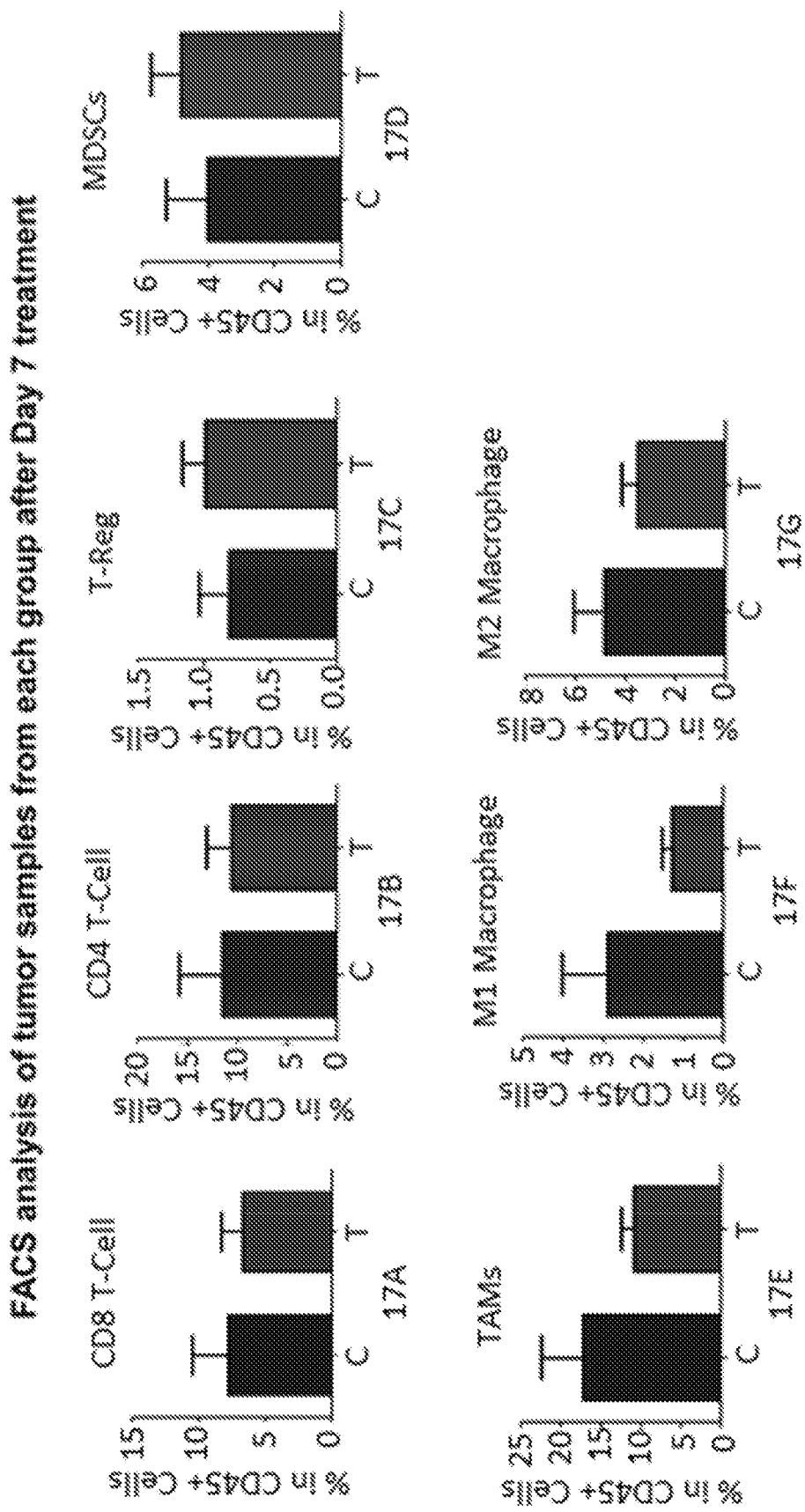
Figure 18:
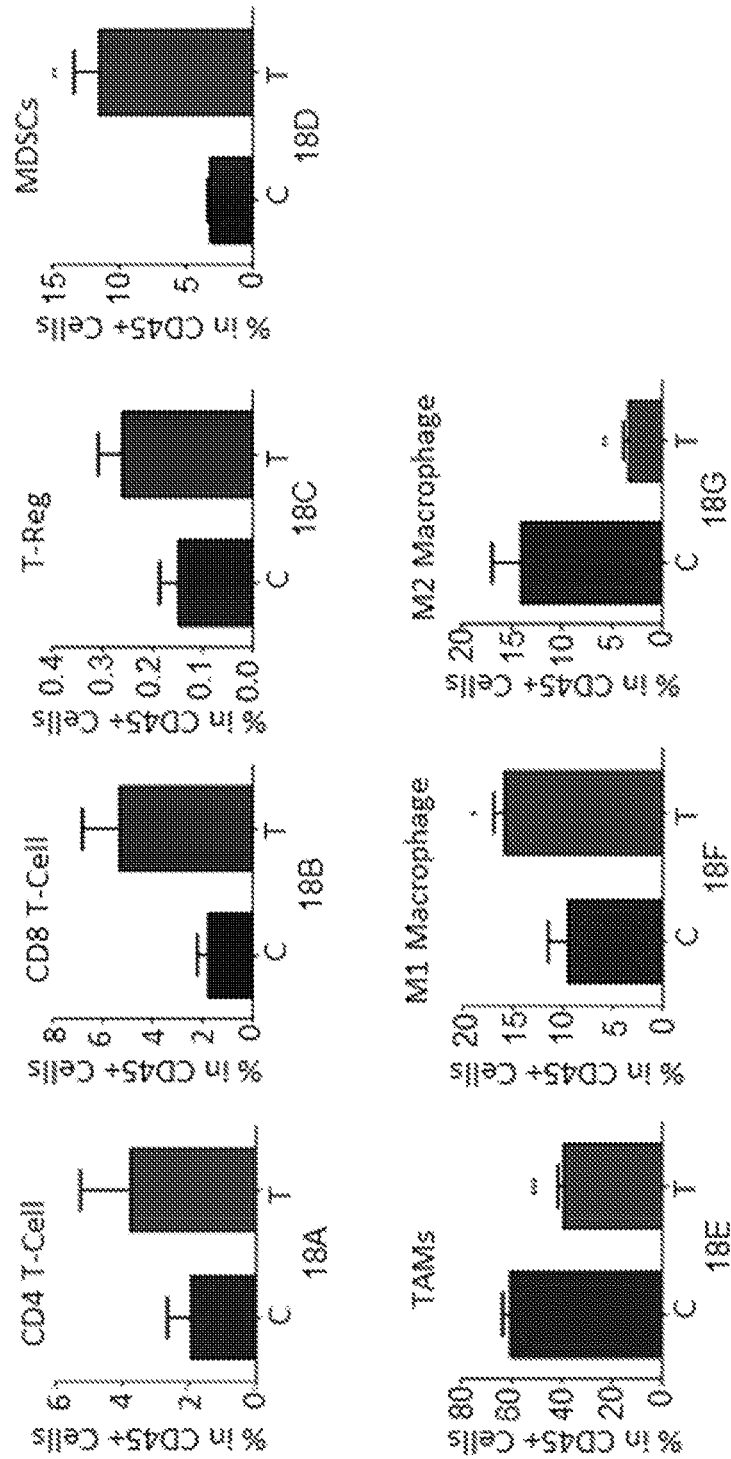

FACS analysis of tumors were performed on day 7 and day 11 for the tumor associated immune cells including tumor associated macrophages (TAM) and TAM subtypes (M1 and M2), myeloid derived suppression cells (MDSC), cytotoxic T lymphocytes (CTL, i.e. CD8+ T cells), CD4+ T cells, and regulatory T cells (Treg). Data are shown in FIGS. 17 and 18. On day 7, there were no statistically significant changes in the populations of TAM, M1, M2, MDSC, CTL, CD4+ T cells, or Treg in tumor associated leukocytes (CD45+ populations) between the control and Compound 5 treated groups, although there is a trend for a reduction in TAM cells in Compound 5 treated mice. However, on day 11, a statistically significant decrease of TAM in the total tumor leukocyte population was observed in the Compound 5 treated group compared to the control group, with a concurrent increase in the MDSC populations. Further analysis the subpopulation of TAM revealed an increase in M1 TAM and a decrease in M2 TAM in the total tumor leukocyte population in tumors in Compound 5 treated group compared to the control group. At the same time, a trend of increase of CTL cells in the total tumor leukocyte population and a statistically significant increase of CTL in the CD3+ lymphocyte population were observed in the Compound 5 treated group compared to the control group, with no statistically significant change found in the CD4+ T cells or Treg cells.

In Vivo Combination Efficacy Study of Compound 5 with PD-1 Antibody in MC38 Syngeneic Model Anti-tumor effects of Compound 5 combined with PD-1 antibody on MC38 syngeneic tumors was analyzed by tumor volume. The average tumor volume of vehicle control group (G1) on day 20 was 1938.58±729.41, Compound 5 treated group (G2) was 1220.03±521.39 mm3, PD-1 antibody treatment group was 821.24±767.16, and Compound 5 plus PD-1 antibody treatment was 515.63±350.47. On day 20, an anti-tumor synergy was observed compared the combination group to the groups of Compound 5 or PD-1 antibody treated alone. No body weight loss and overt abnormality was observed in mice treated Compound 5 and/or PD-1 antibody. Data are shown in FIGS. 19 and 20.

What is claimed is:
1. A compound having structure:
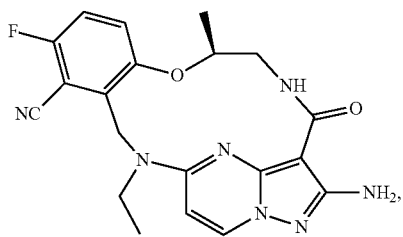 [SMILES: CCN1Cc2c(ccc(F)c2C#N)O[C@@H](C)CNC(=O)c2c(N)nn3ccc1nc23]
or a pharmaceutically acceptable salt thereof.
2. A compound having structure:
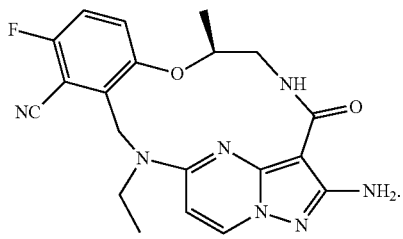 [SMILES: CCN1Cc2c(ccc(F)c2C#N)O[C@@H](C)CNC(=O)c2c(N)nn3ccc1nc23]
3. A pharmaceutical composition comprising a compound having structure:
or a pharmaceutically acceptable salt thereof, and a pharmaceutically acceptable diluent, carrier or excipient.
* * * * *